United States Patent
Hanlon et al.

(10) Patent No.: US 11,679,089 B2
(45) Date of Patent: Jun. 20, 2023

(54) METHODS OF MANUFACTURING AMINO ACID COMPOSITIONS

(71) Applicant: AXCELLA HEALTH INC., Cambridge, MA (US)

(72) Inventors: Thomas Hanlon, Concord, MA (US); Ralph Yamamoto, Woburn, MA (US); Denise K. Kwok, Arlington, MA (US); Daniel Rothenberg, Cambridge, MA (US); Andrew M. Wood, Newtown, PA (US)

(73) Assignee: AXCELLA HEALTH INC., Cambridge, MA (US)

( * ) Notice: Subject to any disclaimer, the term of this patent is extended or adjusted under 35 U.S.C. 154(b) by 0 days.

(21) Appl. No.: 16/446,171

(22) Filed: Jun. 19, 2019

(65) Prior Publication Data
US 2019/0388374 A1    Dec. 26, 2019

Related U.S. Application Data

(60) Provisional application No. 62/687,725, filed on Jun. 20, 2018.

(51) Int. Cl.
| | | |
|---|---|---|
| *A61K 31/198* | (2006.01) | |
| *A61K 9/00* | (2006.01) | |
| *A61K 9/14* | (2006.01) | |
| *A61K 31/197* | (2006.01) | |

(52) U.S. Cl.
CPC .......... *A61K 31/198* (2013.01); *A61K 9/0053* (2013.01); *A61K 9/14* (2013.01); *A61K 31/197* (2013.01)

(58) Field of Classification Search
CPC ............ A61K 9/14; A61K 31/197–198; A61K 2300/00
See application file for complete search history.

(56) References Cited

U.S. PATENT DOCUMENTS

| | | | |
|---|---|---|---|
| 4,871,550 A * | 10/1989 | Millman | ................. A23L 29/30 424/601 |
| 9,878,004 B2 | 1/2018 | Williams et al. | |
| 10,201,513 B2 | 2/2019 | Hamill et al. | |
| 10,238,617 B2 | 3/2019 | Hamill et al. | |
| 10,471,034 B2 | 11/2019 | Hamill et al. | |
| 10,596,136 B2 | 3/2020 | Chakravarthy et al. | |
| 10,660,870 B2 | 5/2020 | Comb et al. | |
| 10,682,325 B2 | 6/2020 | Comb et al. | |
| 2001/0041187 A1 | 11/2001 | Hastings et al. | |

(Continued)

FOREIGN PATENT DOCUMENTS

| | | |
|---|---|---|
| EP | 0891719 A1 | 1/1999 |
| EP | 3298908 A2 | 3/2018 |

(Continued)

OTHER PUBLICATIONS

International Search Report and Written Opinion issued in PCT/US2019/037902, dated Sep. 30, 2019.

(Continued)

*Primary Examiner* — Dominic Lazaro
(74) *Attorney, Agent, or Firm* — K&L Gates LLP

(57) ABSTRACT

This disclosure provides methods of manufacturing large-scale blended preparations comprising one or more amino acids wherein the preparations have certain properties.

15 Claims, 16 Drawing Sheets

(56) References Cited

U.S. PATENT DOCUMENTS

| | | |
|---|---|---|
| 2004/0213838 A1 | 10/2004 | Mazer et al. |
| 2006/0073254 A1 | 4/2006 | Catani et al. |
| 2007/0286909 A1* | 12/2007 | Smith ............... A61K 31/455 |
| | | 424/682 |
| 2012/0251633 A1* | 10/2012 | Buijsse ............... A61K 9/1617 |
| | | 424/702 |
| 2016/0243202 A1 | 8/2016 | Vincent |
| 2016/0339078 A1 | 11/2016 | Hamill et al. |
| 2018/0015122 A1 | 1/2018 | Villamil Torres et al. |
| 2018/0125926 A1 | 5/2018 | Williams et al. |
| 2018/0169044 A1 | 6/2018 | Hamill et al. |
| 2018/0169045 A1 | 6/2018 | Hamill et al. |
| 2018/0169046 A1 | 6/2018 | Hamill et al. |
| 2018/0169047 A1 | 6/2018 | Hamill et al. |
| 2018/0207118 A1 | 7/2018 | Hamill et al. |
| 2018/0207119 A1 | 7/2018 | Hamill et al. |
| 2018/0296516 A1 | 10/2018 | Hamill et al. |
| 2019/0046486 A1 | 2/2019 | De Rienzo et al. |
| 2019/0046487 A1 | 2/2019 | Comb et al. |
| 2019/0105294 A1 | 4/2019 | Hamill et al. |
| 2019/0247351 A1 | 8/2019 | Comb et al. |
| 2019/0388374 A1 | 12/2019 | Hanlon et al. |
| 2019/0388375 A1 | 12/2019 | Hanlon et al. |
| 2019/0388376 A1 | 12/2019 | Carroll et al. |
| 2019/0388377 A1 | 12/2019 | Hamill et al. |
| 2020/0016104 A1 | 1/2020 | Chakravarthy et al. |
| 2020/0163919 A1 | 5/2020 | Carroll et al. |
| 2020/0281882 A1 | 9/2020 | Chakravarthy et al. |
| 2020/0306214 A1 | 10/2020 | Comb et al. |
| 2020/0330417 A1 | 10/2020 | Hamill et al. |

FOREIGN PATENT DOCUMENTS

| | | | |
|---|---|---|---|
| JP | 2012136492 A | 7/2012 | |
| WO | 9414458 A1 | 7/1994 | |
| WO | 2004092202 A1 | 10/2004 | |
| WO | 2005065726 A1 | 7/2005 | |
| WO | 2006062238 A1 | 6/2006 | |
| WO | 2015015149 A1 | 2/2015 | |
| WO | 2015048333 A2 | 4/2015 | |
| WO | 2015048340 A2 | 4/2015 | |
| WO | 2015048342 A2 | 4/2015 | |
| WO | 2015048345 A2 | 4/2015 | |
| WO | 2015048346 A2 | 4/2015 | |
| WO | 2015048348 A2 | 4/2015 | |
| WO | WO-2017055997 A1 * | 4/2017 | ........... A61K 9/5047 |
| WO | 2018173986 A1 | 9/2018 | |
| WO | 2019246298 A1 | 12/2019 | |
| WO | 2019246299 A1 | 12/2019 | |
| WO | 2019246310 A1 | 12/2019 | |

OTHER PUBLICATIONS

Martina et al., "Long-Term N-Acetylcysteine and L-Arginine Administration Reduces Endothelial Activation and Systolic Blood Pressure in Hyptertensive Patients With Type 2 Diabetes," Diabetes Care (2008) vol. 31, No. 5, pp. 940-944.

Tsuda et al., "Combined Effect of Arginine, Valine, and Serine on Excercise-Induced Fatigue in Healthy Volunteers: A Randomized, Double-Blind, Placebo-Controlled Crossover Study," Nutrients (2019) vol. 11, Article 862, 12 pages.

Al-Ali et al., "Impacts of High Moisture Wet Granulation and Novel Microwave Drying on the Textural Characteristics of Pharmaceutical Particles," IOP Conf Ser: Mater Sci Eng (2018) vol. 454, Article 012056, 8 pages.

U.S. Appl. No. 17/067,187, filed Oct. 9, 2020.
U.S. Appl. No. 17/156,071, filed Jan. 22, 2021.

* cited by examiner

Fig. 3A

| Ingredient | Formula (%) |
|---|---|
| Fusi-BCAA Instantized Blend | 22.73% |
|  | 11.37% |
|  | 5.70% |
|  | 5.70% |
| L-Arginine HCl | 17.05% |
| L-Glutamine | 22.73% |
| N-acetylcysteine | 2.84% |
| L-Lysine (K) | 2.84% |
| L-Histidine (H) | 0.95% |
| L-Phenylalanine (F) | 0.95% |
| L-Threonine (T) | 1.89% |
| Citric Acid | 7.58% |
| Alecolec F100 | 9.47% |
| Acesulfame-Potassium | 0.57% |
| Sucralose | 0.38% |
| XanthanTicaxan Rapid-3 | 2.69% |
| Vanilla Custard | 0.68% |
| Nat Orange WONF | 4.07% |
| Lime | 0.57% |
| Lemon | 0.57% |
| Bitterness Masking | 1.34% |
| FD&C Yellow 6 | 0.10% |
| Total | 100.00% |

T = 0

T = 40 mins

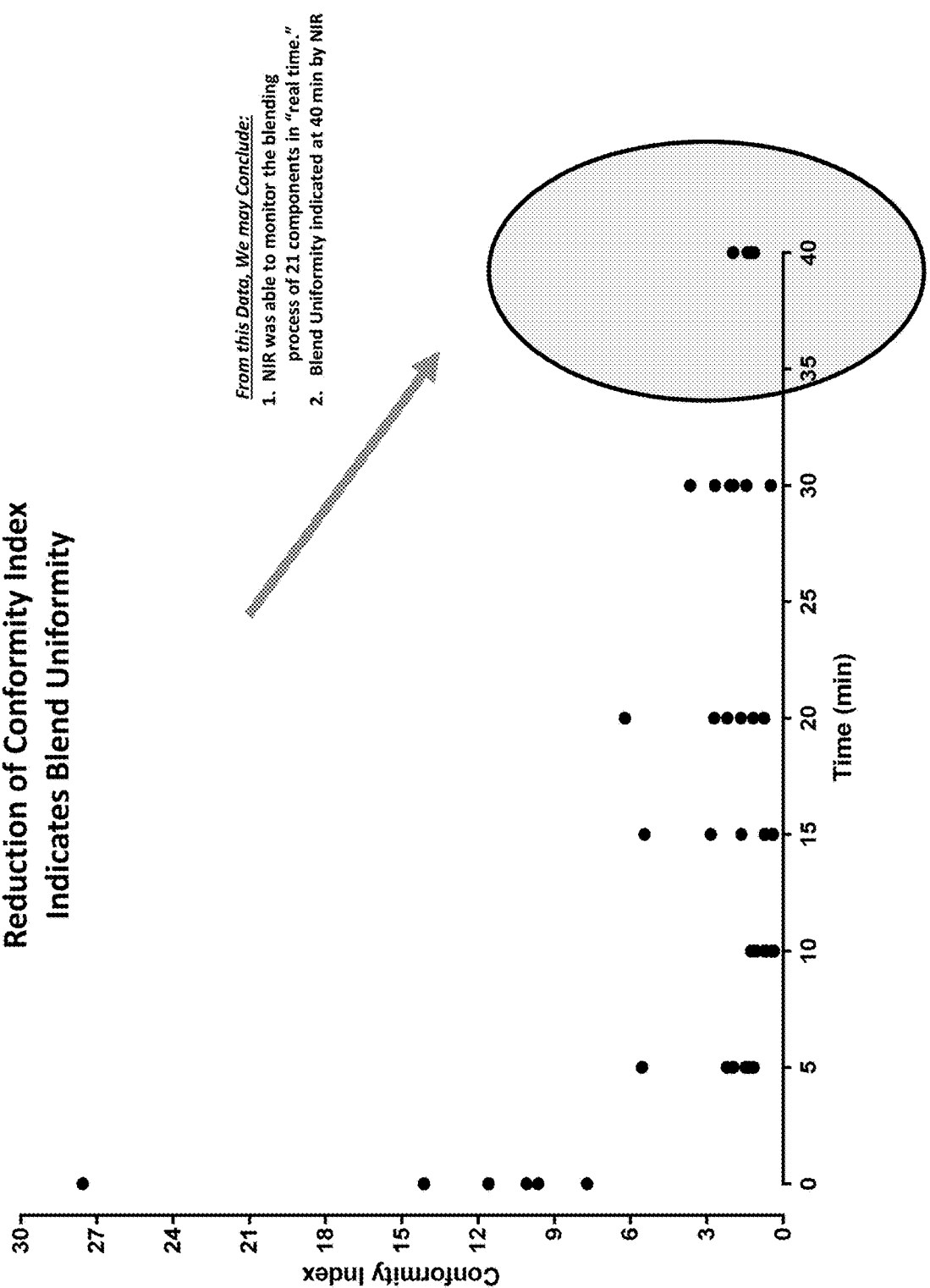

Statistical Analysis of AXA2678 Assessment of Content Uniformity

L<15: Each Amino Acid from this Blend Conforms to USP Acceptance Values for Content Uniformity

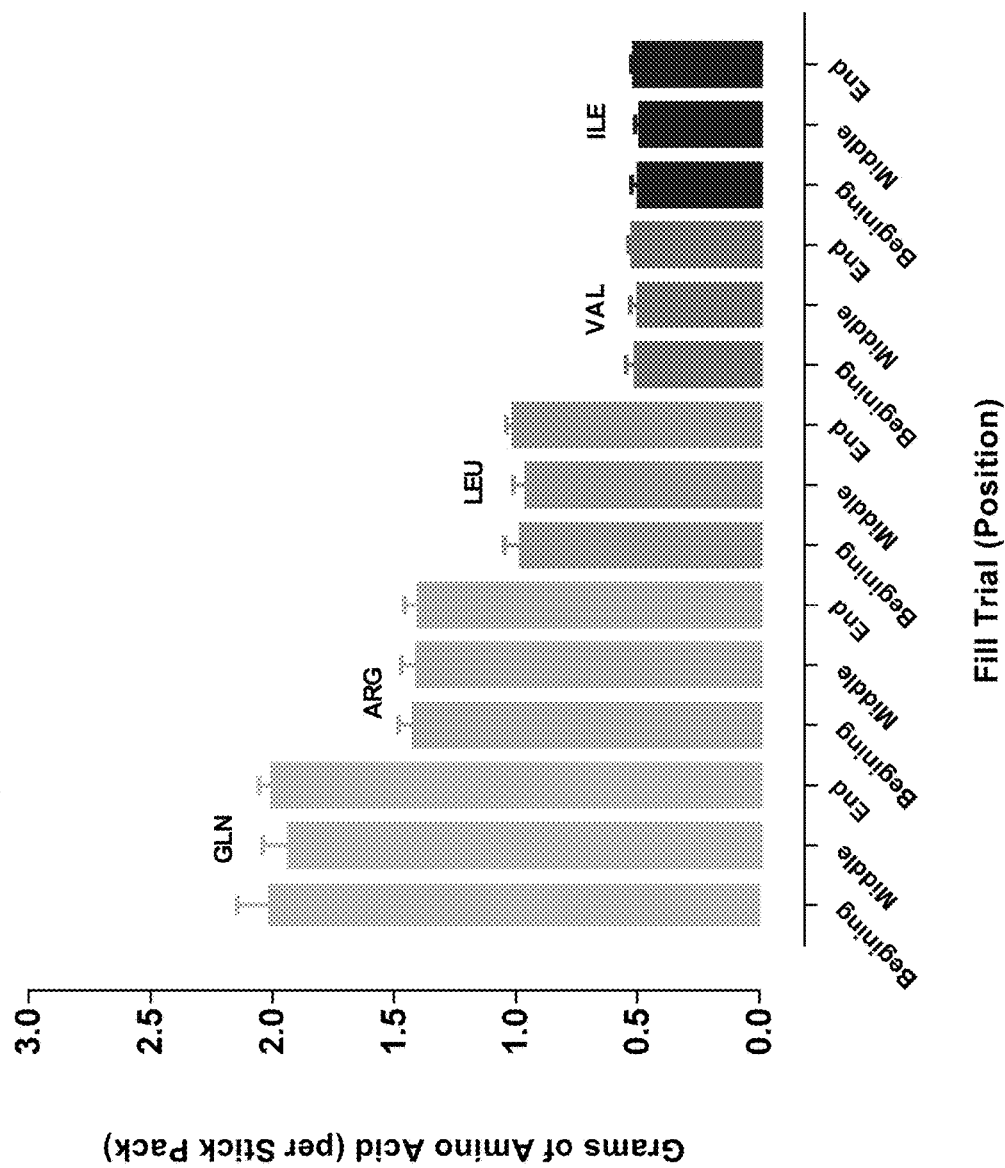

Fig 8A
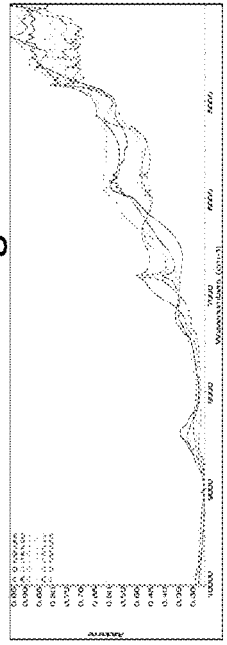
AXA 1665 Spectra Change over Blending
AXA1665 0 min → 5 min → 10 min
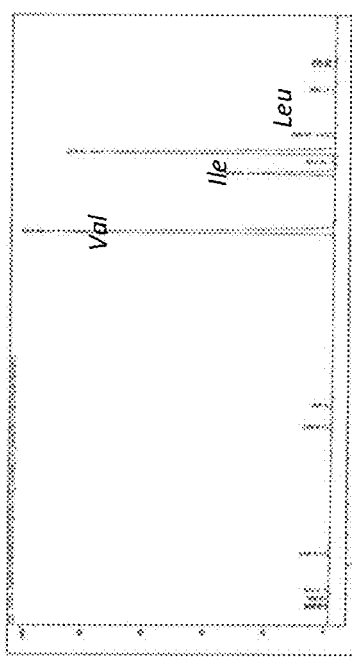
Fig 8B
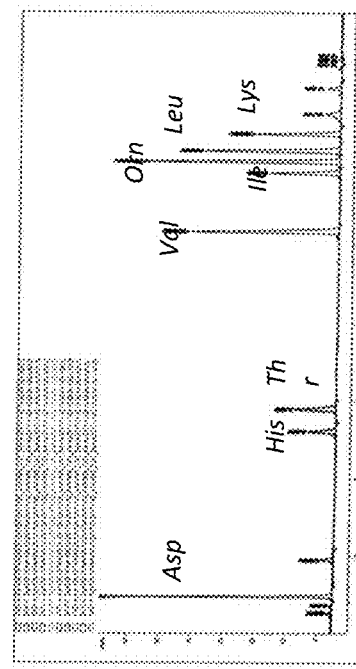
Fig 8C

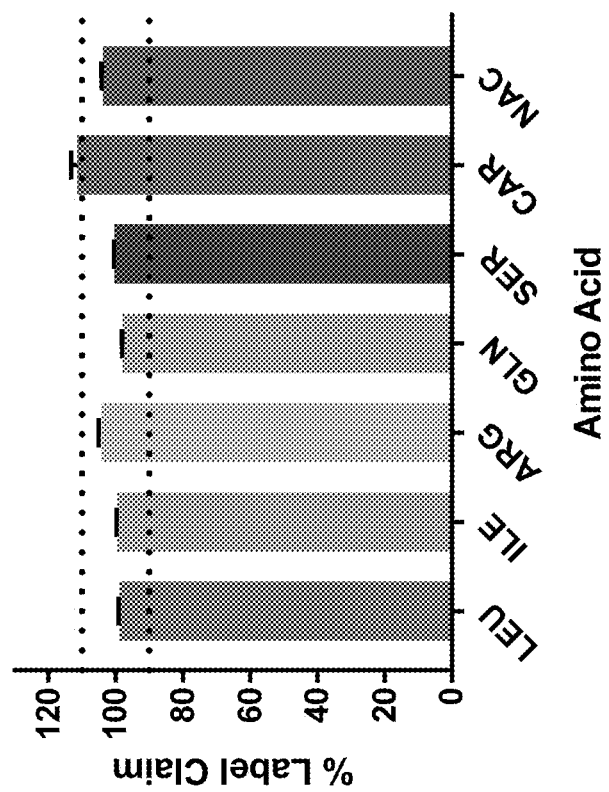

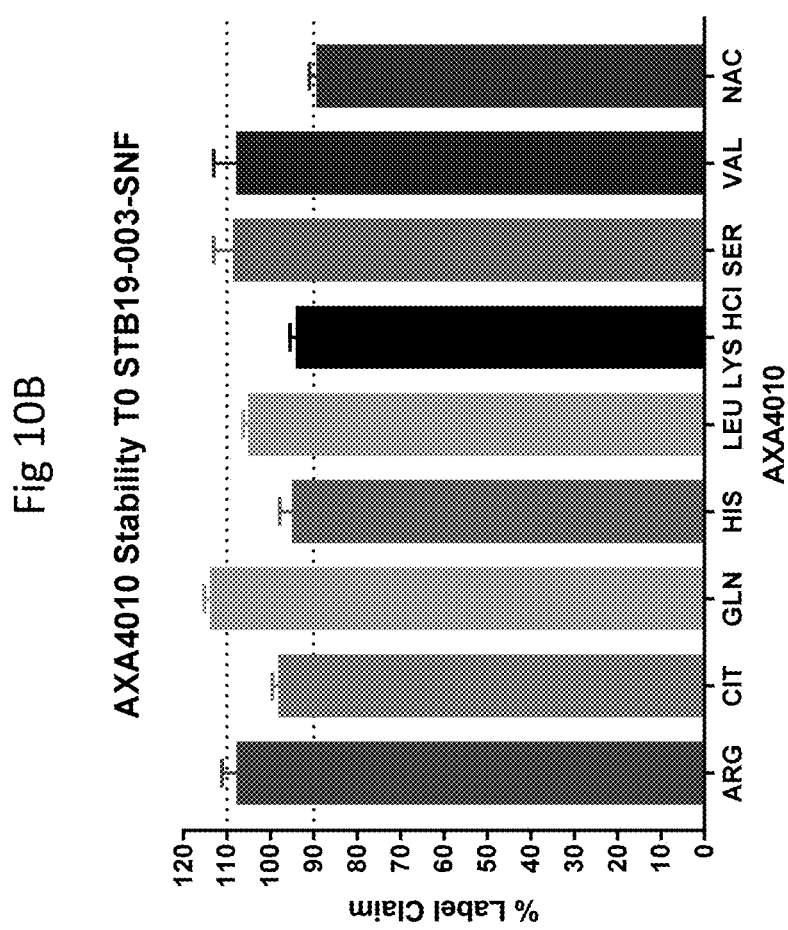

METHODS OF MANUFACTURING AMINO ACID COMPOSITIONS

RELATED APPLICATIONS

This application claims priority to U.S. Ser. No. 62/687,725 filed Jun. 20, 2018, the contents of which is incorporated herein by reference in its entirety.

BACKGROUND

Mixtures of solids, e.g., amino acids, have many uses in the food and pharmaceutical industries. When mixtures are needed for particular purposes, specialized mixing and blending techniques may be required to achieve the necessary properties for the mixture to be suitable for the purpose. While many different mixing and blending techniques exist in the art, the selection, combination, optimization, and execution of particular techniques for a given application remains a significant hurdle to manufacturing mixtures for particular purposes.

Thus, there is a need to develop methods of manufacturing mixtures of amino acids for particular purposes and with particular properties.

SUMMARY

Provided herein are methods of manufacturing dry blended preparations of a plurality of amino acid entities. In one aspect, the dry blended preparations meet a pharmaceutically accepted standard and are pharmaceutical grade dry blended preparations (PGDBP). Also provided are dry blended preparations, e.g., PGDBPs, produced by the methods described herein.

In one aspect, the invention is directed to a method of manufacturing a dry blended preparation, e.g., pharmaceutical grade dry blended preparation (PGDBP), comprising pharmaceutical grade amino acid entities, said method comprising:
  forming a combination of at least 4 pharmaceutical grade amino acid entities and blending the combination for a time sufficient to produce a dry blended preparation, e.g., PGDBP.

In another aspect, the invention is directed to a method of manufacturing a plurality of portions of a dry blended preparation, e.g., pharmaceutical grade dry blended preparation (PGDBP), comprising pharmaceutical grade amino acid entities, said method comprising:
  blending a combination of at least 4 pharmaceutical grade amino acid entities for a time sufficient to achieve a reference standard for a PGDBP, and
  dividing the PGDBP into a plurality of portions,
  wherein each portion of the plurality of portions of the blended preparation meets the reference standard for a dry blended preparation, e.g., PGDBP.

In another aspect, the invention is directed to a method of manufacturing a dry blended preparation, e.g., pharmaceutical grade dry blended preparation (PGDBP), comprising at least 4 pharmaceutical grade amino acid entities, e.g., an Active Moiety comprising at least 4 pharmaceutical grade amino acid entities, said method comprising:
  forming a combination of at least 4 pharmaceutical grade amino acid entities and blending the combination for a time sufficient to achieve a dry blended preparation, e.g., PGDBP.

In another aspect, the invention is directed to a method of manufacturing a plurality of portions of a dry blended preparation, e.g., pharmaceutical grade dry blended preparation (PGDBP), e.g., comprising an Active Moiety comprising at least 4 pharmaceutical grade amino acid entities, said method comprising:
  providing a PGDBP comprising at least 4 pharmaceutical grade amino acid entities, e.g., an Active Moiety comprising at least 4 pharmaceutical grade amino acid entities, made by a method described herein, e.g., a method of any of claims 36-80; and
  dividing the PGDBP into a plurality of portions,
  thereby manufacturing a plurality of portions of a dry blended preparation, e.g., PGDBP.

In another aspect, the invention is directed to a dry blended preparation, e.g., pharmaceutical grade dry blended preparation (PGDBP), comprising at least 4 pharmaceutical grade amino acid entities, e.g., an Active Moiety comprising at least 4 pharmaceutical grade amino acid entities, e.g. described herein.

In another aspect, the invention is directed to a plurality of portions of a dry blended preparation, e.g., pharmaceutical grade dry blended preparation (PGDBP), comprising at least 4 pharmaceutical grade amino acid entities, e.g., an Active Moiety comprising at least 4 pharmaceutical grade amino acid entities, the plurality having one or more of the following properties:
  a) the plurality comprises at least 10 portions, e.g., at least 10, 50, 100, 200, 300, 400, 500, 600, 700, 800, 900, 1000, 1200, 1400, 1600, 1800, 2000, 3000, 4000, 5000, 6000, 7000, 8000, 9000, 10,000, or more portions;
  b) the PGDBP was made by a method described herein;
  c) each portion is a unit dosage form;
  d) each portion comprises 1 to 50 grams of PGDBP; or
  e) each portion comprises at least 2, 3, 4, 5, 6, 7, 8, 9, 10, 15, 20, 25, 30, 35, 40, 45, 50, 60, 70, 80, 90, 100, 150, 200, 250, 300, 350, 400, 450, or 500 g or 1, 2, 3, 4, or 5 kg of PGDBP.

In another aspect, the invention is directed to a method of manufacturing a plurality of of portions described herein, comprising:
  providing a portion from the plurality of portions and evaluating whether the portion meets a reference standard, and
  responsive to the evaluation, selecting and/or executing a downstream processing step selected from fill and finish, packaging, labeling, shipping, or release into commerce, for the plurality of portions.

In another aspect, the invention is directed to a dosage form comprising at least 1, 2, 3, 4, 5, 6, 7, 8, 9, 10, 15, 20, 25, 30, 35, 40, 45, 50, 60, 70, 80, 90, 100, 150, 200, 250, 300, 350, 400, 450, or 500 grams of a dry blended preparation, e.g., pharmaceutical grade dry blended preparation (PGDBP), comprising: at least 4 pharmaceutical grade amino acid entities (e.g., an Active Moiety comprising at least 4 pharmaceutical grade amino acid entities), and at least one excipient, e.g., an oral administration component.

In another aspect, the invention is directed to a dosage form comprising at least 1, 2, 3, 4, 5, 6, 7, 8, 9, 10, 15, 20, 25, 30, 35, 40, 45, 50, 60, 70, 80, 90, 100, 150, 200, 250, 300, 350, 400, 450, or 500 grams of a PGDBP described herein, wherein the dosage form comprises at least one at least one excipient, e.g., an oral administration component.

Additional features of any of the aforesaid methods or compositions include one or more of the following enumerated embodiments.

Those skilled in the art will recognize, or be able to ascertain using no more than routine experimentation, many equivalents to the specific embodiments of the invention described herein. Such equivalents are intended to be encompassed by the following enumerated embodiments.

ENUMERATED EMBODIMENTS

1. A method of manufacturing a dry blended preparation, e.g., pharmaceutical grade dry blended preparation (PGDBP), comprising pharmaceutical grade amino acid entities, said method comprising:
forming a combination of at least 4 pharmaceutical grade amino acid entities and blending the combination for a time sufficient to produce a dry blended preparation, e.g., PGDBP.

2. The method of embodiment 1, wherein the number of amino acids is 4, 5, 6, 7, 8, 9, 10, 11, 12, 13, 14, 15, 16, 17, 18, 19, or 20.

3. The method of either of embodiments 1 or 2, wherein the at least 4 pharmaceutical grade amino acid entities together comprise an Active Moiety.

4. The method of any of embodiments 1-3, wherein the PGDBP is a large-scale PGDBP.

5. The method of any of embodiments 1-4, wherein the PGDBP meets a standard for composition uniformity.

6. The method of embodiment 5, wherein composition uniformity, e.g., blend uniformity, comprises the amount of a pharmaceutical grade amino acid entity (e.g., in weight % of total pharmaceutical grade amino acid entities) at a sampling point differing from the amount of a pharmaceutical grade amino acid entity present in the PGDBP by less than a predetermined amount.

7. The method of embodiment 5, wherein composition uniformity, e.g., blend uniformity, comprises the amount of the Active Moiety (e.g., one or more pharmaceutical grade amino acid entities of the Active Moiety; e.g., in weight % of total pharmaceutical grade amino acid entities) at a sampling point differing from the amount of the Active Moiety present in the PGDBP by less than a predetermined amount.

8. The method of either of embodiments 6 or 7, wherein the predetermined amount is 10% of the amount of the Active Moiety (e.g., one or more pharmaceutical grade amino acid entities of the Active Moiety; e.g., in weight % of total pharmaceutical grade amino acid entities) or pharmaceutical grade amino acid entity present in the combination or PGDBP.

9. The method of either of embodiments 6 or 7, wherein the predetermined amount is 5% of the amount of the Active Moiety (e.g., one or more pharmaceutical grade amino acid entities of the Active Moiety; e.g., in weight % of total pharmaceutical grade amino acid entities) or pharmaceutical grade amino acid entity present in the combination or PGDBP.

10. The method of either of claims 6 or 7, wherein the predetermined amount is 1% of the amount of the Active Moiety (e.g., one or more pharmaceutical grade amino acid entities of the Active Moiety; e.g., in weight % of total pharmaceutical grade amino acid entities) or pharmaceutical grade amino acid entity present in the combination or PGDBP.

11. The method of any of embodiments 5-10, further comprising acquiring a value for the amount of a pharmaceutical grade amino acid entity or Active Moiety (e.g., one or more pharmaceutical grade amino acid entities of the Active Moiety) at a sampling point in one or both of the combination or PGDBP.

12. The method of embodiment 11 wherein acquiring a value comprises using liquid chromatography mass spectrometry (LC-MS).

13. The method of embodiment 11 wherein acquiring a value comprises near IR (NIR) spectroscopy.

14. The method of embodiment 11 wherein acquiring a value comprises high performance liquid chromatography (HPLC).

15. The method of any of embodiments 11-14, wherein acquiring a value comprises derivatizing the amino acid entity with a detectable moiety.

16. The method of embodiment 15 wherein the detectable moiety is a chromophore.

17. The method of embodiment 15 wherein the detectable moiety is a fluorescent moiety.

18. The method of embodiment 17 wherein the fluorescent moiety is ortho phthalaldehyde (OPA) or fluorenyl-methoxy chloroformate (FMOC)).

19. The method of any of embodiments 1-18, further comprising portioning the PGDBP, e.g., responsive to the acquired value.

20. The method of any of embodiments 1-19, wherein the PGDBP is suitable for oral administration.

21. The method of any of embodiments 1-20 wherein the PGDBP further comprises one or more excipients.

22. The method of embodiment 21, wherein the excipient is an excipient that is suitable for oral administration.

23. The method of either embodiment 21 or 22, wherein the excipient is a flavoring agent.

24. The method of embodiment 23, wherein the flavoring agent produces a flavor selected from peach, mango, lemon, lime, orange, and orange creamsicle.

25. The method of embodiment 24, wherein the flavor is orange creamsicle.

26. The method of any of embodiments 21-25, wherein the excipient is a substance generally regarded as safe (GRAS), e.g., a substance from the Federal Drug Administration's GRAS Notice List.

27. The method of any of embodiments 21, 22, or 26, wherein the excipient is lecithin.

28. The method of any of embodiments 1-26, wherein the PGDBP does not comprise lecithin.

29. The method of any of embodiments 1-28, wherein the PGDBP is suitable for mixture with a liquid for oral administration.

30. The method of any of embodiments 1-29, wherein the PGDBP is not sufficiently sterile for parenteral administration.

31. The method of any of embodiments 1-30, wherein the level of microbial contamination of the PGDBP is below the level permitted in food.

32. A method of manufacturing a plurality of portions of a dry blended preparation, e.g., pharmaceutical grade dry blended preparation (PGDBP), comprising pharmaceutical grade amino acid entities, said method comprising:
blending a combination of at least 4 pharmaceutical grade amino acid entities for a time sufficient to achieve a reference standard for a PGDBP, and
dividing the PGDBP into a plurality of portions,
wherein each portion of the plurality of portions of the blended preparation meets the reference standard for a dry blended preparation, e.g., PGDBP.

33. The method of embodiment 32, wherein the number of amino acids is 4, 5, 6, 7, 8, 9, 10, 11, 12, 13, 14, 15, 16, 17, 18, 19, or 20.

34. The method of either of embodiments 32 or 33, wherein the amount of a pharmaceutical grade amino acid entity in each portion of the plurality of portions differs by no more than 10% from a reference value, and wherein the reference value is the amount of the pharmaceutical grade amino acid entity in any other portion of the plurality of portions.

35. The method of any of embodiments 32-34, further comprising acquiring a value for the amount of a pharmaceutical grade amino acid entity or Active Moiety (e.g., one or more pharmaceutical grade amino acid entities of the Active Moiety) in a portion or plurality of portions in the plurality of portions, wherein responsive to the acquired value(s) a downstream processing step, e.g., packaging, labeling, or shipping, for the plurality of portions is taken.

36. A method of manufacturing a dry blended preparation, e.g., pharmaceutical grade dry blended preparation (PGDBP), comprising at least 4 pharmaceutical grade amino acid entities, e.g., an Active Moiety comprising at least 4 pharmaceutical grade amino acid entities, said method comprising:
    forming a combination of at least 4 pharmaceutical grade amino acid entities and blending the combination for a time sufficient to achieve a dry blended preparation, e.g., PGDBP.

37. The method of embodiment 36, wherein the blending is sufficient to achieve blend and portion uniformity without generating impurities or inducing blend heterogeneity.

38. The method of either of embodiments 36 or 37, wherein the combination comprises 4, 5, 6, 7, 8, 9, 10, 11, 12, 13, 14, 15, 16, 17, 18, 19, or 20 pharmaceutical grade amino acid entities (e.g., the Active Moiety comprises 4, 5, 6, 7, 8, 9, 10, 11, 12, 13, 14, 15, 16, 17, 18, 19, or 20 pharmaceutical grade amino acid entities).

39. The method of any of embodiments 36-38, wherein the PGDBP is a large-scale PGDBP.

40. The method of any of embodiments 36-39, wherein the PGDBP meets a reference standard.

41. The method of embodiment 40, wherein the reference standard is set by a manufacturer of the PGDBP.

42. The method of embodiment 40, wherein the reference standard is set by a manufacturer having approval from a governmental agency to market the PGDBP.

43. The method of embodiment 40, wherein the reference standard is set by a pharmacopeal entity, or a national formulary, or found in a pharmacopeal reference, e.g., the USP or NF.

44. The method of embodiment 40, wherein the reference standard is set by a a governmental agency, e.g., a government agency that authorizes or regulates the manufacture or marketing of the PGDBP.

45. The method of embodiment 44, wherein the government agency comprises one or more of the following agencies: Federal Drug Administration (FDA), European Medicines Agency (EMA), SwissMedic, China Food and Drug Administration (CFDA), Japanese Pharmaceuticals and Medical Devices Agency (PMDA), Health Canada, Medicines and Healthcare Products Regulatory Agency (MHRA), or the International Council for Harmonisation of Technical Requirements for Pharmaceuticals for Human Use (ICH).

46. The method of any of embodiments 40-45, wherein the reference standard comprises composition uniformity.

47. The method of embodiment 46, wherein composition uniformity, e.g., blend uniformity, comprises the amount of a pharmaceutical grade amino acid entity (e.g., in weight % of total pharmaceutical grade amino acid entities) at a sampling point differing from the amount of a pharmaceutical grade amino acid entity present in the PGDBP by less than a predetermined amount.

48. The method of embodiment 46, wherein composition uniformity, e.g., blend uniformity, comprises the amount of the Active Moiety (e.g., one or more pharmaceutical grade amino acid entities of the Active Moiety; e.g., in weight % of total pharmaceutical grade amino acid entities) at a sampling point differing from the amount of the Active Moiety present in the PGDBP by less than a predetermined amount.

49. The method of either embodiment 47 or 48, wherein the predetermined amount is 1, 2, 3, 4, 5, 6, 7, 8, 9, or 10%, e.g., of the total amount of the pharmaceutical grade amino acid entity or Active Moiety present in the PGDBP.

50. The method of embodiment 49, wherein the predetermined amount is 10% of the total amount of the pharmaceutical grade amino acid entity or Active Moiety present in the PGDBP.

51. The method of any of embodiments 36-50, further comprising acquiring a value for the amount of a pharmaceutical grade amino acid entity or Active Moiety at a sampling point in one or both of the combination or PGDBP.

52. The method of any of embodiments 36-50, further comprising acquiring a value for the amount of a pharmaceutical grade amino acid entity or Active Moiety at each of a plurality of points in one or both of the combination or PGDBP, or in a test portion (e.g., of the combination or PGDBP).

53. The method of any of embodiments 36-52, wherein the amount of a pharmaceutical grade amino acid entity or Active Moiety at one or a plurality of points (e.g., at least 50, 60, 70, 80, 90, 95, or 99% of points) differs by no more than 10% from a reference value.

54. The method of embodiment 53, wherein the reference value is the total amount of the pharmaceutical grade amino acid entity or Active Moiety present in the combination or PGDBP.

55. The method of any of embodiments 51-54, wherein acquiring a value comprises the use of near infrared spectroscopy (NIR).

56. The method of any of embodiments 51-54, wherein acquiring a value comprises the use of liquid chromatography mass spectrometry (LC-MS).

57. The method of any of embodiments 51-54, wherein acquiring a value comprises the use of high performance liquid chromatography (HPLC).

58. The method of any of embodiments 51-57, wherein acquiring a value further comprises derivatizing one or more of the pharmaceutical amino acid entities with a detectable moiety.

59. The method of embodiment 58, wherein the detectable moiety is a fluorescent moiety.

60. The method of embodiment 59, wherein the fluorescent moiety is ortho phthalaldehyde (OPA) or fluorenylmethoxy chloroformate (FMOC).

61. The method of embodiment 58, wherein the detectable moiety is a chromophore.

62. The method of any of embodiments 51-61, further comprising, responsive to the acquired value(s), selecting or taking a downstream processing step.

63. The method of embodiment 62, wherein the downstream processing step comprises division of the PGDBP into portions.

64. The method of embodiment 63, wherein responsive to the acquired values indicating that the reference standard has been met, the PGDBP is divided into portions.

65. The method of embodiment 63, wherein responsive to the acquired values indicating that the reference standard has not been met, the combination is not divided into portions and/or the combination is blended further.

66. The method of either embodiments 63 or 64, wherein the conditions of division are sufficient such that, in at least Y % of the portions formed, the amount of a selected pharmaceutical grade amino acid entity or Active Moiety differs by no more than 10% from a reference value, wherein Y is at least 50.

67. The method of 66, wherein Y is selected from 70, 80, 90, 95, 99. 99.5, 99.9, 99.95, or 99.99, 68. The method of either of embodiments 66 or 67, wherein the reference value is the total amount of the pharmaceutical grade amino acid entity present in the PGDBP.

69. The method of any of embodiments 36-68, wherein the PGDBP is suitable for oral administration.

70. The method of any of embodiments 36-69, wherein the combination or PGDBP further comprises one or more excipients, e.g., excipients suitable for oral administration.

71. The method of any of embodiments 36-70, wherein the combination or PGDBP further comprises one or more oral administration components, e.g., flavorants or bitterness masking agents.

72. The method of any of embodiments 36-71, further comprising adding one or more excipients, e.g., excipients suitable for oral administration, e.g., oral administration components, to the combination or PGDBP.

73. The method of any of embodiments 70-72, wherein the PGDBP meets a further reference standard comprising composition uniformity with regards to the one or more excipients and/or oral administration components.

74. The method of any of embodiments 70-73, wherein the excipient or oral administration component is selected from Table 14.

75. The method of any of embodiments 70-73, wherein the excipient or oral administration component is selected from a the GRAS Notice List provided by the FDA.

76. The method of any of embodiments 63-68, wherein the PGDBP, when divided into portions, is suitable for mixture with a liquid for oral administration.

77. The method of any of embodiments 36-76, wherein the PGDBP is not sufficiently sterile for parenteral administration.

78. The method of any of embodiments 36-77, wherein the level of microbial contamination of the PGDBP is below the level permitted in food.

79. The method of any of embodiments 36-62 or 69-78, further comprising dividing the PGDBP into a plurality of portions.

80. The method of embodiment 79, wherein the division is performed under conditions such that each portion retains the reference standards of the PGDBP.

81. A method of manufacturing a plurality of portions of a dry blended preparation, e.g., pharmaceutical grade dry blended preparation (PGDBP), e.g., comprising an Active Moiety comprising at least 4 pharmaceutical grade amino acid entities, said method comprising:
providing a PGDBP comprising at least 4 pharmaceutical grade amino acid entities, e.g., an Active Moiety comprising at least 4 pharmaceutical grade amino acid entities, made by a method described herein, e.g., a method of any of embodiments 36-80; and
dividing the PGDBP into a plurality of portions,
thereby manufacturing a plurality of portions of a dry blended preparation, e.g., PGDBP.

82. The method of embodiment 81, wherein providing comprises forming a combination of at least 4 pharmaceutical grade amino acid entities, e.g., an Active Moiety comprising at least 4 pharmaceutical grade amino acid entities, and blending the combination for a time sufficient to achieve a PGDBP.

83. The method of either of embodiments 81 or 82, wherein from the combination comprises 4, 5, 6, 7, 8, 9, 10, 11, 12, 13, 14, 15, 16, 17, 18, 19, or 20 pharmaceutical grade amino acid entities (e.g., the Active Moiety comprises 4, 5, 6, 7, 8, 9, 10, 11, 12, 13, 14, 15, 16, 17, 18, 19, or 20 pharmaceutical grade amino acid entities).

84. The method of any of embodiments 81-83, wherein the PGDBP meets a reference standard.

85. The method of embodiment 84, wherein the reference standard is set by a manufacturer of the PGDBP.

86. The method of embodiment 84, wherein the reference standard is set by a manufacturer having approval from a governmental agency to market the PGDBP.

87. The method of embodiment 84, wherein the reference standard is set by a pharmacopeal entity, or a national formulary, or found in a pharmacopeal reference, e.g., the USP or NF.

88. The method of embodiment 84, wherein the reference standard is set by a a governmental agency, e.g., a government agency that authorizes or regulates the manufacture or marketing of the PGDBP.

89. The method of embodiment 88, wherein the government agency comprises one or more of the following agencies: Federal Drug Administration (FDA), European Medicines Agency (EMA), SwissMedic, China Food and Drug Administration (CFDA), Japanese Pharmaceuticals and Medical Devices Agency (PMDA), Health Canada, Medicines and Healthcare Products Regulatory Agency (MHRA), or the International Council for Harmonisation of Technical Requirements for Pharmaceuticals for Human Use (ICH).

90. The method of any of embodiments 84-89, wherein the plurality of portions of a PGDBP meet the reference standard.

91. The method of any of embodiments 84-90, wherein at least 50, 60, 70, 80, 90, 95, 99, 99.9, 99.99, or 100% of the portions of the plurality of portions of a PGDBP meet the reference standard.

92. The method of any of embodiments 84-91, wherein the reference standard comprises composition uniformity, e.g., blend uniformity and/or portion uniformity.

93. The method of embodiment 92, wherein composition uniformity, e.g., blend uniformity, comprises the amount of a pharmaceutical grade amino acid entity or Active Moiety (e.g., in weight % of total pharmaceutical grade amino acid entities) in a portion differing from the amount of a pharmaceutical grade amino acid entity or Active Moiety present in the PGDBP by less than a predetermined amount.

94. The method of embodiment 93, wherein the predetermined amount is 1, 2, 3, 4, 5, 6, 7, 8, 9, or 10%, e.g., of the total amount of the pharmaceutical grade amino acid entity or Active Moiety present in the PGDBP.

95. The method of embodiment 94, wherein the predetermined amount is 10% of the total amount of the pharmaceutical grade amino acid entity or Active Moiety present in the PGDBP.

96. The method of any of embodiments 81-95, wherein each portion is suitable for mixing with a liquid and oral administration.

97. The method of any of embodiments 81-96, wherein the portion is a unit dosage disposed in a container suitable for opening and use by an end user.

98. The method of any of embodiments 81-97, wherein composition uniformity, e.g., portion uniformity, comprises the amount of a pharmaceutical grade amino acid entity in a portion of the plurality of portions differing by no more than 1, 2, 5, or 10% from a reference value.

99. The method of any of embodiments 81-97, wherein composition uniformity, e.g., portion uniformity, comprises the amount of the Active Moiety, e.g., one or more pharmaceutical grade amino acid entities of the Active Moiety, in a portion of the plurality of portions differing by no more than 1, 2, 5, or 10% from a reference value.

100. The method of either embodiment 98 or 99, wherein composition uniformity, e.g., portion uniformity, comprises differing by no more than 10% from a reference value.

101. The method of either of embodiments 98 or 100, wherein the reference value is the amount of the pharmaceutical grade amino acid entity in any other portion of the plurality of portions.

102. The method of either of embodiments 99 or 100, wherein the reference value is the amount of the Active Moiety (e.g. the amount of one or more pharmaceutical grade amino acid entities of the Active Moiety) in any other portion of the plurality of portions.

103. The method of either of embodiments 98 or 100, wherein the reference value is the average or median amount of the pharmaceutical grade amino acid entity in the portions of the plurality of portions.

104. The method of either of embodiments 99 or 100, wherein the reference value is the average or median amount of the Active Moiety (e.g. the amount of one or more pharmaceutical grade amino acid entities of the Active Moiety) in the portions of the plurality of portions.

105. The method of any of embodiments 81-104, wherein the plurality of portions comprises a plurality of test portions.

106. The method of embodiment 105, wherein the reference value is the average or median amount of the pharmaceutical grade amino acid entity in the plurality of test portions.

107. The method of embodiment 105, wherein the reference value is the average or median amount of the Active Moiety (e.g. the amount of one or more pharmaceutical grade amino acid entities of the Active Moiety) in the plurality of test portions.

108. The method of any of embodiments 105-107, further comprising acquiring a value for the amount of a pharmaceutical grade amino acid entity or for the amount of Active Moiety (e.g. the amount of one or more pharmaceutical grade amino acid entities of the Active Moiety) in each test portion in the plurality of test portions.

109. The method of embodiment 108, wherein the test portions comprise at least 1, 5, 10, 20, or 50% of the plurality of portions.

110. The method of embodiment 108, wherein the test portions comprise no more than 50, 20, 10, 5, or 1% of the plurality of portions.

111. The method of any of embodiments 108-110, wherein acquiring a value comprises the use of near infrared spectroscopy (NIR).

112. The method of any of embodiments 108-110, wherein acquiring a value comprises the use of liquid chromatography mass spectrometry (LC-MS).

113. The method of any of embodiments 108-110, wherein acquiring a value comprises the use of high performance liquid chromatography (HPLC).

114. The method of any of embodiments 108-113, wherein acquiring a value further comprises derivatizing one or more of the pharmaceutical amino acid entities with a detectable moiety.

115. The method of embodiment 114, wherein the detectable moiety is a fluorescent moiety (e.g., ortho phthalaldehyde (OPA) or fluorenylmethoxy chloroformate (FMOC)).

116. The method of embodiment 114, wherein the detectable moiety is a chromophore.

117. The method of any of embodiments 108-116, wherein responsive to the acquired value(s) a downstream processing step, e.g., fill and finish, packaging, labeling, shipping, or release into commerce, for the plurality of portions is taken.

118. The method of any of embodiments 81-117, wherein each portion of the plurality of portions is suitable for oral administration.

119. The method of any of embodiments 81-118, wherein each portion of the plurality of portions further comprises one or more oral administration components, e.g., flavorants or bitterness masking agents.

120. The method of any of embodiments 81-119, wherein each portion of the plurality of portions further comprises one or more excipients, e.g., excipients suitable for oral administration.

121. The method of any of embodiments 81-120, wherein each portion of the plurality of portions is not sufficiently sterile for parenteral administration.

122. The method of any of embodiments 81-121, wherein the level of microbial contamination of each portion of the plurality of portions is below the level permitted in food.

123. The method of any of embodiments 81-122, wherein the level of endotoxin contamination of each portion of the plurality of portions is below the level permitted in food.

124. The method of any of embodiments 81-123, wherein the level of contamination, e.g., by metals, lecithin, choline, endotoxin, microbes, or other contaminants (e.g., contaminants from raw materials) of each portion of the plurality of portions is below the level permitted in food.

125. The method of embodiment 124, wherein the contamination or contaminant is less than 10, 9, 8, 7, 6, 5, 4, 3, 2, 1, 0.1, 0.01, or 0.001% (w/w) of each portion of the plurality of portions.

126. The method of embodiment 124, wherein each portion of the plurality of portions is substantially free of contamination or contaminants.

127. The method of either of embodiments 119 or 120, wherein the excipient or oral administration components are selected from Table 14.

128. The method of any of embodiments 63-68 or 81-127, wherein the portion(s) is formulated as a sachet, stick pack, or in a vial.

129. The method of any of embodiments 63-68 or 81-128, wherein the portions are formulated as pharmaceutical compositions.

130. The method of any of embodiments 81-129, wherein the plurality comprises at least 10, 50, 100, 200, 300, 400, 500, 600, 700, 800, 900, 1000, 1200, 1400, 1600, 1800, 2000, 3000, 4000, 5000, 6000, 7000, 8000, 9000, 10,000, or more portions.

131. The method of any of embodiments 81-130, wherein portions comprise 1, 2, 3, 4, 5, 6, 7, 8, 9, 10, 15, 20, 25, 30, 35, 40, 45, 50, 60, 70, 80, 90, 100, 150, 200, 250, 300, 350, 400, 450, or 500 g or 1, 2, 3, 4, or 5 kg.

132. The dry blended preparation, e.g., PGDBP, produced by any of embodiments 36-80.

133. The plurality of portions of a dry blended preparation, e.g., PGDBP, produced by any of embodiments 81-131.

134. A dry blended preparation, e.g., pharmaceutical grade dry blended preparation (PGDBP), comprising at least 4 pharmaceutical grade amino acid entities, e.g., an Active Moiety comprising at least 4 pharmaceutical grade amino acid entities.

135. The PGDBP of embodiment 134, wherein the PGDBP comprises 4, 5, 6, 7, 8, 9, 10, 11, 12, 13, 14, 15, 16, 17, 18, 19, or 20 pharmaceutical grade amino acid entities (e.g., the Active Moiety comprises 4, 5, 6, 7, 8, 9, 10, 11, 12, 13, 14, 15, 16, 17, 18, 19, or 20 pharmaceutical grade amino acid entities).

136. The PGDBP of either of embodiments 134 or 135, wherein the PGDBP is a large-scale PGDBP.

137. The PGDBP of any of embodiments 134-136, wherein the PGDBP meets a reference standard.

138. The PGDBP of embodiment 137, wherein the reference standard is set by a manufacturer of the PGDBP.

139. The PGDBP of embodiment 137, wherein the reference standard is set by a manufacturer having approval from a governmental agency to market the PGDBP.

140. The PGDBP of embodiment 137, wherein the reference standard is set by a pharmacopeal entity, or a national formulary, or found in a pharmacopeal reference, e.g., the USP or NF.

141. The PGDBP of embodiment 137, wherein the reference standard is set by a a governmental agency, e.g., a government agency that authorizes or regulates the manufacture or marketing of the PGDBP.

142. The PGDBP of embodiment 141, wherein the government agency comprises one or more of the following agencies: Federal Drug Administration (FDA), European Medicines Agency (EMA), SwissMedic, China Food and Drug Administration (CFDA), or Japanese Pharmaceuticals and Medical Devices Agency (PMDA), Health Canada, Medicines and Healthcare Products Regulatory Agency (MHRA), or the International Council for Harmonisation of Technical Requirements for Pharmaceuticals for Human Use (ICH).

143. The PGDBP of any of embodiments 137-142, wherein the reference standard comprises composition uniformity, e.g., blend uniformity.

144. The PGDBP of embodiment 143, wherein composition uniformity, e.g., blend uniformity, comprises the amount of a pharmaceutical grade amino acid entity (e.g., in weight % of total pharmaceutical grade amino acid entities) at a sampling point differing from the amount of a pharmaceutical grade amino acid entity present in the PGDBP by less than a predetermined amount.

145. The PGDBP of embodiment 143, wherein composition uniformity, e.g., blend uniformity, comprises the amount of the Active Moiety (e.g., one or more pharmaceutical grade amino acid entities of the Active Moiety; e.g., in weight % of total pharmaceutical grade amino acid entities) at a sampling point differing from the amount of the Active Moiety present in the PGDBP by less than a predetermined amount.

146. The PGDBP of either of embodiments 144 or 145, wherein the predetermined amount is 1, 2, 3, 4, 5, 6, 7, 8, 9, or 10%, e.g., of the total amount of the pharmaceutical grade amino acid entity or Active Moiety present in the PGDBP.

147. The PGDBP of embodiment 146, wherein the predetermined amount is 10% of the total amount of the pharmaceutical grade amino acid entity or Active Moiety present in the PGDBP.

148. The PGDBP of any of embodiments 134-147, wherein the amount of a pharmaceutical grade amino acid entity or Active Moiety at one or a plurality of points (e.g., at least 50, 60, 70, 80, 90, 95, or 99% of points) differs by no more than 10% from a reference value.

149. The PGDBP of embodiment 148, wherein the reference value is the total amount of the pharmaceutical grade amino acid entity or Active Moiety present in the combination or PGDBP.

150. The PGDBP of any of embodiments 134-149, wherein the PGDBP is suitable for oral administration.

151. The PGDBP of any of embodiments 134-150, wherein the PGDBP further comprises one or more excipients, e.g., excipients suitable for oral administration.

152. The PGDBP of any of embodiments 134-151, wherein the PGDBP further comprises one or more oral administration components, e.g., flavorants or bitterness masking agents.

153. The PGDBP of any of embodiments 134-152, wherein the PGDBP meets a further reference standard comprising composition uniformity with regards to the one or more excipients and/or oral administration components.

154. The PGDBP of any of embodiments 151-153, wherein the excipient or oral administration component is selected from Table 14.

155. The PGDBP of any of embodiments 151-153, wherein the excipient or oral administration component is selected from the GRAS Notice List provided by the FDA.

156. The PGDBP of any of embodiments 134-155, wherein the PGDBP is not sufficiently sterile for parenteral administration.

157. The PGDBP of any of embodiments 134-156, wherein the level of microbial contamination of the PGDBP is below the level permitted in food.

158. The PGDBP of any of embodiments 134-157, wherein the level of endotoxin contamination of the PGDBP is below the level permitted in food.

159. The PGDBP of any of embodiments 134-157, wherein the level of contamination, e.g., by metals, lecithin, choline, endotoxin, microbes, or other contaminants (e.g., contaminants from raw materials) of the PGDBP is below the level permitted in food.

160. The PGDBP of embodiment 159, wherein the contamination or contaminant is less than 10, 9, 8, 7, 6, 5, 4, 3, 2, 1, 0.1, 0.01, or 0.001% (w/w) of the PGDBP.

161. The PGDBP of embodiment 159, wherein the PGDBP is substantially free of contamination or contaminants.

162. A plurality of portions of a dry blended preparation, e.g., pharmaceutical grade dry blended preparation (PGDBP), comprising at least 4 pharmaceutical grade amino acid entities, e.g., an Active Moiety comprising at least 4 pharmaceutical grade amino acid entities, the plurality having one or more of the following properties:
 a) the plurality comprises at least 10 portions, e.g., at least 10, 50, 100, 200, 300, 400, 500, 600, 700, 800, 900, 1000, 1200, 1400, 1600, 1800, 2000, 3000, 4000, 5000, 6000, 7000, 8000, 9000, 10,000, or more portions;
 b) the PGDBP was made by a method described herein, e.g., a method of any of embodiments 81-131;
 c) each portion is a unit dosage form;
 d) each portion comprises 1 to 50 grams of PGDBP; or
 e) each portion comprises at least 2, 3, 4, 5, 6, 7, 8, 9, 10, 15, 20, 25, 30, 35, 40, 45, 50, 60, 70, 80, 90, 100, 150, 200, 250, 300, 350, 400, 450, or 500 g or 1, 2, 3, 4, or 5 kg of PGDBP.

163. The plurality of embodiment 163, wherein the combination comprises 4, 5, 6, 7, 8, 9, 10, 11, 12, 13, 14, 15, 16, 17, 18, 19, or 20 pharmaceutical grade amino acid entities (e.g., the Active Moiety comprises 4, 5, 6, 7, 8, 9, 10, 11, 12, 13, 14, 15, 16, 17, 18, 19, or 20 pharmaceutical grade amino acid entities).

164. The plurality of either of embodiments 162 or 163, wherein the PGDBP meets a reference standard.

165. The plurality of embodiment 164, wherein the reference standard is set by a manufacturer of the PGDBP.

166. The plurality of embodiment 164, wherein the reference standard is set by a manufacturer having approval from a governmental agency to market the PGDBP.

167. The plurality of embodiment 164, wherein the reference standard is set by a pharmacopeal entity, or a national formulary, or found in a pharmacopeal reference, e.g., the USP or NF.

168. The plurality of embodiment 164, wherein the reference standard is set by a a governmental agency, e.g., a government agency that authorizes or regulates the manufacture or marketing of the PGDBP.

169. The plurality of embodiment 168, wherein the government agency comprises one or more of the following agencies: Federal Drug Administration (FDA), European Medicines Agency (EMA), SwissMedic, China Food and Drug Administration (CFDA), or Japanese Pharmaceuticals and Medical Devices Agency (PMDA), Health Canada, Medicines and Healthcare Products Regulatory Agency (MHRA), or the International Council for Harmonisation of Technical Requirements for Pharmaceuticals for Human Use (ICH).

170. The plurality of any of embodiments 164-169, wherein the plurality of portions of the PGDBP meet the reference standard.

171. The plurality of embodiment 170, wherein at least 50, 60, 70, 80, 90, 95, 99, 99.9, 99.99, or 100% of the portions of the plurality of portions of a PGDBP meet the reference standard.

172. The plurality of either embodiment 170 or 171, wherein the reference standard comprises composition uniformity, e.g., blend uniformity and/or portion uniformity.

173. The plurality of embodiment 172, wherein composition uniformity, e.g., blend uniformity, comprises the amount of a pharmaceutical grade amino acid entity (e.g., in weight % of total pharmaceutical grade amino acid entities) or Active Moiety in a portion differing from the amount of a pharmaceutical grade amino acid entity or Active Moiety present in the PGDBP by less than a predetermined amount.

174. The plurality of embodiment 173, wherein the predetermined amount is 1, 2, 3, 4, 5, 6, 7, 8, 9, or 10%, e.g., of the total amount of the pharmaceutical grade amino acid entity present in the PGDBP.

175. The plurality of embodiment 174, wherein the predetermined amount is 10% of the total amount of the pharmaceutical grade amino acid entity present in the PGDBP.

176. The plurality of embodiment 172, wherein composition uniformity, e.g., portion uniformity, comprises the amount of a pharmaceutical grade amino acid entity in a portion of the plurality of portions differing by no more than 1, 2, 5, or 10% from a reference value.

177. The plurality of embodiment 172, wherein composition uniformity, e.g., portion uniformity, comprises the amount of the Active Moiety, e.g., one or more pharmaceutical grade amino acid entities of the Active Moiety, in a portion of the plurality of portions differing by no more than 1, 2, 5, or 10% from a reference value.

178. The plurality of either of embodiments 176 or 177, wherein composition uniformity, e.g., portion uniformity, comprises differing by no more than 10% from a reference value.

179. The plurality of either of embodiments 176 or 178, wherein the reference value is the amount of the pharmaceutical grade amino acid entity in any other portion of the plurality of portions.

180. The plurality of either of embodiments 177 or 178, wherein the reference value is the amount of the Active Moiety (e.g. the amount of one or more pharmaceutical grade amino acid entities of the Active Moiety) in any other portion of the plurality of portions.

181. The plurality of either of embodiments 176 or 178, wherein the reference value is the average or median amount of the pharmaceutical grade amino acid entity in the portions of the plurality of portions.

182. The plurality of either of embodiments 177 or 178, wherein the reference value is the average or median amount of the Active Moiety (e.g. the amount of one or more pharmaceutical grade amino acid entities of the Active Moiety) in the portions of the plurality of portions.

183. The plurality of any of embodiments 176-178, wherein the plurality of portions comprises a plurality of test portions.

184. The plurality of embodiment 183, wherein the reference value is the average or median amount of the pharmaceutical grade amino acid entity in the plurality of test portions.

185. The plurality of embodiment 183, wherein the reference value is the average or median amount of the Active Moiety (e.g. the amount of one or more pharmaceutical grade amino acid entities of the Active Moiety) in the plurality of test portions.

186. The plurality of any of embodiments 162-185, wherein each portion is a unit dosage disposed in a container suitable for opening and use by an end user.

187. The plurality of any of embodiments 162-186, wherein each portion is suitable for mixing with a liquid.

188. The plurality of any of embodiments 162-187, wherein each portion of the plurality of portions is suitable for oral administration.

189. The plurality of any of embodiments 162-188, wherein each portion of the plurality of portions further comprises one or more oral administration components, e.g., flavorants or bitterness masking agents.

190. The plurality of any of embodiments 162-189, wherein each portion of the plurality of portions further comprises one or more excipients, e.g., excipients suitable for oral administration.

191. The plurality of any of embodiments 162-190, wherein each portion of the plurality of portions is not sufficiently sterile for parenteral administration.

192. The plurality of any of embodiments 162-191, wherein the level of microbial contamination of each portion of the plurality of portions is below the level permitted in food.

193. The plurality of any of embodiments 162-192, wherein the level of endotoxin contamination of each portion of the plurality of portions is below the level permitted in food.

194. The plurality of any of embodiments 162-193, wherein the level of contamination, e.g., by metals, lecithin, choline, endotoxin, microbes, or other contaminants (e.g., contaminants from raw materials) of each portion of the plurality of portions is below the level permitted in food.

195. The plurality of embodiment 194 wherein the contamination or contaminant is less than 10, 9, 8, 7, 6, 5, 4, 3, 2, 1, 0.1, 0.01, or 0.001% (w/w) of each portion of the plurality of portions.

196. The plurality of embodiment 194, wherein each portion of the plurality of portions is substantially free of contamination or contaminants.

197. The plurality of any of embodiments 189-196, wherein the excipient or oral administration component is selected from Table 14.

198. The plurality of any of embodiments 162-197, wherein the portion(s) is formulated as a sachet, stick pack, or in a vial.

199. The plurality of any of embodiments 162-198, wherein the portions are formulated as pharmaceutical compositions.

200. The plurality of any of embodiments 162-199, wherein each portion of the plurality is from the same manufacturing batch.

201. The plurality of any of embodiments 162-200, wherein the plurality comprises at least 10, 50, 100, 200, 300, 400, 500, 600, 700, 800, 900, 1000, 1200, 1400, 1600, 1800, 2000, 3000, 4000, 5000, 6000, 7000, 8000, 9000, 10,000, or more portions.

202. The plurality of any of embodiments 162-201, wherein portions comprise at least 1, 2, 3, 4, 5, 6, 7, 8, 9, 10, 15, 20, 25, 30, 35, 40, 45, 50, 60, 70, 80, 90, 100, 150, 200, 250, 300, 350, 400, 450, or 500 g or 1, 2, 3, 4, or 5 kg, e.g., 1, 2, 3, 4, 5, 6, 7, 8, 9, 10, 15, 20, 25, 30, 35, 40, 45, 50, 60, 70, 80, 90, 100, 150, 200, 250, 300, 350, 400, 450, or 500 g or 1, 2, 3, 4, or 5 kg.

203. A method of manufacturing a plurality of any of embodiments 162-202, comprising:
   providing a portion from the plurality of portions and evaluating whether the portion meets a reference standard, and
   responsive to the evaluation, selecting and/or executing a downstream processing step selected from fill and finish, packaging, labeling, shipping, or release into commerce, for the plurality of portions.

204. A dosage form comprising at least 1, 2, 3, 4, 5, 6, 7, 8, 9, 10, 15, 20, 25, 30, 35, 40, 45, 50, 60, 70, 80, 90, 100, 150, 200, 250, 300, 350, 400, 450, or 500 grams of a dry blended preparation, e.g., pharmaceutical grade dry blended preparation (PGDBP), comprising: at least 4 pharmaceutical grade amino acid entities (e.g., an Active Moiety comprising at least 4 pharmaceutical grade amino acid entities), and at least one excipient, e.g., an oral administration component.

205. A dosage form comprising at least 1, 2, 3, 4, 5, 6, 7, 8, 9, 10, 15, 20, 25, 30, 35, 40, 45, 50, 60, 70, 80, 90, 100, 150, 200, 250, 300, 350, 400, 450, or 500 grams of a PGDBP of any of embodiments 134-161, wherein the dosage form comprises at least one at least one excipient, e.g., an oral administration component.

206. The dosage form of either of embodiments 204 or 205, wherein the PGDBP comprises one or more of histidine, leucine, isoleucine, phenylalanine, arginine, or tryptophan.

207. The dosage form of any of embodiments 204-206, wherein the oral administration component comprises a bitterness masking agent or flavorant.

208. The dosage form of any of embodiments 204-207, made by the method described herein, e.g., a method of any of embodiments 81-131 or 203.

209. The dosage form of any of embodiments 204-208, wherein the PGDBP is made by the method described herein, e.g., a method of embodiments 36-80.

210. The method, PGDBP, plurality, or dosage form of any of preceding embodiment, wherein the PGDBP comprises at least 10, 15, 25, 30, 40, 50, 60, 70, 80, 90, 100, 120, 140, 160, 180, 200, 300, 400, 500, 600, 700, 800, 900, 1000, 2000, 3000, 4000, 5000, 6000, 7000, 8000, 9000, or 10000 kg.

211. The method, PGDBP, plurality, or dosage form of any preceding embodiment, wherein the PGDBP, portions of the plurality, or dosage form does not substantially comprise (e.g., comprises less than 10, 9, 8, 7, 6, 5, 4, 3, 2, 1, 0.1, 0.01, or 0.001% (w/w)) an oral administration component, e.g., does not substantially comprise a tastant, a bitterness covering agent, flavorants, a sweetener, odor masking agent, a wetting agent, a stabilizing/thickening agent, or a coloring agent.

212. The method, PGDBP, plurality, or dosage form of any preceding embodiment, wherein the PGDBP, portions of the plurality, or dosage form does not substantially comprise (e.g., comprises less than 10, 9, 8, 7, 6, 5, 4, 3, 2, 1, 0.1, 0.01, or 0.001% (w/w)) a bitterness covering agent.

213. The method, PGDBP, plurality, or dosage form of any preceding embodiment, wherein the PGDBP, portions of the plurality, or dosage form does not substantially comprise (e.g., comprises less than 10, 9, 8, 7, 6, 5, 4, 3, 2, 1, 0.1, 0.01, or 0.001% (w/w)) a sweetener.

214. The method, PGDBP, plurality, or dosage form of any preceding embodiment, wherein the PGDBP, portions of the plurality, or dosage form does not substantially comprise (e.g., comprises less than 10, 9, 8, 7, 6, 5, 4, 3, 2, 1, 0.1, 0.01, or 0.001% (w/w)) a odor masking agent.

215. The method, PGDBP, plurality, or dosage form of any preceding embodiment, wherein the PGDBP, portions of the plurality, or dosage form does not substantially comprise (e.g., comprises less than 10, 9, 8, 7, 6, 5, 4, 3, 2, 1, 0.1, 0.01, or 0.001% (w/w)) a tastant.

216. The method, PGDBP, plurality, or dosage form of any preceding embodiment, wherein the PGDBP, portions of the plurality, or dosage form does not substantially comprise (e.g., comprises less than 10, 9, 8, 7, 6, 5, 4, 3, 2, 1, 0.1, 0.01, or 0.001% (w/w)) a flavorant.

217. The method, PGDBP, plurality, or dosage form of any preceding embodiment, wherein the PGDBP, portions of the plurality, or dosage form does not substantially comprise (e.g., comprises less than 10, 9, 8, 7, 6, 5, 4, 3, 2, 1, 0.1, 0.01, or 0.001% (w/w)) a wetting agent, e.g., lecithin.

218. The method, PGDBP, plurality, or dosage form of any preceding embodiment, wherein the PGDBP, portions of the plurality, or dosage form does not substantially comprise (e.g., comprises less than 10, 9, 8, 7, 6, 5, 4, 3, 2, 1, 0.1, 0.01, or 0.001% (w/w)) a stabilizing/thickening agent.

219. The method, PGDBP, plurality, or dosage form of any preceding embodiment, wherein the PGDBP, portions of the plurality, or dosage form does not substantially comprise (e.g., comprises less than 10, 9, 8, 7, 6, 5, 4, 3, 2, 1, 0.1, 0.01, or 0.001% (w/w)) a coloring agent.

220. The method, PGDBP, plurality, or dosage form of any preceding embodiment, wherein blending does not effect a transition from a crystalline state to an amorphous state.

221. The method, PGDBP, plurality, or dosage form of any preceding embodiment, wherein blending occurs at a temperature lower than 40° C.

222. The method, PGDBP, plurality, or dosage form of any preceding embodiment, wherein blending comprises blending or mixing in a blender or mixer at a speed of less than 15,000 rpm.

223. The method of any preceding embodiment, wherein the method further comprises performing an additional processing step on the dry blended preparation, e.g., PGDBP.

224. The method of embodiment 223, wherein the processing step is selected from direct blending, roller compaction, and wet granulation.

225. The method, PGDBP, plurality, or dosage form of any preceding embodiment, wherein the dry blended preparation, e.g., PGDBP, comprises:
 a) a leucine amino acid entity,
 b) a arginine amino acid entity,
 c) glutamine amino acid entity; and
 d) a N-acetylcysteine (NAC)-entity.

226. The method, PGDBP, plurality, or dosage form of any preceding embodiment, wherein the reference standard is part of the ICH Impurities in New Drug Substances Q3A guidelines.

227. The method, PGDBP, plurality, or dosage form of any preceding embodiment, wherein the reference standard is that the dry blended preparation, e.g., PGDBP, or plurality of portions of the same comprise a level of a contaminant that is less than 0.15% (w/w).

228. The method, PGDBP, plurality, or dosage form of any preceding embodiment wherein the dry blended preparation, e.g., PGDBP, or plurality of portions of the same comprise a level of a contaminant (e.g., does not substantially comprise a contaminant) that is less than 0.05% (w/w).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3A shows a listing of components of an exemplary combination of amino acid entities and excipients, e.g., PGDBP, with pharmaceutical grade amino acid entities highlighted in green. FIG. 3G shows a graph of conformity index over time where each data point at a given time represents a sample from a different location in the blender, with a shaded oval and arrow highlighting the convergence of the data points at 40 minutes of blending.

FIG. 7A is a graph showing the average amount of amino acid in the 10 SP from the B, M, and E of a batch of a PGDBP. Error bars are standard deviation.

FIG. 8A shows three alignments of NIR spectrographs. Each alignment of spectrographs shows analysis of 6 samples of the combination of amino acid entities (a PGDBP), each taken at the same time point from a different region of the blender (see different lines). The top alignment of spectrographs depicts data from time 0, the second from 5 minutes into blending, and the third after 10 minutes of blending.

FIG. 8B is an overlay of HPLC chromatograms analyzing the amino acid content of 10 ten random samples from a batch of a PGDBP. The peaks are assigned to specific amino acids and the amount of the amino acid present in the random sample can be quantified by integrating to obtain the area under the peak.

FIG. 8C is an overlay of HPLC chromatograms analyzing the amino acid content of 10 ten random samples from a batch of a PGDBP. The peaks are assigned to specific amino acids and the amount of the amino acid present in the random sample can be quantified by integrating to obtain the area under the peak.

FIG. 9B is a graph showing the average amount and standard error of amino acid in 10 random samples from the 25 minute blending time of a PGDBP (the PGDBP of FIG. 9A).

FIG. 10B is a graph showing the average amount and standard error of amino acid in 4 random samples from the 20 minute blending time of a PGDBP (the PGDBP of FIG. 10A).

DETAILED DESCRIPTION

Figure 1:
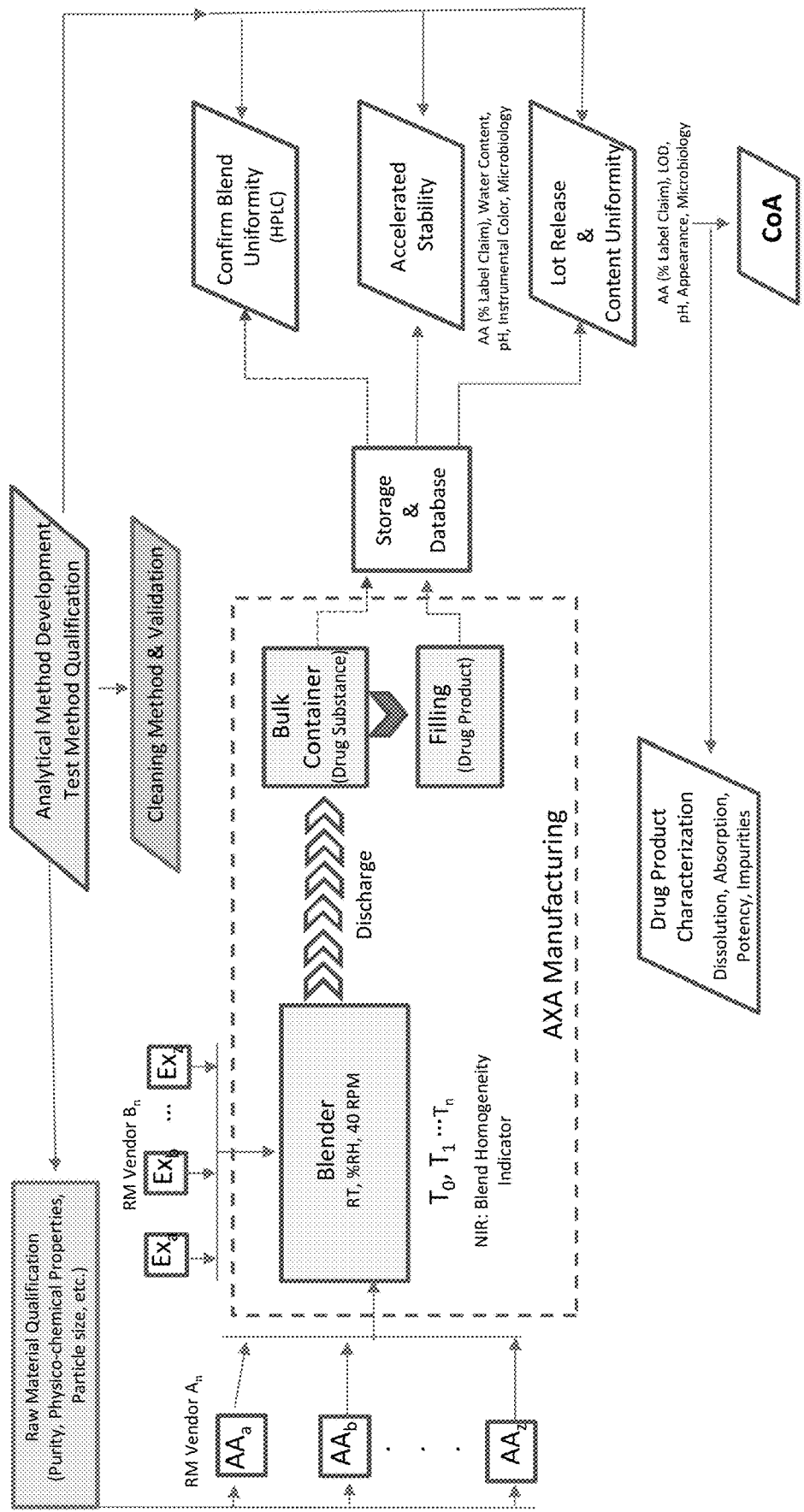
FIG. 1 shows in schematic form an example production method for PGDBP (dotted line box) and steps producing and evaluating dosage forms of a PGDBP.

The present invention provides, at least in part, methods of manufacturing dry blended preparations, e.g., PGDBPs, of a plurality of amino acid entities. The methods comprise blending a combination of amino acid entities in a manner and time sufficient to achieve a standard, e.g., of blend or composition uniformity, e.g., a pharmaceutically acceptable standard.

In some embodiments, the dry blended preparation, e.g., PGDBP, comprises at least four different amino acid entities. In some embodiments, the PGDBP is capable of having a physiological effect, e.g., improving liver function. In some embodiments, the PGDBP is capable of treating or ameliorating one or more of: decreased muscle function due to aging, injury, atrophy, infection, or disease; muscle atrophy; sarcopenia, e.g., cirrhotic sarcopenia; muscle deterioration; muscle decay; cachexia; drug-induced myopathy; muscular dystrophy; myopenia; traumatic brain injury (TBI); chronic traumatic encephalopathy; decreased neuronal signaling; increased inflammation of brain tissue; increased microglial response to pro-inflammatory signals; decreased ionic flux; decreased mitochondrial function; TCA cycle anaplerosis; increased synaptic dysfunction; decreased fat metabolism; hepatocyte apoptosis; hepatocyte ballooning; inflammation of adipose tissue; inflammation of hepatic tissue; fibrosis; liver injury; glucose tolerance; oxidative stress; non-alcoholic fatty liver disease (NAFLD); pediatric NAFLD; steatosis, non-alcoholic steatohepatitis (NASH); fibrosis; immobilization; malnutrition; fasting; aging; autophagy; reduced protein synthesis; anabolic resistance; junction integrity; insulin resistance; decreased mitochondrial biogenesis; decreased myogenesis or myotube growth; end stage liver disease (ESLD); hepatic insufficiency; hyperammonemia; ammonia toxicity; decreased urea synthesis; muscle wasting; ascites; frailty; hepatic encephalopathy; coagulopathy; or an energy deficit.

Definitions

Terms used in the claims and specification are defined as set forth below unless otherwise specified.

It must be noted that, as used in the specification and the appended claims, the singular forms "a," "an" and "the" include plural referents unless the context clearly dictates otherwise.

As used herein, the term "Active Moiety" means a combination comprising four or more amino acid entities, typically pharmaceutical grade amino acid entities, that, in aggregate, have the ability to have a physiological effect as described herein. For example, an Active Moiety can rebalance a metabolic dysfunction in a subject suffering from a disease or disorder. An Active Moiety can contain other biologically active ingredients. In some examples, the Active Moiety comprises a defined combination of four or more amino acid entities, e.g., as set out in detail below. In other embodiments, the Active Moiety consists of a defined combination of amino acid entities, e.g., as set out in detail below. The individual amino acid entities are present in the Active Moiety in various amounts or ratios, which can be described as amount by weight (e.g., in grams), ratio by weight of amino acid moieties to each other, amount by mole, amount by weight percent of the Active Moiety, amount by mole percent of the Active Moiety, caloric content, percent caloric contribution to the Active Moiety, etc. Generally this disclosure will provide grams of amino acid entity in a dosage form, weight percent of an amino acid moiety relative to the weight of the Active Moiety, i.e., the weight of all the amino acid moieties and any other biologically active ingredient present in the Active Moiety, or in ratios. Typically, Active Moieties do not include, or are substantially free of, whey, casein, lactalbumin, and other proteins, e.g., intact proteins found in nutritional supplement or enteric preparations. In some embodiments, Active Moieties do not include hydrolyzed or intact forms of whey, casein, lactalbumin, and other proteins, e.g., proteins found in nutritional supplements.

As used herein, the term "amino acid entity" refers to an amino acid in one or both of free form or salt form, an amino acid residue of a peptide (e.g., of a dipeptide, oligopeptide, or polypeptide), a derivative of an amino acid, a precursor of an amino acid, or a metabolite of an amino acid. In some embodiments, an amino acid entity is no more than 20 amino acids long.

As used herein the term "XXX amino acid entity" refers to an amino acid entity that if a free amino acid, comprises free XXX or XXX in salt form; if a peptide, refers to a peptide comprising an XXX residue; if a derivative, refers to a derivative of XXX; if a precursor, refers to a precursor of XXX; and if a metabolite, refers to a XXX metabolite. An XXX metabolite or XXX derivative can be a metabolite or derivative capable of affecting the biological functionality of the free XXX, e.g., the L-form of free XXX. In some embodiments, the XXX amino acid entity comprises an L-form of the XXX amino acid. For example, where XXX is leucine (L), then L-amino acid entity refers to free L or L in salt form, a peptide comprising a L residue, a L derivative, a L precursor, or a metabolite of L; where XXX is arginine (R), then R-amino acid entity refers to free R or R in salt form, a peptide comprising a R residue, a R derivative, a R precursor, or a metabolite of R; where XXX is glutamine (Q), then Q-amino acid entity refers to free Q or Q in salt form, a peptide comprising a Q residue, a Q derivative, a Q precursor, or a metabolite of Q; where XXX is N-acetylcysteine (NAC), then NAC-amino acid entity refers to free NAC or NAC in salt form, a peptide comprising a NAC residue, a NAC derivative, a NAC precursor, or a metabolite of NAC; where XXX is histidine (H), then H-amino acid entity refers to free H or H in salt form, a peptide comprising a H residue, a H derivative, a H precursor, or a metabolite of H; where XXX is lysine (K), then K-amino acid entity refers to free K or K in salt form, a peptide comprising a K residue, a K derivative, a K precursor, or a metabolite of K; where XXX is phenylalanine (F), then F-amino acid entity refers to free F or F in salt form, a peptide comprising a F residue, a F derivative, a F precursor, or a metabolite of F; or where XXX is threonine (T), then T-amino acid entity refers to free T or T in salt form, a peptide comprising a T residue, a T derivative, a T precursor, or a metabolite of T.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

An "amino acid" refers to an organic compound having an amino group (—NH$_2$), a carboxylic acid group (—C(=O)OH), and a side chain bonded through a central carbon atom, and includes essential and non-amino acids, as well as natural and unnatural amino acids.

The proteogenic amino acids, shown below, are known by three- and one-letter abbreviations in addition to their full names. For a given amino acid, these abbreviations are used interchangeably herein. For example, Leu, L or leucine all refer to the amino acid leucine; Ile, I or isoleucine all refer to the amino acid isoleucine; Val, V or valine all refer to the amino acid valine; Arg, R or arginine all refer to the amino acid arginine; and Gln, Q or glutamine all refer to the amino acid glutamine. Likewise, the non-natural amino acid derivative N-acetylcysteine may be referred to interchangeably by "NAC" or "N-acetylcysteine." Amino acids may be present as D- or L-isomers. Unless otherwise indicated, amino acids referred to herein are L-isomers of amino acids.

TABLE 1

Amino acid names and abbreviations

| Amino acid | Three-letter | One-letter |
|---|---|---|
| Alanine | Ala | A |
| Arginine | Arg | R |
| Asparagine | Asn | N |
| Aspartic acid | Asp | D |
| Carnitine | Car | |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A "branched chain amino acid" is an amino acid selected from the group consisting of leucine, isoleucine, and valine.

The term "effective amount" as used herein means an amount of an amino acid entity, Active Moiety, or pharmaceutical composition which is sufficient enough to significantly and positively modify the symptoms and/or conditions to be treated (e.g., provide a positive clinical response) or to elicit the desired physiological effect. The effective amount for use in a pharmaceutical composition will vary with the particular condition being treated, the severity of the condition, the duration of treatment, the nature of concurrent therapy, the desired physiological effect, the particular Active Moiety or amino acid entities being employed, the particular pharmaceutically-acceptable excipient(s) and/or carrier(s) utilized, and like factors with the knowledge and expertise of the attending physician.

A "time sufficient" or "sufficient time" as used herein in the context of blending means a time sufficient to achieve blend and composition uniformity without generating impurities or inducing heterogeneity.

A dry blended preparation (a DBP), as used herein, means a combination of a plurality of amino acid entities that substantially lacks water. In some embodiments, a dry blended preparation is a powder. In some embodiments, a dry blended preparation comprises less than or equal to 10, 9, 8, 7, 6, 5, 4, 3, 2, or 1% water by weight. In some embodiments, a dry blended preparation comprises at least 4 amino acid entities, e.g., 4, 5, 6, 7, 8, 9, 10, 11, 12, 13, 14, 15, 16, 17, 18, 19, or 20 amino acid entities.

A dry blended preparation, e.g., PGDBP, described herein may be formulated as a "pharmaceutical composition". A pharmaceutical composition as described herein comprises at least one amino acid entity, e.g., an Active Moiety, and a pharmaceutically acceptable carrier or excipient. In some embodiments, the pharmaceutical composition is used as a therapeutic or a medical food. In some embodiments, the pharmaceutical composition is used as a nutriceutical or as a supplement.

The term "pharmaceutical grade" as used herein, refers to amino acids, materials, excipients, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments, pharmaceutical grade means that the amino acids, materials, or excipients meet the specifications of a monograph, e.g., a monograph of the United States Pharmacopeia (USP), the National Formulary (NF), British Pharmacopeia (BP), European Pharmacopeia (EP), or Japanese Pharmacopeia (JP) detailing tests and acceptance criteria. In some embodiments, the meaning of pharmaceutical grade comprises that the amino acids, excipients, or materials are at least 99% pure.

A pharmaceutical grade dry blended preparation (PGDBP), as used herein, is a dry blended preparation that meets a reference standard (e.g., one or more reference standards) and comprises a plurality of pharmaceutical grade amino acid entities. A PGDBP may be formulated as a pharmaceutical composition, e.g., the PGDBP may further comprise one or more excipients and/or oral administration components. In some embodiments, a reference standard met by a PGDBP is composition uniformity.

A reference standard, as used herein, means: a standard used or set by:

(1) a manufacturer of a combination (e.g., dry blended preparation, e.g., PGDBP), e.g., a manufacturer having approval from a governmental agency to market the PGDBP, or (2) the pharmaceutical industry or agencies or entities (e.g., government or trade agencies or entities) regulating the pharmaceutical industry, to ensure one or more product quality parameters are within acceptable ranges for a medicine, pharmaceutical composition, treatment, or other therapeutic. A product quality parameter can be any parameter regulated by the manufacturer, pharmaceutical industry or by agencies or entities, e.g., government or trade agencies or entities, including but not limited to composition; composition uniformity; dosage; dosage uniformity; presence, absence, and/or level of contaminants or impurities; and level of sterility (e.g., the presence, absence and/or level of microbes). Exemplary government regulatory agencies include: Federal Drug Administration (FDA), European Medicines Agency (EMA), SwissMedic, China Food and Drug Administration (CFDA), or Japanese Pharmaceuticals and Medical Devices Agency (PMDA), Health Canada, and Medicines and Healthcare Products Regulatory Agency (MHRA). A product quality parameter can also be a parameter specified by a national or regional pharmacopeia or formulary, including the U.S. Pharmacopeia (USP), British Pharmacopeia (BP), National Formulary (NF), European Pharmacopeia (EP), or Japanese Pharmacopeia (JP).

Composition uniformity, as used herein, is a standard for the homogeneity of a component of a combination, e.g., a dry blended preparation, e.g., a PGDBP, that comprises blend uniformity, portion uniformity, or both. In some embodiments, a combination meets a standard for composition uniformity, e.g., blend uniformity, if the amount of a component (e.g., a pharmaceutical grade amino acid entity, excipient, or oral administration component) at a sampling point in the combination differs from a reference value by less than a predetermined amount. In some embodiments, the reference value is the amount of the component at a second sampling point in the combination. In some embodiments, the reference value is the amount of the component (e.g., a pharmaceutical grade amino acid entity, excipient, or oral administration component) present in the combination (e.g., a dry blended preparation, e.g., a PGDBP).

In some embodiments, wherein a combination (e.g., a dry blended preparation, e.g., a PGDBP) is divided into portions, the portions of the combination meet a standard for composition uniformity, e.g., portion uniformity, if the amount of a component (e.g., a pharmaceutical grade amino acid entity, excipient, or oral administration component) in a portion differs from a reference value by less than a predetermined amount. In some embodiments, the reference value is the amount of the component in a second portion. In some embodiments, the reference value comprises the amount of the component in a N additional portions, wherein in is at least 2, 3, 4, 5, 6, 7, 8, 9, 10, 20, 30, 40, 50, 60, 70, 80, 90, or 100. In some embodiments, the reference value is the amount of the component (e.g., a pharmaceutical grade amino acid entity, excipient, or oral administration component) present in the combination (e.g., a dry blended preparation, e.g., a PGDBP). Amounts may be absolute (e.g., mass or weight) or relative (e.g., percent of total components). In some embodiments, the predetermined amount may be 20, 19, 18, 17, 16, 15, 14, 13, 12, 11, 10, 9, 8, 7, 6, 5, 4, 3, 2, or 1%, e.g., of the reference value. In some embodiments, the predetermined amount is 10% (e.g., the amount of the component differs from the reference value by less than 10%).

A composition, formulation or product is "therapeutic" if it provides a beneficial clinical effect, i.e., a therapeutic effect, when administered to a subject, e.g., patient. A beneficial clinical effect, i.e., therapeutic effect, may comprise lessening the progression of a disease or condition and/or alleviating one or more symptoms of the disease or condition. A beneficial clinical effect, i.e., therapeutic effect, may comprise lessening or alleviating side effects associated with another therapy.

A "unit dose" or "unit dosage" as used herein means an amount or dose of medicine prepared in an individual packet or container for convenience, safety, or monitoring. A "unit dose" or "unit dosage" comprises the drug product or drug products in the form in which they are marketed for use, with a specific mixture of active ingredients and inactive components (excipients), in a particular configuration (such as a capsule shell, for example), and apportioned into a particular dose.

A "stick pack" as used herein means a flexible disposable or single use container comprising a unit dosage of PGDBP. In some embodiments, the container is plastic, paper, or thermoplastic polymer resin, e.g., tearable plastic, paper, or thermoplastic polymer resin. In some embodiments, a stick pack comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, or 60 g of PGDBP.

Portioning, as used herein, means dividing all or part of the dry blended preparation, e.g., PGDBP, into portions for administration to a patient or subject. The portions created by portioning may be provided in sachets, vials, or other containers, e.g., stick packs. In one embodiment, the portions created by portioning are unit dosage amounts, e.g., one unit dosage or a fraction of a unit dosage (e.g., a stick pack may comprise half a unit dose, such that two stick packs would be used together to provide a single unit dose). In some embodiments, only PGDBPs (e.g., that meet a reference standard) are separated into portions via portioning. In some embodiments, portions generated by portioning also meet a reference standard.

As used herein, the terms "treat," "treating," or "treatment" refer in one embodiment, to ameliorating, e.g., decreased muscle function (e.g., relative to a health subject), a muscle disease, or a muscle disorder (i.e., slowing or arresting or reducing the development of the disease or disorder or at least one of the clinical symptoms thereof). In another embodiment, "treat," "treating," or "treatment" refers to alleviating or ameliorating at least one physical parameter including those which may not be discernible by the patient. In yet another embodiment, "treat," "treating," or "treatment" refers to modulating a symptom of decreased muscle function (e.g., relative to a health subject), a muscle disease, or a muscle disorder, either physically, (e.g., stabilization of a discernible symptom), physiologically, (e.g., stabilization of a physical parameter), or both. In yet another embodiment, "treat," "treating," or "treatment" refers to preventing or delaying the onset or development or progression of decreased muscle function (e.g., relative to a health subject), a muscle disease, or a muscle disorder.

Compositions Comprising Amino Acid Entities

It has been discovered that mixtures of amino acids and related molecules (e.g., combinations, e.g., dry blended preparations, e.g., PGDBPs, of the present disclosure) can treat various disease states by rebalancing patients' metabolic state to address serious unmet medical needs. These endogenous metabolic modulators treat the multifactorial etiology of serious diseases by reprogramming disordered metabolism in an unprecedented, coordinated, multifactorial manner.

For example, in a four-week muscle atrophy study, a composition of ten amino acids entities, including branched chain amino acids, some essential amino acids, glutamine, arginine, and N-acetyl cysteine (NAC), demonstrated robust effects in attenuating muscle atrophy during one week of limb immobilization (U.S. patent application Ser. No. 15/847,343). This unique composition also demonstrated improved muscle health and strength, even with a brief recovery period following immobilization, and favorably impacted systemic inflammation by simultaneously boosting anti-inflammatory cytokines while suppressing pro-inflammatory mediators. In some embodiments, the methods described herein can be used to produce PGDBPs comprising the amino acid entities described in U.S. patent application Ser. No. 15/847,343, which is hereby incorporated by reference in its entirety. In some embodiments, the PGDBPs, plurality of portions of PGDBPs, or dosage forms described herein comprise the mixtures of amino acid entities described in U.S. patent application Ser. No. 15/847,343.

Another composition, comprising the branched chain amino acids, arginine, glutamine, and NAC, produced clinically meaningful improvements in the overall metabolic profile of patients, including the lowering of hepatic steatosis by simultaneously impacting multiple drivers of non-alcoholic fatty liver disease (NAFLD) in a study of patients with type 2 diabetes and NAFLD (see U.S. patent application Ser. No. 15/847,289). Administration of the composition also increased markers of insulin sensitivity, decreased lipotoxicity, decreased the level of markers of inflammation and apoptosis, and suppressed fibrogenic markers. In some embodiments, the methods described herein can be used to produce PGDBPs comprising the amino acid entities described in U.S. patent application Ser. No. 15/847,289, which is hereby incorporated by reference in its entirety. In some embodiments, the PGDBPs, plurality of portions of PGDBPs, or dosage forms described herein comprise the mixtures of amino acid entities described in U.S. patent application Ser. No. 15/847,289.

The present disclosure provides compositions, e.g., dry blended preparations, e.g., PGDBPs, comprising amino acid entities. These compositions are made up of pharmaceutical grade amino acid entities including amino acids in one or both of free form or salt form, amino acid residues of a peptide (e.g., of a dipeptide, oligopeptide, or polypeptide), derivatives of an amino acid, precursors of an amino acid, or metabolites of an amino acid. In some embodiments, the compositions can include one or more amino acid entities from Table 2. In some embodiments, the compositions can include a leucine (L)-amino acid entity. In some embodiments, the compositions can include an isoleucine (L)-amino acid entity. In some embodiments, the compositions can include a valine (L)-amino acid entity. In some embodiments, the compositions can include an arginine (L)-amino acid entity. In some embodiments, the compositions can include a glutamine (L)-amino acid entity. In some embodiments, the compositions can include a N-acetylcysteine (L)-amino acid entity. In some embodiments, the compositions can include a histidine (L)-amino acid entity. In some embodiments, the compositions can include a lysine (L)-amino acid entity. In some embodiments, the compositions can include a phenylalanine (L)-amino acid entity. In some embodiments, the compositions can include a threonine (L)-amino acid entity. In some embodiments, the compositions can include a serine (L)-amino acid entity. In some embodiments, the compositions can include a tryptophan (L)-amino acid entity. In some embodiments, the compositions can include a carnitine (L)-amino acid entity. For example, the compositions can include a leucine (L)-amino acid entity, an arginine (R)-amino acid entity, a glutamine (Q)-amino acid entity; and an antioxidant or reactive oxygen species (ROS) scavenger, e.g., a N-acetylcysteine (NAC) entity, e.g., NAC (Table 2). In particular, at least one amino acid entity is not a peptide of more than 20 amino acid residues in length. In some embodiments, all amino acid entities in the composition, e.g., dry blended preparation, e.g., PGDBP, are no more than 20 amino acid residues in length.

TABLE 2

Amino acid entities include amino acids, precursors, metabolites, and derivatives of the compositions described herein.

| | Exemplary Amino Acid | Precursors | Metabolites | Derivatives |
|---|---|---|---|---|
| L | L-Leucine | Oxo-leucine | HMB (beta-hydroxy-beta-methylbutyrate); Oxo-leucine; Isovaleryl-CoA | D-Leucine; N-Acetyl-Leucine |
| I | L-Isoleucine | 2-Oxo-3-methyl-valerate; Threonine | 2-Oxo-3-methyl-valerate; Methylbutyrl-CoA | D-Isoleucine; N-Acetyl-Isoleucine |
| V | L-Valine | 2-Oxo-valerate | Isobutryl-CoA; | N-Acetyl-Valine |
| R | L-Arginine | Argininosuccinate; Citrulline; Aspartate; Glutamate | Ornithine; Citrulline; Agmatine; Creatine | D-Arginine; N-Acetyl-Arginine; |
| Q | L-Glutamine | Glutamate | Carbamoyl-P; Glutamate | D-Glutamine; N-Acetyl-Glutamine; |
| NAC | N-Acetylcysteine | Serine; Acetylserine; Cystathionine; | Glutathione; Cystathionine; Homocysteine; Methionine | D-Cysteine; L-Cysteine; Cystine; Cysteamine |
| H | L-Histidine | Histidinol; Histidinal; Ribose-5-phosphate | Carnosine; Histamine; Urocanate | D-Histidine; N-Acetyl-Histidine |
| K | L-Lysine | Diaminopimelate; Aspartate | Trimethyllysine; Carnitine; Saccharopine | D-Lysine; N-Acetyl-Lysine |
| F | L-Phenylalanine | Phenylpyruvate | Tyrosine | D-Phenylalanine; N-Acetyl-Phenylalanine |
| T | L-Threonine | Homoserine; O-PhosphoHomoserine | Oxobutyrate | D-Threonine; N-Acetyl-Threonine |
| S | L-Serine | Phosphoserine, P-hydroxypyruvate, L-Glycine | Glycine, Tryptophan, Acetylserine, Cystathionine, Phosphatidylserine | |
| W | L-Tryptophan | | | |
| Car | L-Carnitine | 6-N-trimethyllysine; N6-Trimethyl-3-OH-lysine | | Acetyl-L-Carnitine (ALCAR); Proprionyl-L-Carnitine (PLCAR); L-Carnitine L-Tartrate |

An exemplary dry blended preparation, e.g., PGDBP, includes leucine, isoleucine, valine, arginine HCl, glutamine, N-acetylcysteine, histidine, lysine, phenylalanine, and threonine as its defined amino acid components in a wt. ratio of 2.0:1.0:1.0:3.62:2.66:0.3:0.16:0.7:0.16:0.34 (Table 3). The dry blended preparation, e.g., PGDBP, includes leucine, isoleucine, valine, arginine, glutamine, N-acetylcysteine, histidine, lysine, phenylalanine, and threonine as its defined amino acid components in a wt. ratio of 2.0:1.0:1.0:3.0:2.66:0.3:0.16:0.7:0.16:0.34.

TABLE 3

Exemplary amino acid components of the composition.

| Amino acid | weight ratio | g/packet | g/dose 1 | Total g daily dose 1 | g/dose 2 | Total g daily dose 2 |
|---|---|---|---|---|---|---|
| Leucine | 2.0 | 1.0 | 1.0 | 3 | 4 | 12 |
| Isoleucine | 1.0 | 0.5 | 0.5 | 1.5 | 2 | 6 |
| Valine | 1.0 | 0.5 | 0.5 | 1.5 | 2 | 6 |
| Arginine HCl | 3.62 | 1.81 | 1.81 | 5.43 | 7.24 | 21.72 |
| Glutamine | 2.66 | 1.33 | 1.33 | 3.99 | 5.32 | 15.96 |
| N-acetylcysteine | 0.3 | 0.15 | 0.15 | 0.45 | 0.6 | 1.8 |
| Histidine | 0.16 | 0.08 | 0.08 | 0.24 | 0.32 | 0.96 |
| Lysine | 0.7 | 0.35 | 0.35 | 1.05 | 1.4 | 4.2 |
| Phenylalanine | 0.16 | 0.08 | 0.08 | 0.24 | 0.32 | 0.96 |
| Threonine | 0.34 | 0.17 | 0.17 | 0.51 | 0.68 | 2.04 |
| Total amino acids | | ~6 g | ~6 g | ~18 g | ~24 g | ~72 g |

An exemplary Amino Acid Composition includes leucine, isoleucine, valine, arginine HCl, glutamine, and N-acetylcysteine as its amino acid entities in a wt. ratio of 1:0.5:0.5:1.81:2:0.15 (Table 4). An exemplary dry blended preparation, e.g., PGDBP, includes leucine, isoleucine, valine, arginine, glutamine, and N-acetylcysteine as its amino acid entities in a wt. ratio of 1:0.5:0.5:1.5:2:0.15 (Table 5).

TABLE 4

Exemplary amino acid components of the composition including Arginine HCl.

| Amino acid | wt. ratio | wt. % | g/packet | g dose #1 | g dose #2 |
|---|---|---|---|---|---|
| Leucine | 1 | 16.78 | 1.00 g | 2 g | 4 g |
| Isoleucine | 0.5 | 8.39 | 0.50 g | 1 g | 2 g |
| Valine | 0.5 | 8.39 | 0.50 g | 1 g | 2 g |
| Arginine HCl | 1.81 | 30.37 | 1.81 g | 3.62 g | 7.24 g |
| Glutamine | 2 | 33.56 | 2.00 g | 4 g | 8 g |
| N-acetylcysteine | 0.15 | 2.52 | 0.15 g | 0.3 g | 0.6 g |
| Total amino acids | | | 5.96 g | ~12 g | ~24 g |

TABLE 5

Exemplary amino acid components of the composition including Arginine.

| Amino acid | wt. ratio | wt. % | g/packet | g dose #1 | g dose #2 |
|---|---|---|---|---|---|
| Leucine | 1 | 17.70 | 1.00 g | 2 | 4 |
| Isoleucine | 0.5 | 8.85 | 0.50 g | 1 | 2 |
| Valine | 0.5 | 8.85 | 0.50 g | 1 | 2 |
| Arginine | 1.5 | 26.55 | 1.5 g | 3 | 6 |
| Glutamine | 2 | 35.4 | 2.00 g | 4 | 8 |
| N-acetylcysteine | 0.15 | 2.65 | 0.15 g | 0.3 | 0.6 |
| Total amino acids | | | 5.65 g | 11.3 g | 22.6 g |

An exemplary dry blended preparation, e.g., PGDBP, includes leucine, isoleucine, valine, arginine HCl, glutamine, and N-acetylcysteine as its amino acid entities in a wt. ratio of 1:0.5:0.5:0.905:2:0.15 (Table 6). An exemplary dry blended preparation, e.g., PGDBP, includes leucine, isoleucine, valine, arginine, glutamine, and N-acetylcysteine as its amino acid entities in a wt. ratio of 1:0.5:0.5:0.75:2:0.15 (Table 7).

TABLE 6

Exemplary amino acid components of the composition including Arginine HCl.

| Amino acid | wt. ratio | wt. % | g/packet | g dose #1 | g dose #2 |
|---|---|---|---|---|---|
| Leucine | 1 | 19.78 | 1.00 g | 2 g | 4 g |
| Isoleucine | 0.5 | 9.89 | 0.50 g | 1 g | 2 g |
| Valine | 0.5 | 9.89 | 0.50 g | 1 g | 2 g |
| Arginine HCl | 0.905 | 17.90 | 0.905 g | 1.81 g | 3.62 g |
| Glutamine | 2 | 39.56 | 2.00 g | 4 g | 8 g |
| N-acetylcysteine | 0.15 | 2.97 | 0.15 g | 0.3 g | 0.6 g |
| Total amino acids | | | 5.06 g | ~10 g | ~20 g |

TABLE 7

Exemplary amino acid components of the composition including Arginine.

| Amino acid | wt. ratio | wt. % | g/packet | g dose #1 | g dose #2 |
|---|---|---|---|---|---|
| Leucine | 1 | 20.41 | 1.00 g | 2 | 4 |
| Isoleucine | 0.5 | 10.20 | 0.50 g | 1 | 2 |
| Valine | 0.5 | 10.20 | 0.50 g | 1 | 2 |
| Arginine | 0.75 | 15.31 | 0.75 g | 1.5 | 3 |
| Glutamine | 2 | 40.82 | 2.00 g | 4 | 8 |
| N-acetylcysteine | 0.15 | 3.06 | 0.15 g | 0.3 | 0.6 |
| Total amino acids | | | 4.9 g | 9.8 g | 19.6 g |

An exemplary dry blended preparation, e.g., PGDBP, includes leucine, isoleucine, valine, arginine HCl, glutamine, and N-acetylcysteine as its amino acid entities in a wt. ratio of 1:0.5:0.25:0.905:1:0.225 (Table 8). An exemplary dry blended preparation, e.g., PGDBP, includes leucine, isoleucine, valine, arginine, glutamine, and N-acetylcysteine as its amino acid entities in a wt. ratio of 1:0.5:0.25:0.75:1:0.225 (Table 9).

TABLE 8

Exemplary amino acid components of the composition including Arginine HCl.

| Amino acid | wt. ratio | wt. % | g/packet | g dose #1 | g dose #2 |
|---|---|---|---|---|---|
| Leucine | 1 | 25.77 | 1.00 g | 2 g | 4 g |
| Isoleucine | 0.5 | 12.89 | 0.50 g | 1 g | 2 g |
| Valine | 0.25 | 6.44 | 0.25 g | 0.50 g | 1 g |
| Arginine HCl | 0.905 | 23.32 | 0.905 g | 1.81 g | 3.62 g |
| Glutamine | 1 | 25.77 | 1.00 g | 2 g | 4 g |

TABLE 8-continued

Exemplary amino acid components
of the composition including Arginine HCl.

| Amino acid | wt. ratio | wt. % | g/packet | g dose #1 | g dose #2 |
|---|---|---|---|---|---|
| N-acetylcysteine | 0.225 | 5.80 | 0.225 g | 0.45 g | 0.9 g |
| Total amino acids | | | 3.88 g | 7.76 g | 15.52 g |

TABLE 9

Exemplary amino acid
components of the composition including Arginine.

| Amino acid | wt. ratio | wt. % | g/packet | g dose #1 | g dose #2 |
|---|---|---|---|---|---|
| Leucine | 1 | 26.85 | 1.00 g | 2 | 4 |
| Isoleucine | 0.5 | 13.42 | 0.50 g | 1 | 2 |
| Valine | 0.25 | 6.71 | 0.25 g | 0.5 | 1 |
| Arginine | 0.75 | 20.13 | 0.75 g | 1.5 | 3 |
| Glutamine | 1 | 26.85 | 1.00 g | 2 | 4 |
| N-acetylcysteine | 0.225 | 6.04 | 0.225 g | 0.45 | 0.9 |
| Total amino acids | | | 3.725 g | 7.45 g | 14.9 g |

An exemplary dry blended preparation, e.g., PGDBP, includes leucine, isoleucine, valine, arginine HCl, glutamine, N-acetylcysteine, and serine as its amino acid entities in a wt. ratio of 1:0.5:0.25:0.905:1:0.225:0.667 (Table 10). An exemplary dry blended preparation, e.g., PGDBP, includes leucine, isoleucine, valine, arginine, glutamine, N-acetylcysteine, and serine as its amino acid entities in a wt. ratio of 1:0.5:0.25:0.75:1:0.225:1.5 (Table 11).

TABLE 10

Exemplary amino acid
components of the composition including Arginine HCl.

| Amino acid | wt. ratio | wt. % | g/packet | g dose #1 | g dose #2 |
|---|---|---|---|---|---|
| Leucine | 1 | 18.59 | 1.00 g | 2 g | 4 g |
| Isoleucine | 0.5 | 9.29 | 0.50 g | 1 g | 2 g |
| Valine | 0.25 | 4.65 | 0.25 g | 0.50 g | 1 g |
| Arginine HCl | 0.905 | 16.82 | 0.905 g | 1.81 g | 3.62 g |
| Glutamine | 1 | 18.59 | 1.00 g | 2 g | 4 g |
| N-acetylcysteine | 0.225 | 4.18 | 0.225 g | 0.45 g | 0.9 g |
| Serine | 1.5 | 27.88 | 1.5 | 3 | 6 |
| Total amino acids | | | 5.38 g | 10.76 g | 21.52 g |

TABLE 11

Exemplary amino acid
components of the composition including Arginine.

| Amino acid | wt. ratio | wt. % | g/packet | g dose #1 | g dose #2 |
|---|---|---|---|---|---|
| Leucine | 1 | 19.14 | 1.00 g | 2 | 4 |
| Isoleucine | 0.5 | 9.57 | 0.50 g | 1 | 2 |
| Valine | 0.25 | 4.78 | 0.25 g | 0.5 | 1 |
| Arginine | 0.75 | 14.35 | 0.75 g | 1.5 | 3 |
| Glutamine | 1 | 19.14 | 1.00 g | 2 | 4 |
| N-acetylcysteine | 0.225 | 4.31 | 0.225 g | 0.45 | 0.9 |
| Serine | 1.5 | 28.71 | 1.5 | 3 | 6 |
| Total amino acids | | | 5.225 | 10.45 | 20.9 |

An exemplary dry blended preparation, e.g., PGDBP, includes leucine, isoleucine, valine, arginine HCl, glutamine, N-acetylcysteine, and serine as its amino acid entities in a wt. ratio of 1:0.5:0.25:0.905:1:0.225:0.667 (Table 12). An exemplary dry blended preparation, e.g., PGDBP, includes leucine, isoleucine, valine, arginine, glutamine, N-acetylcysteine, and serine as its amino acid entities in a wt. ratio of 1:0.5:0.25:0.75:1:0.225:1.667 (Table 13).

TABLE 12

Exemplary amino acid
components of the composition including Arginine HCl.

| Amino acid | wt. ratio | wt. % | g/packet | g dose #1 | g dose #2 |
|---|---|---|---|---|---|
| Leucine | 1 | 18.02 | 1.00 g | 2 g | 4 g |
| Isoleucine | 0.5 | 9.01 | 0.50 g | 1 g | 2 g |
| Valine | 0.25 | 4.50 | 0.25 g | 0.50 g | 1 g |
| Arginine HCl | 0.905 | 16.31 | 0.905 g | 1.81 g | 3.62 g |
| Glutamine | 1 | 18.02 | 1.00 g | 2 g | 4 g |
| N-acetylcysteine | 0.225 | 4.05 | 0.225 g | 0.45 g | 0.9 g |
| Serine | 1.667 | 30.09 | 1.67 g | 3.33 g | 6.67 g |
| Total amino acids | | | 5.55 g | 11.09 g | 22.19 g |

TABLE 13

Exemplary amino acid
components of the composition including Arginine.

| Amino acid | wt. ratio | wt. % | g/packet | g dose #1 | g dose #2 |
|---|---|---|---|---|---|
| Leucine | 1 | 18.54 | 1.00 g | 2 | 4 |
| Isoleucine | 0.5 | 9.27 | 0.50 g | 1 | 2 |
| Valine | 0.25 | 4.64 | 0.25 g | 0.5 | 1 |
| Arginine | 0.75 | 13.91 | 0.75 g | 1.5 | 3 |
| Glutamine | 1 | 18.54 | 1.00 g | 2 | 4 |
| N-acetylcysteine | 0.225 | 4.17 | 0.225 g | 0.45 | 0.9 |
| Serine | 1.667 | 30.92 | 1.67 g | 3.33 g | 6.67 g |
| Total amino acids | | | 5.395 g | 10.78 g | 21.57 g |

An exemplary dry blended preparation, e.g., PGDBP, includes leucine, isoleucine, arginine HCl, glutamine, serine, carnitine, and N-acetylcysteine as its amino acid entities in a wt. ratio of 1:0.5:1.6124:0.6667:2.5:0.3333:0.4333 (Table 14).

TABLE 14

Exemplary amino acid components of the composition.

| Amino acid | wt. ratio | wt. % | g/packet | g dose #1 | g dose #2 |
|---|---|---|---|---|---|
| Leucine | 1.0000 | 13.45 | 1.00 g | 4.0000 | 6.0000 |
| Isoleucine | 0.5000 | 6.72 | 0.50 g | 2.0000 | 3.0000 |
| Arginine | 1.6124 | 21.68 | 1.6124 g | 6.4496 | 9.6744 |
| Glutamine | 0.6667 | 8.97 | 0.6667 g | 2.6666 | 4.0000 |
| Serine | 2.5000 | 33.62 | 2.50 g | 10.0000 | 15.0000 |
| Carnitine | 0.3333 | 4.48 | 0.3333 g | 1.3333 | 2.0000 |
| N-acetylcysteine | 0.4333 | 5.83 | 0.4333 g | 1.7333 | 2.6000 |

An exemplary dry blended preparation, e.g., PGDBP, includes leucine, isoleucine, valine, lysine, histidine, threonine, and ornithine-aspartate as its amino acid entities in a wt. ratio of 0.8889:0.4444:0.8889:0.4703:0.3333:0.3333:1.6667 (Table 15).

TABLE 15

Exemplary amino acid components of the composition.

| Amino acid | wt. ratio | wt. % | g/packet | g dose #1 | g dose #2 |
|---|---|---|---|---|---|
| Leucine | 0.8889 | 15.06 | 0.8889 g | 2.6667 | 8.0000 |
| Isoleucine | 0.4444 | 7.53 | 0.4444 g | 1.3333 | 4.0000 |

TABLE 15-continued

Exemplary amino acid components of the composition.

| Amino acid | wt. ratio | wt. % | g/packet | g dose #1 | g dose #2 |
|---|---|---|---|---|---|
| Valine | 0.8889 | 15.06 | 0.8889 g | 2.6667 | 8.0000 |
| Lysine | 0.4703 | 7.97 | 0.4703 g | 1.4108 | 4.2323 |
| Histidine | 0.3333 | 5.65 | 0.3333 g | 1.0000 | 3.0000 |
| Threonine | 0.3333 | 5.65 | 0.3333 g | 1.0000 | 3.0000 |
| Ornithine-Aspartate | 1.6667 | 28.23 | 1.6667 g | 5.0000 | 15.0000 |

An exemplary dry blended preparation, e.g., PGDBP, includes leucine, valine, arginine, glutamine, N-acetylcysteine, serine, carnitine, histidine, lysine, and citrulline as its amino acid entities in a wt. ratio of 3.0:1.0:6.0:5.0:1.3:2.5:1.0:1.0:1.5:4.0 (Table 16).

TABLE 16

Exemplary amino acid components of the composition.

| Amino acid | wt. ratio | wt. % | g/packet | g dose #1 |
|---|---|---|---|---|
| Leucine | 3.0 | 11.4 | 1.00 | 6.0 |
| Valine | 1.0 | 3.8 | 0.33 | 2.0 |
| Arginine | 6.0 | 22.8 | 2.00 | 12.0 |
| Glutamine | 5.0 | 19.0 | 1.67 | 10.0 |
| N-acetylcysteine | 1.3 | 4.9 | 0.43 | 2.6 |
| Serine | 2.5 | 9.5 | 0.83 | 5.0 |
| Carnitine | 1.0 | 3.8 | 0.33 | 2.0 |
| Histidine | 1.0 | 3.8 | 0.33 | 2.0 |
| Lysine | 1.5 | 5.7 | 0.50 | 3.0 |
| Citrulline | 4.0 | 15.2 | 1.33 | 8.0 |

Production of Dry Blended Preparations

The methods disclosed herein may be used to manufacture dry blended preparations (e.g., PGDBPs) of pharmaceutical grade amino acids. Amino acids used to make the dry blended preparations may be agglomerated, and/or instantized to aid in dispersal and/or solubilization. In some embodiments, the amino acids used to make the dry blended preparations are not instantized and/or are substantially free of lecithin.

The dry blended preparations of the present disclosure may be made using amino acids and amino acid derivatives from the following sources, or other sources may used: e.g., FUSI-BCAA™ Instantized Blend (L-Leucine, L-Isoleucine and L-Valine in 2:1:1 weight ratio), FUSIL™ Instantized L-Leucine, L-Arginine HCl, L-Glutamine and other amino acids may be obtained from Ajinomoto Co., Inc; N-acetylcysteine may be obtained from Spectrum Chemical.

To produce the dry blended preparations of the instant disclosure, the following general steps may be used: individual pharmaceutical grade amino acid entities (and, optionally, one or more excipients and/or oral administration components), may be combined into a combination and subjected to one or more blending conditions (e.g., blending and mixing). In some embodiments, the blending conditions are continued until the combination meets one or more reference standards. In some embodiments, the resulting PGDBP is divided into a plurality of portions. In some embodiments, at least a percentage of the portions of the plurality of portions also meet one or more reference standards, e.g., the reference standards that the PGDBP met. In some embodiments, at least a percentage of the portions of the plurality of portions meet one or more reference standards.

In some embodiments, the dry blended preparation, e.g., PGDBP, is also a large-scale preparation. Large-scale, as used herein, describes a preparation that is larger (e.g., by weight, mass, or volume) than a reference value. In some embodiments, the reference value is the size of a typical experimental (e.g., non-manufacturing) preparation. In some embodiments, the reference value is 10, 11, 12, 13, 14, or 15 kg. In some embodiments, large-scale preparations comprise at least 25, 30, 40, 50, 60, 70, 80, 90, 100, 120, 140, 160, 180, 200, 300, 400, 500, 600, 700, 800, 900, 1000, 2000, 3000, 4000, 5000, 6000, 7000, 8000, 9000, or 10000 kg. In some embodiments, large-scale preparations comprise no more than 10000, 5000, 1000, 900, 800, 700, 600, 500, 400, or 300 kg. In some embodiments, a large-scale preparation comprises 100-500 kg, 100-400 kg, 100-300, 100-200 kg, 200-300 kg, 200-400 kg, 200-500 kg, 300-400 kg, 300-500 kg, 400-500, or 500-1000 kg.

Blending Techniques

The methods disclosed herein comprise blending steps which blend and mix combinations of pharmaceutical grade amino acid entities to create PGDBPs that meet a reference standard. Blending conditions used by the methods described herein may utilize any known blending mechanism or combination of blending mechanisms. Blending mechanisms include convection, diffusion, and shear. Convective blending utilizes gross motion of particles, e.g., by gentle rotation within a blender/mixer. Diffusion is the slow, passive blending of particles. Shear blending pushes part of a combination of particles in one direction and another part of the combination of particles in another direction along the same parallel plane. Blending conditions used by the methods described herein may further comprise the use of granulators or other equipment to modify the size and/or shape of particles of combination components (e.g., pharmaceutical grade amino acid entities).

In some embodiments, the blending or blending condition employed by a method disclosed herein does not effect a transition from a crystalline state (e.g., a mixture of discrete separate crystals) to an amorphous state (e.g., a fine amorphous uniform powder). In some embodiments, less than 0.01, 0.1, 0.5, 1, 2, 10, or 20% (and optionally, 0%) by weight of at least 1, 2, 3, or 4 (e.g., all) of the pharmaceutical grade amino acid entities, or less than 0.01, 0.1, 0.5, 1, 2, 10, or 20% (and optionally, 0%) by weight of the Active Moiety, transforms from a crystalline state to an amorphous state during blending, e.g., less than 10% of the Active Moiety transforms from a crystalline state to an amorphous state during blending. In some embodiments, at least 50, 60, 70, 80, 90, 95, 99, or 100% by weight of at least 1, 2, 3, or 4 (e.g., all) of the pharmaceutical grade amino acid entities, or at least 50, 60, 70, 80, 90, 95, 99, or 100% by weight of the Active Moiety, is in a crystalline state (e.g., a non-amorphous state) during blending. In some embodiments, less than 0.01, 0.1, 0.5, 1, 2, 10, or 20% (and optionally, 0%) by weight of at least 1, 2, 3, or 4 (e.g., all) of the pharmaceutical grade amino acid entities, or less than 0.01, 0.1, 0.5, 1, 2, 10, or 20% (and optionally, 0%) by weight of the Active Moiety, transforms from a crystalline state to an amorphous state during blending, e.g., less than 10% of the Active Moiety transforms from a crystalline state to an amorphous state after blending. In some embodiments, at least 50, 60, 70, 80, 90, 95, 99, or 100% by weight of at least 1, 2, 3, or 4 (e.g., all) of the pharmaceutical grade amino acid entities, or at least 50, 60, 70, 80, 90, 95, 99, or 100% by weight of the Active Moiety, is in a crystalline state (e.g., a non-amorphous state) after blending. In some embodiments, the blending or blending condition employed by a method disclosed herein comprises convective blending. In some embodiments, the blending or blending condition employed by a method disclosed herein comprises diffusion blending. In some embodiments, the blending or blending condition employed by a method disclosed herein comprises shear blending. In some embodiments, the blending or blending condition employed by a method disclosed herein comprises convective and diffusion blending. In some embodiments, the blending or blending condition employed by a method disclosed herein comprises convective and shear blending. In some embodiments, the blending or blending condition employed by a method disclosed herein comprises diffusion and shear blending. In some embodiments, the blending or blending condition employed by a method disclosed herein comprises convective, diffusion, and shear blending.

In some embodiments, a method further comprises a processing step comprising direct blending, roller compaction, or wet granulation. In some embodiments, a method comprises a processing step comprising automated filling, e.g., which incorporates direct blending, roller compaction, or wet granulation.

Blending conditions used by the methods described herein may utilize any known blending or mixing equipment; blending or mixing equipment may operate based on one or more blending mechanisms. There are four main types of blending or mixing equipment: convective, hoppers (i.e., gravimetric), tumblers, and fluidization. In some embodiments, a blending condition or blending step of a method described herein may utilize one or more (e.g., 1, 2, 3, or 4) types of blending or mixing equipment. In some embodiments, dry blended preparations (e.g., PGDBPs) are prepared in batches. In some embodiments, dry blended preparations (e.g., PGDBPs) are prepared in a continuous fashion, e.g., harvesting blended/mixed preparation without interrupting blending or mixing.

Tumbler blenders typically utilize a rotating barrel or chamber (e.g., with speeds of 5-50 revolutions/min.), mixing particles in batches using convective and diffusion blending. Tumbler blenders come in double-cone or V-shaped configurations, which may be symmetrical or asymmetrical. Tumbler blenders are typically utilized in batch mode (i.e., not continuous, i.e., the blender must be stopped to harvest the batch). In some embodiments, a blender comprising a tumbler functionality (e.g., a tumbler blender) that is used in a blending or mixing step of a method described herein is used at a speed of 5, 6, 7, 8, 9, 10, 11, 12, 13, 14, 15, 16, 17, 18, 19, 20, 21, 22, 23, 24, 25, 30, 35, 40, 45, or 50 revolutions/min.

Convective blenders typically comprise a fixed shell with a rotating element (e.g., an agitator, impeller, blade, ribbon, paddle, plow, etc.). Rotating elements may be of a variety of shapes and orientations known in the art. The rotating element rapidly moves particles in the combination from location to location. Convective blenders are typically capable of continuous operation (i.e., harvest and blending may be conducted at the same time); an advantage of continuous operation is that it typically lowers segregation of particles during harvest. Subclasses of convective blenders or blenders comprising convective functionality that may be used in the methods described herein include, but are not limited to: ribbon blenders, orbiting screw blenders, planetary blenders, forberg blenders, horizontal high intensity mixers, horizontal double arm blenders, and vertical high intensity mixer. In some embodiments, a blender comprising a convective functionality (e.g., a convective blender) that is used in a blending or mixing step of a method described herein is used at a variable impeller rotation rate. In some embodiments, a blender comprising a convective functionality (e.g., a convective blender) that is used in a blending or mixing step of a method described herein comprises multiple impeller blades. In some embodiments, a blender comprising a convective functionality (e.g., a convective blender) that is used in a blending or mixing step of a method described herein comprises impeller blades at variable angles. In some embodiments, a blender comprising a convective functionality (e.g., a convective blender) that is used in a blending or mixing step of a method described herein comprises multiple impellers or agitators.

Hopper blenders, also known as gravimetric blenders, typically comprise conical and/or cylindrical containers, sometimes containing other cone/tube structures (e.g., cone-in-cone to tube), with particles pulled down by gravity and mixed as they fall and collide with one another and the surfaces and openings of the cone/tube structures. Each pass of the combination of particles through the hopper mixes the combination further. Hoppers can typically accommodate larger volumes of material than convective or tumbler blenders.

Fluidization mixers mix combinations of solid particles by bubbling gases through the combination. In some embodiments, a bed of solid particles (e.g., particles of one or more pharmaceutical grade amino acid entities) rests atop a porous air distributor. The velocity of the gas pumped through the air distributor required to fluidize the particles on the bed depends on the properties of the particles in the bed. The gas can be heated or cooled to alter the combination's temperature. In some embodiments, a mixer comprising a fluidization functionality (e.g., a fluidization mixer) that is used in a blending or mixing step of a method described herein is utilized with a variable gas flow velocity.

Mixers and blenders may utilize multiple equipment modalities or mechanisms. In some embodiments, the blending or blending condition employed by a method disclosed herein comprises the functionality of a tumbler blender, e.g., a V blender or double-cone blender. In some embodiments, the blending or blending condition employed by a method disclosed herein comprises the functionality of a convective blender, e.g., a ribbon blender. In some embodiments, the blending or blending condition employed by a method disclosed herein comprises the functionality of a hopper blender. In some embodiments, the blending or blending condition employed by a method disclosed herein comprises the functionality of a fluidization mixer. In some embodiments, the blending or blending condition employed by a method disclosed herein comprises the functionality of a tumbler blender and a convective blender. In some embodiments, the blending or blending condition employed by a method disclosed herein comprises the functionality of a tumbler blender and a hopper blender. In some embodiments, the blending or blending condition employed by a method disclosed herein comprises the functionality of a tumbler blender and a fluidization blender. In some embodiments, the blending or blending condition employed by a method disclosed herein comprises the functionality of a convective blender and a hopper blender. In some embodiments, the blending or blending condition employed by a method disclosed herein comprises the functionality of a convective blender and a fluidization mixer. In some embodiments, the blending or blending condition employed by a method disclosed herein comprises the functionality of a hopper blender and a fluidization mixer. In some embodiments, the blending or blending condition employed by a method disclosed herein comprises the functionality of a convective blender, a hopper blender, and a tumbler blender. In some embodiments, the blending or blending condition employed by a method disclosed herein comprises the functionality of a fluidization mixer, a hopper blender, and a tumbler blender. In some embodiments, the blending or blending condition employed by a method disclosed herein comprises the functionality of a convective blender, a fluidization mixer, and a tumbler blender. In some embodiments, the blending or blending condition employed by a method disclosed herein comprises the functionality of a convective blender, a hopper blender, and a fluidization mixer. In some embodiments, the blending or blending condition employed by a method disclosed herein comprises the functionality of a convective blender, a hopper blender, a tumbler blender, and a fluidization mixer.

The blending or mixing steps of methods disclosed herein are of duration sufficient to produce a dry blended preparation, e.g., PGDBP, which meets a reference standard. In some embodiments, the duration of the blending condition is at least 10, 15, 20, 25, 30, 35, 40, 45, 50, 55, 60, 75, 90, 105, or 120 minutes. In some embodiments, the duration of the blending condition is no more than 180, 165, 150, 135, 120, 105, 90, 75, 60, 55, 50, 45, 40, 35, 30, 25, or 20 minutes. In some embodiments, the duration of the blending condition is 20-90, 20-60, 20-50, 20-40, 20-30, 30-90, 30-60, 30-50, 30-40, 40-90, 40-60, 40-50, 50-90, 50-60, or 60-90 minutes. In some embodiments, the duration of the blending condition is 20-40 minutes, e.g., 20 minutes, 30 minutes, or 40 minutes. In some embodiments, the duration of the blending condition is sufficient that blending and mixing does not introduce heterogeneity into the combination or dry blended preparation, e.g., by over-mixing. In some embodiments, the duration of the blending condition is determined by evaluation of whether a reference standard has been met. For example, the blending condition may continue until an evaluation shows that the reference standard has been met. In some embodiments wherein the reference standard is composition uniformity, e.g., blend uniformity, evaluating whether a reference standard has been met comprises using near infrared spectroscopy (NIR). In an embodiment, the blending condition is maintained until the NIR spectrum observed shows that a standard for composition uniformity, e.g., blend uniformity, has been met.

In some embodiments, the blending or blending condition employed by a method disclosed herein does not effect a transition from a crystalline state (e.g., a mixture of discrete separate crystals) to an amorphous state (e.g., a fine amorphous uniform powder). In some embodiments, the methods disclosed herein comprise blending steps which blend and mix combinations of pharmaceutical grade amino acid entities to create PGDBPs, wherein the blending steps occur at room temperature, e.g., from 15 to 30° C., e.g., from 20 to 30° C., e.g., at about 25° C. In some embodiments, the blending steps occur at a temperature lower than 16, 17, 18, 19, 20, 21, 22, 23, 24, 25, 26, 27, 28, 29, 30, 31, 32, 33, 34, 35, 36, 37, 38, 39, or 40° C., e.g., lower than 40° C. (and optionally, at a temperature of at least 5, 6, 7, 8, 9, 10, 11, 12, 13, 14, 15, 16, 17, 18, 19, 20, 21, 22, 23, 24, or 25° C.). In some embodiments, the blending steps occur at a temperature of about 15, 16, 17, 18, 19, 20, 21, 22, 23, 24, 25, 26, 27, 28, 29, or 30° C. Without wishing to be bound by theory, it is thought that mixtures of discrete crystals, e.g., of amino acid entities, may transform into fine amorphous powder mixtures under blending/mixing conditions above 40° C.

In some embodiments, the methods disclosed herein comprise blending steps which blend and mix combinations of pharmaceutical grade amino acid entities to create PGDBPs, wherein the blending steps comprise use of a blender or mixer rotation speed (e.g., a blender or mixer rotor rotational speed) of less than 15,000, 14,000, 13,000, 12,000, 11,000, 10,000, 9,000, 8,000, 7,000, 6,000, 5,000, 4,000, 3,000, 2,000, 1,000, 500, 250, 100, 90, 80, 70, 60, 50, 40, 30, 20, or 10 rotations per minute (rpm) (and optionally, at least 5, 10, 15, 20, 25, 30, 35, 40, 45, 50, 60, 70, 80, 90, or 100 rpm). In some embodiments, the blending steps comprise use of a blender or mixer rotation speed (e.g., a blender or mixer rotor rotational speed) of about 20, 30, 40, 50, 60, 70, 80, 90, or 100 rpm. In some embodiments, the blending steps comprise use of a blender or mixer rotation speed (e.g., a blender or mixer rotor rotational speed) of between 5-50, 5-45, 5-40, 5-35, 5-30, 5-25, 5-20, 5-15, 5-10, 10-50, 10-45, 10-40, 10-35, 10-30, 10-25, 10-20, 10-15, 15-50, 15-45, 15-40, 15-35, 15-30, 15-25, 15-20, 20-50, 20-45, 20-40, 20-35, 20-30, 20-25, 25-50, 25-45, 25-40, 25-35, 25-30, 30-50, 30-45, 30-40, 30-35, 35-50, 35-45, 35-40, 40-50, 40-45, or 45-50 rpm.

Segregation

Segregation of different species of particles in a combination (e.g., dry blended preparation, e.g., PGDBP) during blending or mixing, division of portions, or downstream processing is a barrier to meeting and maintaining reference standards, e.g., a standard of composition uniformity. Any mixture of two or more types of particles can be vulnerable to segregation. Segregation can occur by one or more of several mechanisms, including sifting, fluidization, and dusting. Sifting is the movement of smaller particles through a matrix of larger particles. An example of sifting is the settling of fine particles at the center of a bin and the movement of coarser particles to the periphery. For sifting to occur significantly, a combination must comprise particles of different sizes, the mean particle size must be above a certain level (e.g., see Purutyan, H, and Carson, J. W. *Predicting, diagnosing, and solving mixture segregation problems*. Jenike & Johnson, CSC Publishing, Powder and Bulk Engineering, 2013), the particles must be free-flowing (e.g., no significant agglomeration of particles occurs), and particles must be moving or capable of moving at different velocities with respect to each other. Fluidization, which can be a mechanism for blending and mixing, can also be a mechanism for segregation. Fluidization comprises moving gas through solid particles to cause the solid particles to take on fluid-like properties. Sometimes, finer particles can float to the top of the fluid-like particles. When the combination of particles deaerates, larger or denser particles (or both) can settle to the bottom more quickly than finer particles because the finer particles retain the gas more, resulting in segregation. Dusting involves lighter particles being more readily suspended by currents of air than heavier particles, causing lighter particles to scatter based on air currents and heavier particles to settle. An example of dusting is the scattering of fine particles to the periphery of a container or farther from the incoming source of particles than coarser particles.

In some embodiments, the methods described herein comprise steps preventing or mitigating segregation, e.g., by further blending or mixing. In some embodiments, the methods described herein comprise steps preventing or mitigating segregation by sifting. In some embodiments, the methods described herein comprise steps preventing or mitigating segregation by fluidization, e.g., deaeration. In some embodiments, the methods described herein comprise steps preventing or mitigating segregation by dusting. In some embodiments, the methods described herein comprise steps preventing or mitigating segregation by one or more of sifting, fluidization (e.g., deaeration), or dusting. In some embodiments, segregation does not significantly occur during the methods described herein. In some embodiments, segregation does not significantly occur during downstream processing steps of the method described herein. In some embodiments, segregation does not significantly occur for the duration of the useful shelf life of a dosage form of a PGDBP described herein.

Methods of evaluating the segregation potential of a combination of dry particles, e.g., dry blended preparation (e.g., PGDBP), are known in the art. In some embodiments, the methods described herein further comprise evaluating the segregation potential of a dry blended preparation, e.g., PGDBP. In some embodiments, the methods further comprise, responsive to the evaluation of segregation potential, selecting and/or executing a step preventing, reversing, or mitigating segregation, e.g., selecting and using a blending or mixing technique or blending condition.

Sampling and Measurement

The methods described herein for manufacturing a dry blended preparation, e.g., a PGDBP, that meets a reference standard may further comprise evaluating whether the reference standard has been met. In some embodiments, the methods described herein comprise acquiring a value, e.g., for the amount of a pharmaceutical grade amino acid entity, from one or more sampling points in a dry blended preparation, e.g., PGDBP. A sampling point is a location, e.g., defined spatially and temporally, within a dry blended preparation, e.g., PGDBP. In some embodiments, to acquire a value, a sampling point may be accessed. Accessing a sampling point may comprise using a diagnostic technique on the dry blended preparation of the sampling point. In some embodiments, accessing, e.g., using a diagnostic technique, comprises stopping or pausing the blending or mixing or blending condition to access the sampling point. In some embodiments, accessing, e.g., using a diagnostic technique, does not comprise stopping or pausing the blending or mixing or blending condition to access the sampling point. Sampling points may be designated and/or accessed by methods known in the art.

In some embodiments, accessing a sampling point comprises removing dry blended preparation at a sampling point by using a sample thief, e.g., a metal rod with one or more recessed cavities for retaining the dry blended preparation at the sampling point. Using a sample thief may disturb the blending, mixing, or blending condition. Different components of a combination, e.g., dry blended preparation, may adhere to the sample thief with greater affinity than other components, and operator technique can influence the results obtained from analyzing samples from a sample thief. In some embodiments, accessing a sampling point comprises acquiring a sample from the sampling point, e.g., using a sample thief. In some embodiments, accessing a sampling point comprises acquiring multiple (e.g., 2, 3, 4, 5, 6, 7, 8, 9, or 10) samples, e.g., using a sample thief, from the same sampling point. In the same embodiment, acquiring a value (e.g., for the amount of a pharmaceutical grade amino acid entity) at a sampling point may comprise evaluating a plurality, e.g., all, of the samples taken from a sampling point, e.g., using statistical methods known in the art. In some embodiments, multiple samples from spatially separated sampling points are collected at the same time point (e.g., within a minute of each other or during the same brief pause in blending, mixing, or the blending condition). For example, samples can be collected from a set of predetermined, spread out spatial locations, e.g., a stratified sampling plan with predetermined sites to be sampled, e.g., to obtain samples that represent a variety of locations in the blender or mixer.

In some embodiments, samples acquired from a sampling point of a combination or dry blended preparation (e.g., PGDBP) or portions of a dry blended preparation (e.g., PGDBP) may be analyzed using near-infrared (NIR) spectroscopy to acquire a value (e.g., for composition uniformity, e.g., blend uniformity). NIR spectroscopy analyzes the absorption spectra of compounds in the NIR wavelength region (780-2500 nm). Absorption peaks of compounds, e.g., pharmaceutical grade amino acid entities, are produced by molecular vibrations classified into two types: overtones and combinations. Compounds comprising CH, OH, or NH bonds can be analyzed using NIR. Methods of interpreting NIR spectra are known in the art. In some embodiments, NIR spectroscopy is used to determine whether the amounts of amino acid entities at a plurality of sampling points are similar, e.g., whether a standard for homogeneity (e.g., composition uniformity, e.g., blend uniformity) has been met. In some embodiments, the methods further comprise, responsive to the the determination, selecting and/or executing a step, e.g., selecting and using a blending or mixing technique or blending condition or ending blending, mixing, or a blending condition.

In some embodiments, samples acquired from a sampling point of a combination or dry blended preparation (e.g., PGDBP) or portions of a dry blended preparation (e.g., PGDBP) may be analyzed using high performance liquid chromatography (HPLC, also referred to as high-pressure liquid chromatography) to acquire a value (e.g., for the amount of a pharmaceutical grade amino acid entity). HPLC techniques involve passing a liquid or dissolved sample over chromatographic reagents (e.g., suspended or attached to substrates, e.g., in columns) under high pressures, wherein the chromatographic reagents have differential affinity for components of the sample, allowing for the retention or elution of select components and their subsequent or simultaneous analysis. Many chromatographic reagents are known and readily available in the art. Many types of suitable HPLC equipment and protocols are also known and readily available in the art. In some embodiments, a sample acquired from a sampling point of a combination or dry blended preparation (e.g., PGDBP) or a portion of a dry blended preparation (e.g., PGDBP) is dissolved in a suitable liquid solvent prior to HPLC analysis. In some embodiments, HPLC is used to determine the identity and/or amounts of pharmaceutical grade amino acid entities present at a sampling point or in a portion. Determining the identity and/or amounts of pharmaceutical grade amino acids present can comprise identifying a peak on a chromatogram and integrating the area under the peak. The determination may comprise derivatizing the pharmaceutical grade amino acid entities of the sample, e.g., to make them easier to separate, detect, and/or quantify. Derivatizing groups include fluorophores, chromophores, and groups that modify the elution or retention of the amino acid entity. Exemplary derivatives include ortho-phthalaldehyde (OPA), 9-fluorenylmethyl chloroformate (FMOC), and 6-aminoquinolyl-N-hydroxysuccinimidyl carbamate (AQC) (i.e., AccQ-Tag™ (Waters)) (e.g., used in conjunction with the ChemStation, Open Lab, or Empower software packages). Further derivatives and methods of derivatizing amino acids and analyzing derivatized amino acids are known in the art (e.g., as provided by Agilent Technologies or Waters). In some embodiments, HPLC is used to determine whether a dry blended preparation, e.g., PGDBP, or a plurality of portions of a PGDBP meets a standard for composition uniformity, e.g., portion or blend uniformity. In some embodiments, the methods further comprise, responsive to the amount(s) of pharmaceutical grade amino acid entities present or to the determination, selecting and/or executing a step, e.g., selecting and using a blending or mixing technique or blending condition or ending blending, mixing, or a blending condition.

In some embodiments, samples acquired from a sampling point of a combination or dry blended preparation (e.g., PGDBP) or portions of a dry blended preparation (e.g., PGDBP) may be analyzed using liquid chromatography mass spectrometry (LC-MS). LC-MS comprises separating components of a solution using a chromatographic step and then analyzing the components using mass spectrometry to identify and quantify the amount of the component that is present. Many techniques and equipment setups for LC-MS are available in the art, including techniques and equipment setups suitable for the detection and quantification of the amounts of the pharmaceutical grade amino acid entities present in a combination, dry blended preparation, or PGDBP described herein. In some embodiments, LC-MS is used to determine the identity and/or amounts of pharmaceutical grade amino acid entities present at a sampling point or in a portion. In some embodiments, LC-MS is used to determine whether a dry blended preparation meets a standard for composition uniformity, e.g., portion or blend uniformity. In some embodiments, the methods further comprise, responsive to the amount(s) of pharmaceutical grade amino acid entities present, selecting and/or executing a step, e.g., selecting and using a blending or mixing technique or blending condition or ending blending, mixing, or a blending condition.

In some embodiments, accessing a sampling point does not comprise removing dry blended preparation at the sampling point. In some embodiments, accessing a sampling point comprises directly analyzing the combination, e.g., dry blended preparation, e.g., PGDBP, at the sampling point, e.g., using a NIR spectroscopy. NIR spectroscopy can be used to analyze a sample of the dry blended preparation during blending or mixing, e.g., while continuously maintaining the blending condition. In some embodiments, this allows for a plurality of sampling points to be monitored over the course of blending or mixing without interrupting blending or mixing. In some embodiments, the methods further comprise, responsive to the amount(s) of pharmaceutical grade amino acid entities present at one or more sampling points, selecting and/or executing a step, e.g., selecting and using a blending or mixing technique or blending condition or ending blending, mixing, or a blending condition.

Reference Standards

The methods described herein produce dry blended preparations, e.g., PGDBPs, which meet one or more reference standards. The one or more reference standards may be a standard used or promulgated by the pharmaceutical industry or by agencies or entities, e.g., government or trade agencies or entities, regulating the pharmaceutical industry to ensure one or more product quality parameters are within acceptable ranges for a medicine, pharmaceutical composition, treatment, or other therapeutic. The one or more reference standards may be a standard used or set by a manufacturer of a combination (e.g., dry blended preparation, e.g., PGDBP), e.g., a manufacturer having approval from a governmental agency to market the PGDBP, to ensure one or more product quality parameters are within acceptable ranges for a supplement, nutriceutical, medicine, pharmaceutical composition, treatment, or other therapeutic. A product quality parameter can be any parameter regulated by the manufacturer, or by the pharmaceutical industry or by agencies or entities, e.g., government or trade agencies or entities, including but not limited to composition; composition uniformity; dosage; dosage uniformity; presence, absence, and/or level of contaminants or impurities; level of sterility (e.g., the presence, absence and/or level of microbes), color, or particle morphology (e.g., size or shape). Exemplary government regulatory agencies include: Federal Drug Administration (FDA), European Medicines Agency (EMA), SwissMedic, China Food and Drug Administration (CFDA), Japanese Pharmaceuticals and Medical Devices Agency (PMDA), or the International Council for Harmonisation of Technical Requirements for Pharmaceuticals for Human Use (ICH).

Composition Uniformity

In some embodiments, the reference standard is composition uniformity. Composition uniformity, in general, is a standard of homogeneity. Composition uniformity can be classified into two different but related types of uniformity: blend uniformity and portion uniformity (portion uniformity is used interchangeably with content uniformity and dosage uniformity herein). Composition uniformity may comprise one or both types depending on the usage and context. Composition uniformity may comprise a standard of the homogeneity of a combination (e.g., dry blended preparation, e.g., PGDBP) with regards to one or a plurality of components. In some embodiments, a combination that meets a standard for composition uniformity does so with regards to one, two, three, four, or more (e.g., all) components (e.g., pharmaceutical grade amino acid entities).

Blend Uniformity

Blend uniformity refers to the level of homogeneity of the distribution of components in a combination, e.g., dry blended preparation, e.g., PGDBP. In some embodiments, a standard for composition uniformity, e.g., blend uniformity, is met when the amount of a component (e.g., a pharmaceutical grade amino acid entity) at a first sampling point in the combination (e.g., dry blended preparation, e.g., PGDBP) differs by no more than a predetermined amount from a reference value. Amounts may be absolute, e.g., grams, or relative, e.g., weight/weight (e.g., X g of the component in Y g of sampling point). Amounts may be arbitrary values, as in the case of comparing absorbance values to absorbance values or in statistical comparisons of curves, e.g., of spectra. In some embodiments, acquiring a value for blend uniformity comprises assessing a standard for composition uniformity, e.g., blend uniformity, by acquiring a value for the amount of a component at a first sampling point in the combination and comparing it to reference value.

In some embodiments, NIR is used to determine whether the amount of a component (e.g., a pharmaceutical grade amino acid entity) at a first sampling point in the combination (e.g., dry blended preparation, e.g., PGDBP) differs by no more than a predetermined amount from a second or further sampling. Using NIR, the near infrared spectrum for a sampling point can be acquired and compared to the near infrared spectrum for a second or further sampling point (e.g., a third, fourth, fifth, sixth, seventh, eighth, ninth, and/or tenth sampling point) or to the near infrared spectrum for a sample known to meet a reference standard, e.g., a standard for composition uniformity, e.g., blend uniformity. If the comparison shows that the spectra are similar enough to one another, a standard for blend uniformity is met. Similarity of NIR spectra can be evaluated by comparing the conformity index of sampling points. The conformity index is a value generated by the NIR spectra obtained, and the examples of conformity indices described are not an exhaustive list of all possible conformity indices. The conformity index may be the absorbance at a particular wavelength or wavelengths in the near infrared range. The conformity index may be the standard deviation of the average absorbance at a particular wavelength or wavelengths in the near infrared range at a plurality of sampling points. The key characteristic of the conformity index, whichever value is selected, is that the conformity indices of the sampling points accessed converge (in the case of absorbance at particular wavelength) or reduce (in the case of standard deviation) as blending/mixing time increases. For example, the conformity index may be selected to be a wavelength of X nm in the near infrared range. The absorbance at X nm will be measured at a plurality of sampling points at time points during blending. As blending continues, the absorbance at X nm at each sampling point will grow more similar to one another.

In some embodiments, the reference value is the amount of the component at a second or further sampling point (e.g., a third, fourth, fifth, sixth, seventh, eighth, ninth, and/or tenth sampling point) sampling point in the combination (e.g., dry blended preparation, e.g., PGDBP). The second sampling or further sampling point (e.g., a third, fourth, fifth, sixth, seventh, eighth, ninth, and/or tenth sampling point) point may be a different spatial location in the combination, for example, samples can be collected from a set of predetermined, spread out spatial locations, e.g., a stratified sampling plan with predetermined sites to be sampled, e.g., to obtain samples that represent a variety of locations in the blender or mixer.

In some embodiments, the second sampling point is 1, 2, 3, 4, 5, 6, 7, 8, 9, 10, or more minutes after the first sampling point. In some embodiments, multiple sampling points separated in time are taken throughout the process of manufacturing the dry blended preparation (e.g., PGDBP). In some embodiments, the sampling points separated in time are at intervals throughout the process of manufacturing the dry blended preparation (e.g., PGDBP), e.g., every 1, 2, 3, 4, 5, 6, 7, 8, 9, or 10 minutes. In some embodiments, the multiple sampling points are compared to one another (e.g., the most recent sampling points are compared to each other).

In some embodiments, a standard for composition uniformity, e.g., blend uniformity, is met when the amount of the component at a first sampling point differs from the reference value, e.g., the amount of the component at a second or further sampling point (e.g., a third, fourth, fifth, sixth, seventh, eighth, ninth, and/or tenth sampling point) by less than or equal to 1, 2, 3, 4, 5, 6, 7, 8, 9, or 10%, e.g., 10%. In some embodiments, a standard for composition uniformity is met when the amount of a component at a first sampling differs by no more than 10% from the amount of the component at a second or further sampling point (e.g., a third, fourth, fifth, sixth, seventh, eighth, ninth, and/or tenth sampling point). In some embodiments, a standard for composition uniformity is met when the amount of a component at a first sampling differs by no more than 10% from the amount of the component present in the combination (e.g., dry blended preparation, e.g., PGDBP). In some embodiments, a standard for composition uniformity is met when the amount of a component at the most recent sampling point differs by no more than 10% from the amount of the component present at the next most recent sampling point. Values for the amount of a component present at a sampling point can comprise NIR spectra. Comparisons of values for the amount of a component present at a first, second, or further sampling point can comprise comparison of NIR spectra, e.g., overlaying NIR spectra or comparing conformity indices of the first, second, or further sampling points. Blend uniformity can be met when NIR spectra, e.g., conformity indices, reach a threshold of similarity or overlap.

Portion Uniformity

Portion uniformity refers to the homogeneity of portions of the dry blended preparation, e.g., PGDBP, with respect to amounts of components (e.g., pharmaceutical grade amino acid entities). In some embodiments, the methods described herein comprise division of a dry blended preparation (e.g., PGDBP) into a plurality of portions. In some embodiments, a standard for composition uniformity, e.g., portion uniformity, is met when the amount of a component (e.g., a pharmaceutical grade amino acid entity) in a first portion differs by no more than a predetermined amount from a reference value. Amounts may be absolute, e.g., grams, or relative, e.g., weight/weight (e.g., X g of the component in Y g of sampling point). In some embodiments, the amount of a a component (e.g., a pharmaceutical grade amino acid entity) in a first, second, or further portion (e.g., a third, fourth, fifth, sixth, seventh, eighth, ninth, or tenth portion) is determined using HPLC.

In some embodiments, the reference value is the amount of the component in a second portion. In some embodiments, the reference value is the amount(s) of the component in a plurality of portions, e.g., a plurality of test portions (e.g., the first portion is compared to a plurality of test portions). In an embodiment, the reference value is the average or median amount of the component in the plurality of test portions.

In some embodiments, a standard for composition uniformity, e.g., portion uniformity, is met when the amounts of a component (e.g., a pharmaceutical grade amino acid entity) in a plurality of test portions differ by no more than a predetermined amount from a reference value. Amounts may be absolute, e.g., grams, or relative, e.g., weight/weight (e.g., X g of the component in Y g of sampling point). In some embodiments, the reference value is the average or median amount of the component in the plurality of test portions.

In some embodiments, the reference value is the amount of the component in the combination (e.g., dry blended preparation, e.g., PGDBP). For example, the reference value can be overall weight/weight of the component present in the total combination. In some embodiments, evaluating whether a standard for composition uniformity is met comprises comparing a relative amount of a component at a first sampling point (e.g., X g of the component in Y g of sampling point) to the relative amount of the component in the combination (e.g., W g of the component in Z g of combination total); in other words, evaluating the standard for composition uniformity may comprise comparing X/Y to W/Z.

In an embodiment, at least X % of the portions of the plurality of portions of the dry blended preparation (e.g., PGDBP) are test portions, wherein X is 1, 2, 3, 4, 5, 6, 7, 8, 9, 10, 15, 20, 25, 30, 35, 40, 45, or 50. In some embodiments, no more than X % of the portions of the plurality of portions of the dry blended preparation (e.g., PGDBP) are test portions, wherein X is 50, 45, 40, 35, 30, 25, 20, 15, 10, 9, 8, 7, 6, 5, 4, 3, 2, or 1. In an embodiment, test portions are portions compared to a reference value, e.g., one another or the amount of a component present in the dry blended preparation (e.g., PGDBP), to determine whether a reference standard (e.g., for composition uniformity, e.g., portion uniformity) has been met. In some embodiments, a standard for composition uniformity, e.g., portion uniformity, is met when the amount of a component present in at least X % of test portions differs from a reference value by no more than 1, 2, 3, 4, 5, 6, 7, 8, 9, or 10%, wherein X is 50, 60, 70, 80, 85, 90, 95, 99, or 100%, and wherein the reference value is selected from the average amount of the component present in the test portions, the median amount of the component present in the test portions, or the amount of the component present in the dry blended preparation (e.g., PGDBP).

In some embodiments, portions of the dry blended preparation (e.g., PGDBP) may be stick packs or other unit dosage forms.

Level of Contamination

In some embodiments, the reference standard is level of contamination. When combining raw materials, e.g., pharmaceutical grade amino acid entities and/or excipients, into a combination, e.g., dry blended preparation, e.g., PGDBP, contaminants may be present in the combination. A combination, e.g., dry blended preparation, e.g., PGDBP, meets a standard for level of contamination when the combination does not substantially comprise (e.g., comprises less than 10, 9, 8, 7, 6, 5, 4, 3, 2, 1, 0.15, 0.1, 0.05, 0.01, or 0.001% (w/w) of) a contaminant. In some embodiments, a combination, e.g., dry blended preparation, e.g., PGDBP, comprises less than 0.15% (w/w) of a contaminant. In some embodiments, a combination, e.g., dry blended preparation, e.g., PGDBP, comprises less than 0.05% (w/w) of a contaminant. In some embodiments, a combination, e.g., dry blended preparation, e.g., PGDBP, comprises a lower level of a contaminant than the level permissible in food (e.g., as defined by appropriate regulatory organizations known in the art). In some embodiments, a combination, e.g., dry blended preparation, e.g., PGDBP, described in a method herein does not comprise a contaminant. Contaminants include any substance that is not deliberately present in the combination, e.g., dry blended preparation, e.g., PGDBP, (for example, pharmaceutical grade amino acid entities and excipients, e.g., oral administration components, are deliberately present) or any substance that has an unintended negative effect on a product quality parameter of the PGDBP or plurality of portions of PGDBP (e.g., side effects in a subject, decreased potency, decreased stability/shelf life, discoloration, odor, bad taste, bad texture/mouthfeel, or increased segregation of components of the PGDBP). In some embodiments, contaminants include microbes, endotoxins, metals (e.g., heavy metals), residual solvents, raw material impurities, extractables, and/ or leachables. In some embodiments, a combination, e.g., dry blended preparation, e.g., PGDBP, comprises a level of contaminant (e.g., does not substantially comprise a contaminant) that is compliant with a reference standard, e.g., a standard promulgated by an agency known to those of skill in the art or described herein. In some embodiments, a combination, e.g., dry blended preparation, e.g., PGDBP, comprises a level of contaminant (e.g., does not substantially comprise a contaminant) that is compliant with a standard of the ICH, e.g., the ICH Q3A Impurities in New Drug Substances standard.

In some embodiments, the methods described herein further comprise acquiring a value for the level of a contaminant at a sampling point in one or both of the combination or PGDBP. In some embodiments, the methods described herein further comprise acquiring a value for the level of a contaminant at each of a plurality of points in one or both of the combination or PGDBP, or in a test portion (e.g., of the combination or PGDBP). In some embodiments, the methods described herein further comprise acquiring a value for the level of a contaminant in a portion, e.g., a test portion, of the plurality of portions. In some embodiments, responsive to the value for the level of the contaminant, e.g., and determining that a standard for the level of contamination is met, the methods described herein further comprise selecting and executing a downstream processing step, e.g., dividing the PGDBP into portions (e.g., portioning) and fill-finish (e.g., formulation (e.g., with excipients), packaging, and labeling) and distribution. In some embodiments, responsive to the value for the level of the contaminant, e.g., and determining that a standard for the level of contamination is not met, the methods described herein further comprise selecting and executing a different downstream processing step, e.g., purification and/or removal of the contaminant or disposal of the portion, plurality of portions, or PGDBP.

Formulations

The dry blended preparations, e.g., PGDBPs, of the present disclosure may be formulated in a form suitable for oral use. For example, PGDBPs may be formulated in dry form as a powder, e.g., in a sachet, vial, stick pack, tablets, lozenges, hard or soft capsules, or dispersible powder or granules. In other embodiments, PGDBPs may be formulated in liquid form, e.g., as an aqueous or oily suspension, emulsion, syrup, gel pack, or elixir. In some embodiments, the PGDBP formulated in dry form can be dissolved in an appropriate solvent to provide PGDBP formulated in liquid form. In the same embodiment, the PGDBP may be accompanied by instructions for adding the dry PGDBP to liquid. The dry blended preparations, e.g., PGDBPs, of the present disclosure may be formulated in a form suitable for enteral administration (for example via tube feeding).

The dry blended preparations, e.g., PGDBPs, of the present disclosure may be formulated as a dietary composition, e.g., chosen from a medical food, a functional food, a supplement, or a nutriceutical. The dry blended preparation, e.g., PGDBP, can be for use as a dietary composition, e.g., chosen from a medical food, a functional food, a supplement, or a nutriceutical. In some embodiments, the dietary composition is for use in a method comprising administering the composition to a subject. In some embodiments, the PGDBP may be accompanied by instructions for adding the dry or liquid PGDBP to food to provide a dietary composition, e.g., chosen from a medical food, a functional food, a supplement, or a nutriceutical.

In some embodiments, dry blended preparations, e.g., PGDBPs, formulated in any manner described herein may further be provided as a unit dosage, e.g., a unit dosage comprising an effective amount of PGDBP for treating one or more conditions in a subject (e.g., a human subject or a human patient). In some embodiments, the unit dosage is for use in a method of treating a condition or symptom of a condition. In some embodiments, the methods described herein further comprises identifying a subject with a condition and/or administering a unit dosage of a dry blended preparation, e.g., PGDBP, e.g., a PGDBP described herein. In some embodiments, a condition or symptom is selected from: decreased muscle function due to aging, injury, atrophy, infection, or disease; muscle atrophy; sarcopenia, e.g., cirrhotic sarcopenia; muscle deterioration; muscle decay; cachexia; drug-induced myopathy; muscular dystrophy; myopenia; traumatic brain injury (TBI); chronic traumatic encephalopathy; decreased neuronal signaling; increased inflammation of brain tissue; increased microglial response to pro-inflammatory signals; decreased ionic flux; decreased mitochondrial function; TCA cycle anaplerosis; increased synaptic dysfunction; decreased fat metabolism; hepatocyte apoptosis; hepatocyte ballooning; inflammation of adipose tissue; inflammation of hepatic tissue; fibrosis; liver injury;

glucose tolerance; oxidative stress; non-alcoholic fatty liver disease (NAFLD); pediatric NAFLD; steatosis, non-alcoholic steatohepatitis (NASH); fibrosis; immobilization; malnutrition; fasting; aging; autophagy; reduced protein synthesis; anabolic resistance; junction integrity; insulin resistance; decreased mitochondrial biogenesis; decreased myogenesis or myotube growth; end stage liver disease (ESLD); hepatic insufficiency; hyperammonemia; ammonia toxicity; decreased urea synthesis; muscle wasting; ascites; frailty; hepatic encephalopathy; coagulopathy; or an energy deficit.

In some embodiments, the dry blended preparation, e.g., PGDBP, meets a standard for sterility, e.g., a reference standard for sterility. In some embodiments, the standard for sterility is more sterile than the standard of sterility for food. In some embodiments, the standard for sterility is less sterile than the standard of sterility required for parenteral administration.

Excipients

The combinations, e.g., dry blended preparations, e.g., PGDBPs, of the present disclosure may be compounded or formulated with one or more excipients. Non-limiting examples of suitable excipients include a buffering agent, a preservative, a stabilizer, a binder, a compaction agent, a lubricant, a dispersion enhancer, and a disintegration agent. Further examples of excipients can be found in the Federal Drug Administration's Generally Regarded As Safe (GRAS) Notice List. In some embodiments, the combinations, e.g., dry blended preparations, e.g., PGDBPs, of the present disclosure comprise an excipient (e.g., oral administration component) from the FDA's GRAS Notice List. In some embodiments, excipients for use in the methods, PGDBPs, pluralities of portions of PGDBPs, or dosage forms described herein comply with Sections 201(s) and 409 of the US Federal Food, Drug, and Cosmetic Act (FD&C Act).

In some embodiments, the excipient comprises a buffering agent. Non-limiting examples of suitable buffering agents include citric acid, sodium citrate, magnesium carbonate, magnesium bicarbonate, calcium carbonate, and calcium bicarbonate.

In some embodiments, the excipient comprises a preservative. Non-limiting examples of suitable preservatives include antioxidants, such as alpha-tocopherol and ascorbate, and antimicrobials, such as parabens, chlorobutanol, and phenol.

In some embodiments, the combination, e.g., dry blended preparation, e.g., PGDBP, comprises a binder as an excipient. Non-limiting examples of suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, and combinations thereof.

In some embodiments, the combination, e.g., dry blended preparation, e.g., PGDBP, comprises a lubricant as an excipient. Non-limiting examples of suitable lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

In some embodiments, the combination, e.g., dry blended preparation, e.g., PGDBP, comprises a dispersion enhancer as an excipient. Non-limiting examples of suitable dispersants include starch, alginic acid, polyvinylpyrrolidones, guar gum, kaolin, xanthan gum, bentonite, purified wood cellulose, sodium starch glycolate, isoamorphous silicate, and microcrystalline cellulose as high HLB emulsifier surfactants.

In some embodiments, the combination, e.g., dry blended preparation, e.g., PGDBP, comprises a disintegrant as an excipient. In some embodiments, the disintegrant is a non-effervescent disintegrant. Non-limiting examples of suitable non-effervescent disintegrants include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. In some embodiments, the disintegrant is an effervescent disintegrant. Non-limiting examples of suitable effervescent disintegrants include sodium bicarbonate in combination with citric acid, and sodium bicarbonate in combination with tartaric acid.

In some embodiments, the excipient comprises an oral administration component, e.g., tastant, a bitterness covering agent, a flavoring agent, a sweetener, and a coloring agent.

Oral Administration Components

The combinations, e.g., dry blended preparations, e.g., PGDBPs, of the present disclosure may comprise one or more oral administration components. Oral administration components are components that improve or modify a parameter of a combination that is important for effective oral administration (e.g., an oral administration quality (e.g., taste, flavor, aroma, texture, mouth feel, color, etc.). Non-limiting examples of suitable oral administration components include a tastant, a bitterness covering agent, flavorants, a sweetener, odor masking agent, a wetting agent, a stabilizing/thickening agent, and a coloring agent.

In some embodiments, the oral administration component comprises a flavorant. Flavorants can be chosen from synthetic flavor oils and flavoring aromatics; natural oils; extracts from plants, leaves, flowers, and fruits; and combinations thereof. In some embodiments, the flavorant is selected from cinnamon oils; oil of wintergreen; peppermint oils; clover oil; hay oil; anise oil; eucalyptus; vanilla; citrus oil such as lemon oil, orange oil, grape and grapefruit oil; and fruit essences including apple, peach, pear, strawberry, raspberry, cherry, plum, pineapple, and apricot.

In some embodiments, the oral administration component comprises a sweetener. Non-limiting examples of suitable sweeteners include glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; Stevia Rebaudiana (Stevioside); chloro derivatives of sucrose such as sucralose; and sugar alcohols such as sorbitol, mannitol, xylitol, and the like. Also contemplated are hydrogenated starch hydrolysates and the synthetic sweetener 3,6-dihydro-6-methyl-1,2,3-oxathiazin-4-one-2,2-dioxide, particularly the potassium salt (acesulfame-K), and sodium and calcium salts thereof.

In some embodiments, the oral administration component comprises a coloring agent. Non-limiting examples of suitable color agents include food, drug and cosmetic colors (FD&C), drug and cosmetic colors (D&C), and external drug and cosmetic colors (Ext. D&C). The coloring agents can be used as dyes or their corresponding lakes.

In some embodiments, the oral administration component comprises a bitterness modifying agent. The bitterness modifying agent may reduce the bitterness or the perceived bitterness of the PGDBP. In some embodiments, the bitterness modifying agent is a bitterness covering agent, e.g., that increases a non-bitter flavor so that the taste perceived is less bitter. Bitterness covering agents include flavors, acids, sweeteners, and salts. Examples of bitterness modifying agents, e.g., bitterness covering agents, include fenchone, borneol, or isoborneol, menthol, and aspartame.

Particular oral administration components may include one or more of: citric acid, lecithin, (e.g. Alcolec F100), sweeteners (e.g. sucralose, sucralose micronized NF, acesulfame potassium (e.g. Ace-K)), a dispersion enhancer (e.g. xanthan gum (e.g. Ticaxan Rapid-3)), flavorings (e.g. vanilla custard #4306, Nat Orange WONF #1326, lime 865.0032U, and lemon 862.2169U), a bitterness masking agent (e.g. 936.2160U), and natural or artificial colorings (e.g. FD&C Yellow 6). In some embodiments, the oral administration component comprises lecithin. In other embodiments, the dry blended preparation, e.g., PGDBP, does not comprise lecithin, e.g., is substantially free of lecithin.

Formulation Evaluation

In some embodiments, methods described herein further comprise evaluating an oral administration quality of the dry blended preparation, e.g., PGDBP. Oral administration qualities include but are not limited to flavor, taste, after taste, aroma, texture, mouth feel, and color. As used herein, flavor as a quality comprises taste and aroma. In some embodiments, flavor as a quality further comprises texture and/or mouth feel. Flavor is a composite characteristic that describes the sensations associated with a substance in a subject's mouth. In some embodiments, methods described herein further comprise evaluating a flavor of the dry blended preparation, e.g., PGDBP. In some embodiments, the general flavor of the dry blended preparation, e.g., PGDBP, is evaluated. In some embodiments, particular aspects of flavor are evaluated (e.g., bitterness, sweetness, sourness, saltiness, savoriness, metallic notes, or chemical burn). As used herein, taste as a quality comprises the sensations associated with a substance as experienced purely by the tongue/oral cavity, e.g., in the absence of olfactory/retronasal olfaction contribution. After taste comprises the sensations associated with a substance as experienced purely by the tongue/oral cavity after the substance is substantially removed (e.g., by swallowing) from the mouth. As used herein, aroma as a quality comprises the sensations associated with a substance as experienced via olfaction, e.g., including retronasal olfaction. As used herein, texture as a quality comprises a property of a substance (e.g., combination, e.g., dry blended preparation, e.g., PGDBP, e.g., a formulation of a PGDBP described herein) that describes its granularity and consistency. For example, a substance may have a texture that is crumbly, tough, viscous, clumpy, etc. In some embodiments, texture is typically applied to solids, e.g., powders or foods. As used herein, mouthfeel as a quality comprises the touch sensations associated with a substance as experienced by the mouth.

In some embodiments, the dry blended preparation, e.g., PGDBP, is evaluated in dry form, e.g., as a powder. In some embodiments, the dry blended preparation, e.g., PGDBP, is evaluated in liquid form, e.g., as an aqueous or oily suspension, emulsion, syrup, gel pack, or elixir. In some embodiments, the dry blended preparation, e.g., PGDBP, is evaluated in the form of a dietary composition, e.g., chosen from a medical food, a functional food, a supplement, or a nutriceutical.

Many methods of evaluating oral administration qualities are known to those skilled in the art and may be used to evaluate oral administration qualities in the methods described herein.

In some embodiments, evaluating an oral administration quality comprises evaluating the flavor, e.g., taste and/or aroma, of a dry blended preparation, e.g., PGDBP. In some embodiments, evaluating flavor comprises evaluating one, two, three, four, or all of the level of bitterness, sweetness, sourness, saltiness, umami-ness, savoriness, metallic notes, or chemical burn of a dry blended preparation, e.g., PGDBP. Bitterness can be evaluated by an animal preference test, human sensory evaluation (e.g., a group of human tasters evaluating a number of substances, e.g., scoring them relative to the PGDBP), by electronic tongue measurement, by in silico predictive methods (e.g., using software or searchable databases that, based on the structural/chemical features of the components of the PGDBP, predicts the bitterness of the PGDBP), or other methods known in the art.

Excipients, e.g., oral administration components, can modify the oral administration qualities of the dry blended preparation, e.g., PGDBP. In some embodiments, the methods described herein further comprise, responsive to an evaluation of an oral administration quality, the addition or further addition of an excipient, e.g., oral administration component. In some embodiments, the excipient, e.g., oral administration component, added or further added masks or lessens the bitterness of the dry blended preparation, e.g., PGDBP.

TABLE 14

Exemplary Oral Administration Components

| INGREDIENT | GRADE | FUNCTION |
|---|---|---|
| Citric Acid | USP | pH, Flavor |
| Ace-K | NF | Sweetness (rapid onset) |
| Sucralose | NF | Sweetness (slow onset) |
| Lecithin* | FCC | Wetting Agent |
| Xanthan Gum | FCC | Stabilizer/Thickener |
| Vanilla Custard (Art) | GRAS | Aroma |
| Orange (Nat + WONF) | GRAS | 1° flavor |
| Lime (Nat + WONF) | GRAS | 2° flavor |
| Lemon (Nat + Art) | GRAS | 2° flavor |
| Taste Modifier | GRAS | Bitter masker |
| FD&C Yellow No. 6 | USP | Color |

Dosage Regimens

In some embodiments, the dry blended preparation, e.g., PGDBP, is filled into a unit dosage of between about 4 g and about 80 g total amino acids (e.g., per day). In some embodiments, the dry blended preparation, e.g., PGDBP, is filled into a unit dosage of about 5 g to about 15 g, about 10 g to about 20 g, about 20 g to about 40 g, or about 30 g to about 50 g total amino acids. In some embodiments, the dry blended preparation, e.g., PGDBP, is filled into a unit dosage of about 5 g to about 15 g (e.g., about 6 g total amino acids. In an embodiment, the dry blended preparation, e.g., PGDBP, is filled into a unit dosage comprising about 18 g total amino acids. In an embodiment, the dry blended preparation, e.g., PGDBP, is filled into a unit dosage of about 23 g total amino acids. In an embodiment, the dry blended preparation, e.g., PGDBP, is filled into a unit dosage of about 48 g total amino. In an embodiment, the dry blended preparation, e.g., PGDBP, is filled into a unit dosage of about 68 g total amino acids is administered per day. In an embodiment, the dry blended preparation, e.g., PGDBP, is filled into a unit dosage of about 72 g total amino acids. In some embodiments, the dry blended preparation, e.g., PGDBP, is filled into a unit dosage of about 15 g to about 40 g (e.g., about 24 g total amino acids).

Downstream Processing

The methods of the present disclosure may comprise downstream processing steps, including moving the dry blended preparation, e.g., PGDBP, to one or more different containers, dividing the PGDBP into portions (e.g., portioning), fill-finish (e.g., formulation (e.g., with excipients), packaging, and labeling), distribution, storage, and release into commerce.

In general, downstream processing steps for use in the methods described herein ensure that a reference standard, e.g., composition uniformity, is met by the PGDBP or portions thereof (e.g., dosage forms) after the downstream processing step is completed. In some embodiments, a plurality of portions of a PGDBP that have been finalized by downstream processing steps meet a reference standard, e.g., the same reference standard(s) the PGDBP met. In the same embodiments, at least 50, 60, 70, 80, 85, 90, 95, 99, or 100% of the plurality of finalized portions meet the reference standard. In some embodiments, the PGDBP produced by a method described herein is sufficient such that a plurality of finalized portions meet a reference standard, e.g., the same reference standard(s) the PGDBP met. In the same embodiments, at least 50, 60, 70, 80, 85, 90, 95, 99, or 100% of the plurality of finalized portions meet the reference standard.

EXAMPLES

The Examples below are set forth to aid in the understanding of the inventions, but is not intended to, and should not be construed to, limit its scope in any way.

Example 1. A Method to Produce and Evaluate PGDBPs

FIG. 1 depicts an exemplary method to produce a plurality of dosage forms of a PGDBP. The method begins with analytical method development. Raw materials (RM) are sought out for qualities such as purity, physico-chemical properties, and particle sizes. Vendors providing suitable, e.g., pharmaceutical grade, RMs provide each amino acid (AA) needed (e.g., $AA_a$, $AA_b$, ... $AA_z$) and each excipient (Ex) needed (e.g., $Ex_a$, $Ex_b$, ... $Ex_z$). RMs are combined via blending, e.g., a blending condition; in this example the RMs are combined at room temperature (RT), at room humidity (% RH), in a Ross Ribbon Blender, and with a blender rotation speed of 40 RPM. At various time points ($T_0$, $T_1$ ... $T_n$), the combination is assessed for whether it has met a reference standard, here composition uniformity (e.g., homogeneity) using near infrared spectroscopy (NIR). When the combination (now a PGDBP) is determined to meet the standard, the PGDBP is discharged into a bulk container and either stored as is (e.g., as drug substance) or processed for fill and finish into final dosage forms, e.g., drug product, e.g., stick packs. Select samples of drug product are assessed for portion uniformity by HPLC, under conditions to assess accelerated stability, and if they meet the reference standards for each, they may be assessed for various drug product properties or certified and released for use.

Example 2. Monitoring Homogeneity in Real Time with NIR

Near infrared spectroscopy (NIR) can be used to monitor blending in real time. NIR comprises spectroscopy in the 780-2500 nm range and has the advantage that it can be performed in real time as blending continues, is a fast and non-destructive assessment, can be used with small sample sizes, and very little sample preparation. NIR detects overtone and combination bond vibrations in compounds containing CH, OH, or NH bonds, including amino acids. Due to the overtone and combination modes and large numbers of possible vibrations, NIR spectra are very complex, consisting of many overlapping peaks (referred to as 'multicollinearity'), which result in broad bands. This makes it difficult to interpret NIR spectra visually, assign specific features to specific chemical components or extract information contained in the spectra easily.

Figure 2:
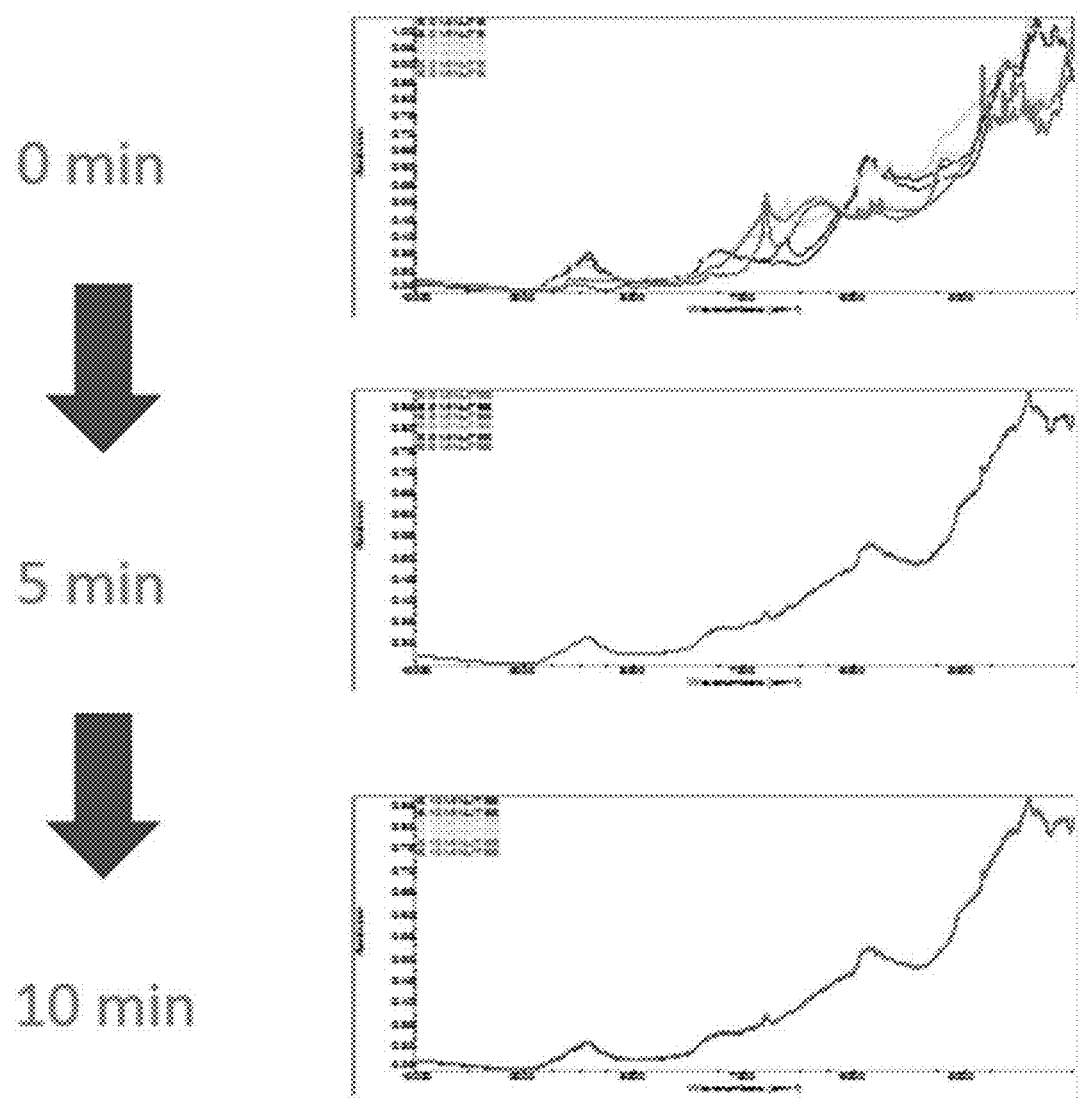
FIG. 2 shows three alignments of NIR spectrographs. Each alignment of spectrographs shows analysis of 6 samples of the combination of amino acid entities, each taken at the same time point from a different region of the blender (see different colored lines). The top alignment of spectrographs depicts data from time 0, the second from 5 minutes into blending, and the third after 10 minutes of blending.
Figure 3B:
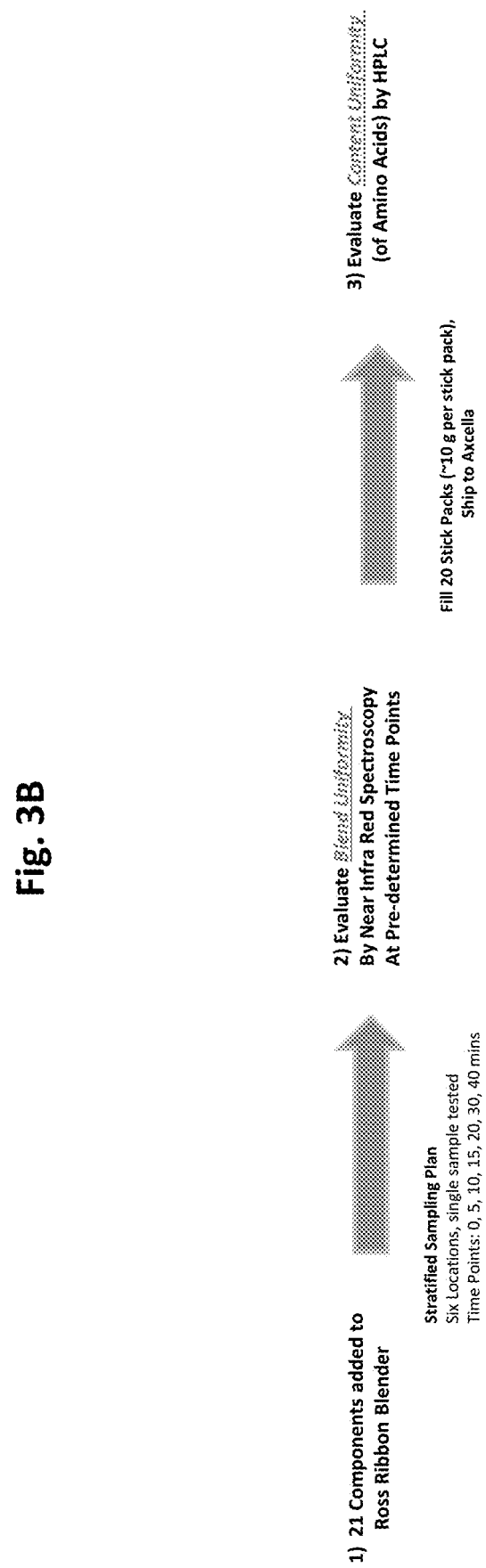
FIG. 3B shows a schematic of how the components are combined in a ribbon blender and sampled using a stratified sampling plan at 6 locations over time points from 0 to 40 minutes, the samples evaluated for blend uniformity using NIR, then the PGDBP portions (e.g., stick packs) are evaluated by HPLC to determine amino acid content.
Figure 3E:
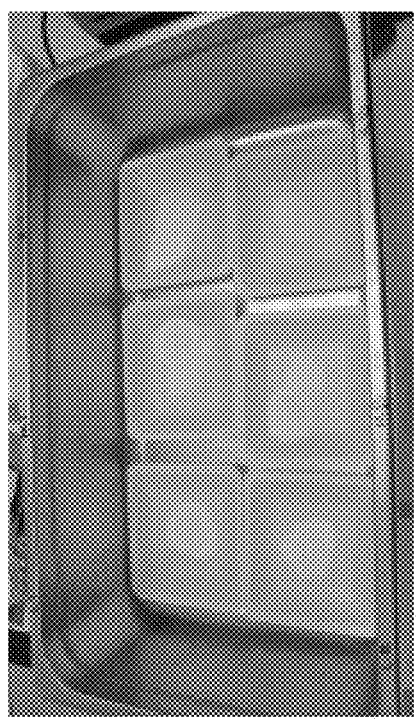
FIG. 3E shows 6 samples taken at time 0.
Figure 3F:
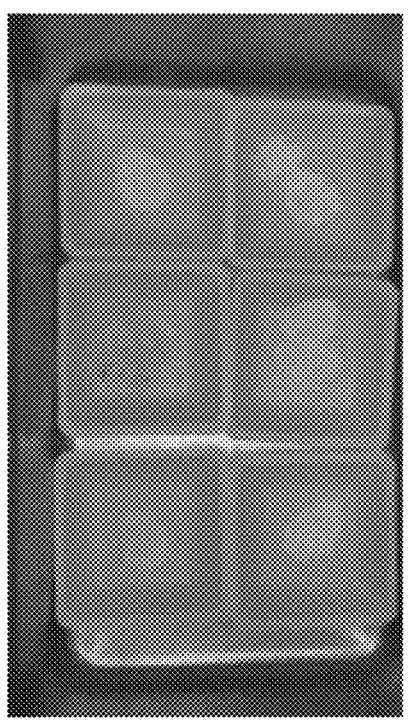
FIG. 3F shows 6 samples taken after 40 minutes of blending.
Figure 3C:
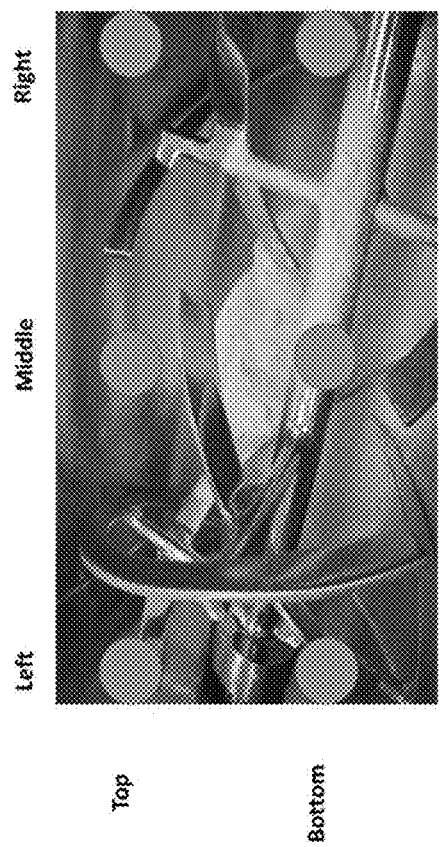
FIG. 3C shows a picture of a ribbon blender containing a dry blended preparation; the blue circles, denoted by positions left, middle, right and top and bottom, denote the 6 locations of the stratified sampling plan.
Figure 3D:
FIG. 3D shows a picture of the ribbon blender with a dry blended preparation at time 0.

However, the dependence of the NIR spectra on a number of variables does not interfere with the spectra's use for determining homogeneity. As a combination of amino acids undergoing blending approaches homogeneity, the NIR spectra of samples taken at various locations in the blender will begin to look more similar, until finally essentially overlapping when homogeneity is achieved (FIG. 2). The change in NIR spectra can be represented in a number of ways. One or several individual wavelengths in the near infrared range can be monitored for absorbance or transmission, or the standard deviation of the average (of the samples from different locations) absorbance or transmission can be used. Any NIR parameter that will converge as homogeneity is achieved can function as a Conformity Index, which represents the progress toward a standard of blend uniformity.

FIG. 3A-3G show this process for an exemplary combination of amino acid entities. A combination of the formula of FIG. 3A was combined (according to the steps of FIG. 3B) in a ribbon blender and blended. Samples were taken at 0, 5, 10, 15, 20, 25, 30, 35, and 40 minutes after the start of blending from the blender positions indicated in FIG. 3C: top left, top middle, top right, bottom left, bottom middle, and bottom right. By eye, the components before blending (FIG. 3D) are separate and not mixed, as seen by the separate distinct regions of color in the combination. A visual comparison of the samples taken at time 0 (FIG. 3E) to the samples taken at 40 minutes of blending (FIG. 3F) shows that the samples at time 0 are different colors from one another, indicative of heterogeneous distribution of the components of the combination, whereas the samples after 40 minutes of blending are essentially the same color, indicative of a substantially homogeneous distribution. The conformity indices (based on the absorbance at a single wavelength in the near infrared range) of samples from various locations in the blender proceeds essentially to convergence after 40 minutes of blending (FIG. 3G), demonstrating that blend uniformity has been achieved.

Example 3. Evaluating Content Uniformity

Figure 4:
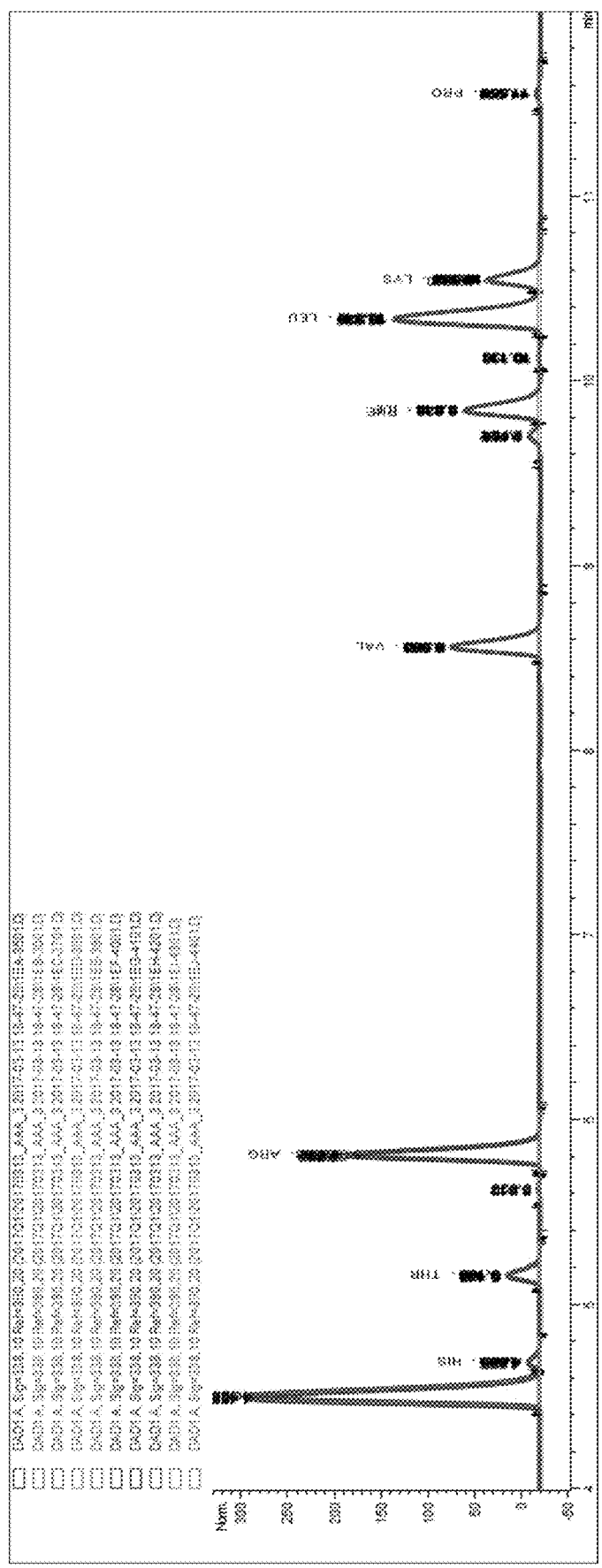
FIG. 4 is an overlay of HPLC chromatograms analyzing the amino acid content of 10 stick packs from a batch of PGDBP. The peaks are assigned to specific amino acids and the amount of the amino acid present in the stick pack can be quantified by integrating to obtain the area under the peak.

In addition to blend uniformity, it is important to establish that the content of each dosage form of the divided PGDBP comprises the expected amount of Active Moiety (the expected amount of amino acid entities). The identity and amount of amino acid present in a sample of PGDBP can be evaluated using HPLC. Amino acids can be derivatized using detectable moieties that alter 1) elution properties of the amino acid, making it easier to separate from a mixture, and 2) the fluorescent or chromatic properties, making the derivatized amino acid easier to detect via fluorescence or visual absorbance spectroscopy. In FIG. 4, OPA-derivatized amino acids from a combination of amino acid entities are analyzed via HPLC, and distinct peaks for each derivatized amino acid are identified. By integrating under the peaks, the amount of the amino acid present in the sample (e.g., in the dosage form, e.g., stick pack) was determined.

Figure 5:
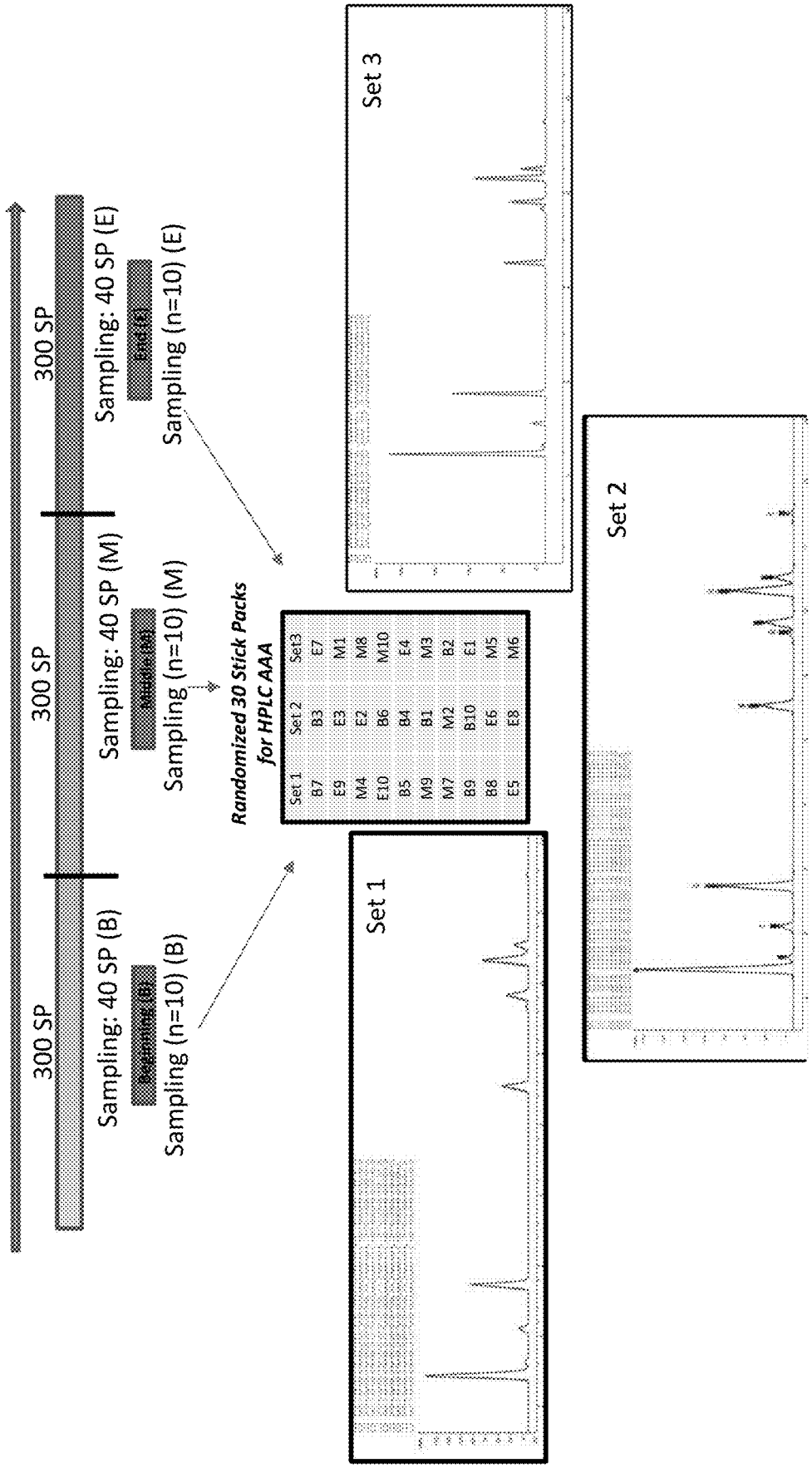
FIG. 5 is a schematic showing an example of how a batch of stick packs of a PGDBP can be evaluated for content uniformity (e.g., dosage uniformity).
Figure 6:
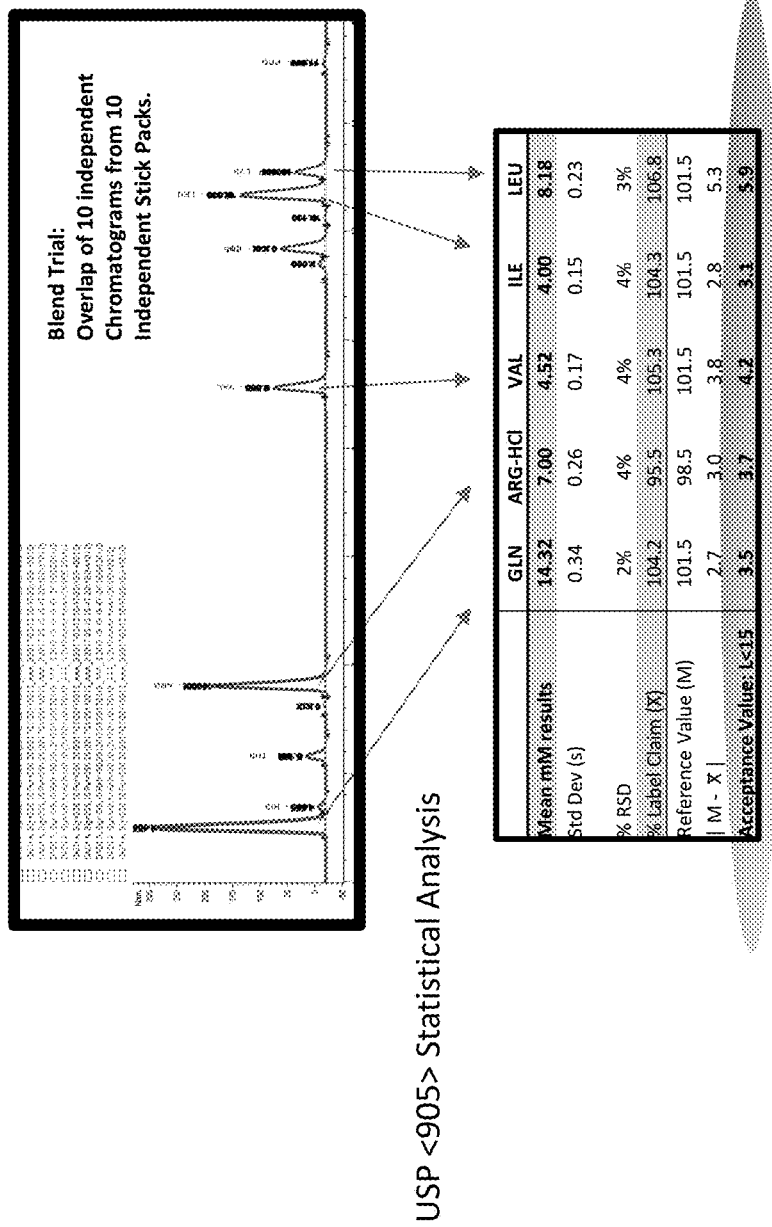
FIG. 6 is a schematic showing how statistical analysis is used to confirm content uniformity. The data from the peaks corresponding to specific derivatized amino acids is analyzed using the statistical methods of the United States Pharmocopeia section <905> to produce the values in the table.

A protocol was constructed to determine whether the amount of amino acids in stick packs produced from drug substance (an exemplary PGDBP) at the beginning of discharge is the same as the amount of amino acids in stick packs produced from drug substance at the end of discharge (FIG. 5). A batch of ~1000 stick packs' (SPs) worth of bulk drug substance is produced, and the first ~300 SP worth are designated the beginning (B), the second ~300 SP worth are designated the middle (M), and the last ~300 SP worth are designated the end (E). 40 SP are selected randomly from the B, the M, and the E, and then 10 are selected randomly from each of the B 40, the M 40, and the E 40. These last 30 are sorted randomly into three sets of ten, for example, as shown, and then HPLC analysis of amino acid content is conducted as in FIG. 4, overlaying the chromatograms. The chromatograms of Set 1, Set 2, and Set 3 (FIG. 5) are, visually, essentially identical, indicative that there is no significant difference between the amino acid content of the doses produced early in discharge compared to doses produced late in discharge, consistent with achieving content uniformity in a single manufacturing batch. FIG. 7A further quantifies and displays this data, showing no significant difference between the amounts of Glutamine, Arginine-HCl, Valine, Isoleucine, and Leucine between stages of discharge. The data from each set of ten samples was further analyzed by the statistical methods of US Pharmacopeia section 905, which recites methods for evaluating and ensuring content uniformity across doses (FIG. 6). In these methods, a final acceptance value (L score) of less than 15 indicates content uniformity (i.e., variation within acceptable levels between doses). Glutamine, Arginine-HCl, Valine, Isoleucine, and Leucine all had L scores below 15, indicating that the sets meet the USP standard for content uniformity.

Figure 7B:
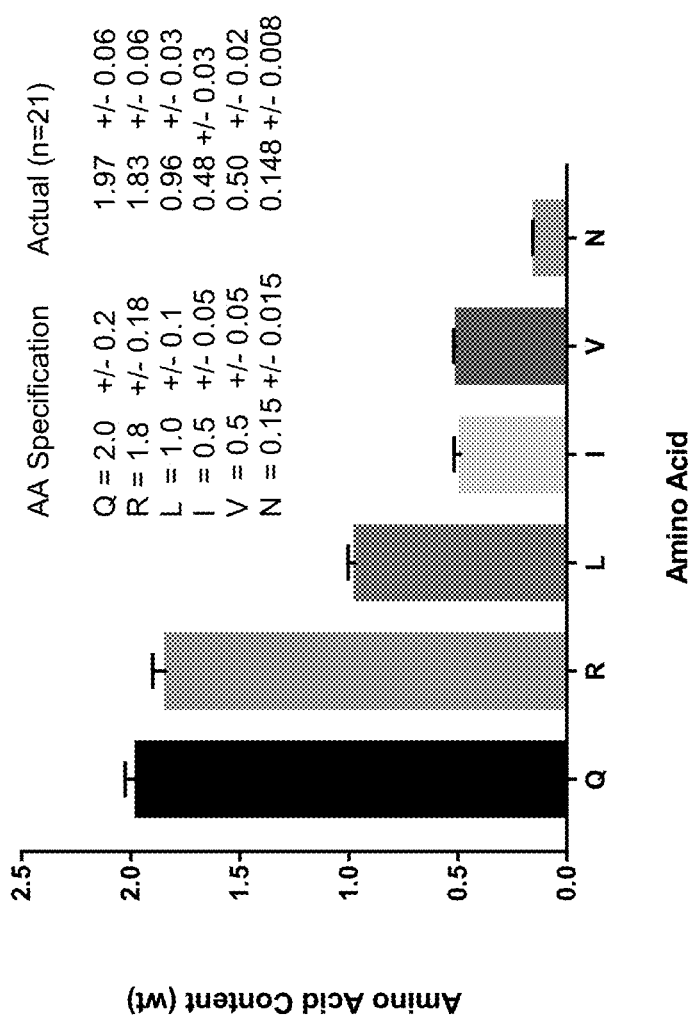
FIG. 7B is a graph showing the average amount of amino acid in 21 different batches of a PGDBP. Error bars are standard error of the mean.

A different exemplary PGDBP was analyzed for content uniformity across different manufacturing batches. Samples from 21 different manufacturing batches of PGDBP, produced over the course of a year, were analyzed by the HPLC methods described above, and the average amount of each amino acid quantified (FIG. 7B). The data show that the average amino acid content for each amino acid was very near to the specified amount of amino acid added for the PGDBP, and the standard error of the mean for each experimentally determined average is less than the 10% variation specified by pharmaceutical standards. This indicates that the amino acid content of the PGDBP doses is uniform across manufacturing batches.

Example 4. Monitoring Homogeneity in Real Time Using NIR—Additional Combinations and Ribbon Blending FIGS. 8A, B, C depicts the change in the NIR spectra and the HPLC chromatograms during the ribbon blending process of a first additional exemplary combination of amino acid entities (the exemplary combination of Table 15). FIG. 8A shows the successive and time-dependent changes in the NIR spectra as the additional exemplary combination is blended in the ribbon blender. At the zero-time point (which can be considered an unblended state), the NIR spectra appear as a composite of multiple components. As blending time proceeded, the combined NIR spectra collapsed into a single-overlapping spectrum. This change in the composite NIR spectra across blending time indicated that an blend uniformity had been achieved.

FIG. 8B shows the HPLC chromatogram of OPA-labeled amino acids taken from the unblended state (time zero) of the additional exemplary combination of amino acid entities of FIG. 8A. FIG. 8C shows the overlap of HPLC chromatograms taken from ten random samples of the additional exemplary combination following 20 mins of ribbon blending. The data taken together indicate that blend homogeneity and content homogeneity had occurred following a process time of 10-20 minutes.

Figure 9A:
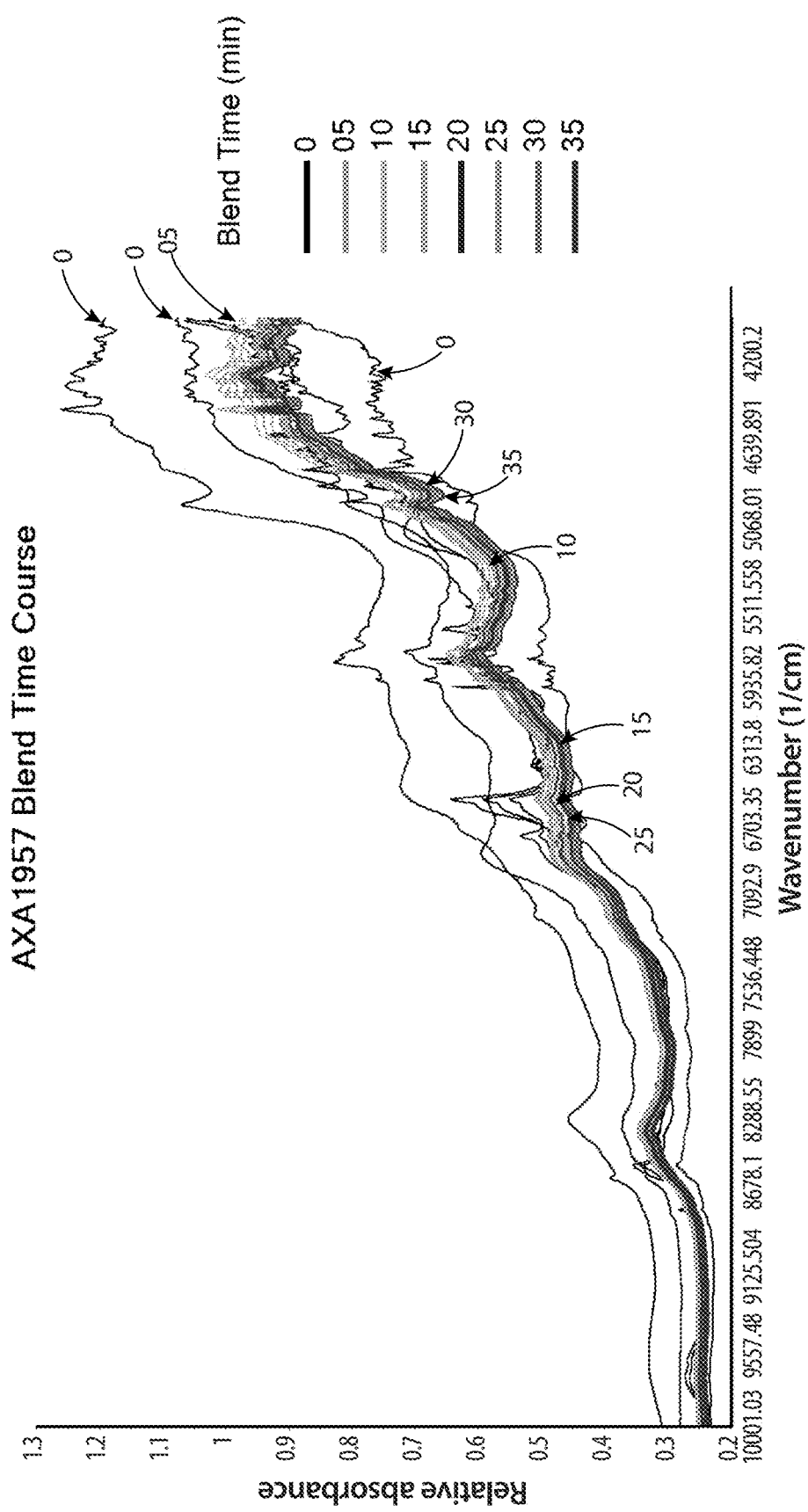
FIG. 9A shows alignments of NIR spectrographs taken at increasing blending times (0, 5, 10, 15, 20, 25, 30, and 35 minutes) of a PGDBP.

FIG. 9A shows multiple NIR spectra of samples taken during the ribbon blending of a second additional exemplary combination of amino acid entities (the exemplary combination of Table 14) at five-minute intervals. The collapse of the spectra at late time points to a single representative spectrum indicates the combination approaches blend uniformity. The histograms in FIG. 9B represents the average and their standard errors of the mean taken from HPLC chromatograms of ten randomly-selected and independent stick packs after 25 minutes of blending. The recovery data is expressed as a percent of label claim. The amino acid recovery values appear to conform to the 90-110 percent acceptance criteria (dotted line). The data when taken together indicated blend and content uniformity had been achieved.

Figure 10A:
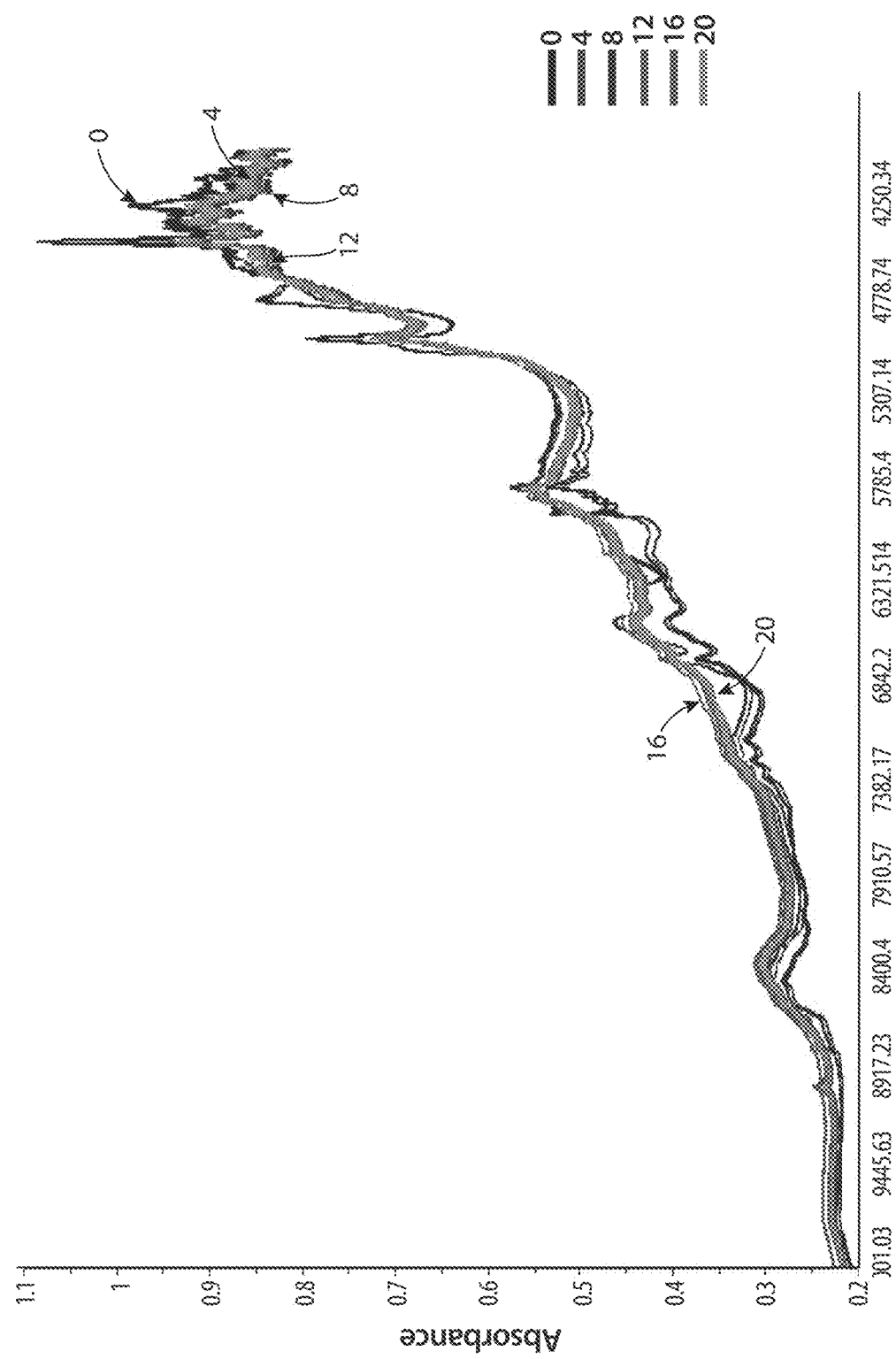
FIG. 10A shows alignments of NIR spectrographs taken at increasing blending times (0, 4, 8, 12, 16, and 20 minutes) of a PGDBP.

FIG. 10A shows the time-dependent approach to blend uniformity during the processing of a third additional exemplary combination of amino acid entities (the exemplary combination of Table 16) using a V-blender. Samples for generating NIR spectra were taken every four minutes. The collapse of the NIR spectra at late time points indicates that the combination has achieved blend uniformity. FIG. 10B represents the average of four randomly-selected independent stick packs and amino acid recovery data is expressed as a 90-110 percent of label claim. The data when taken together, indicate blend and content uniformity had been achieved.

These experiments demonstrate that the methods described herein may be used to achieve blend and content uniformity for additional combinations of amino acid entities and that a variety of blending techniques, including ribbon blending and V-blender blending, are suitable for achieving uniformity.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

What is claimed is:

1. A method of manufacturing a pharmaceutical grade dry blended preparation (PGDBP) comprising at least four pharmaceutical grade amino acid entities, said method comprising:

forming a combination of at least four pharmaceutical grade amino acid entities and blending the combination at a temperature lower than 40° C. for a time sufficient to achieve a PGDBP having a mass of at least 10 kg, the combination being blended substantially lacking solvent, wherein:

the PGDBP comprises a level of a contaminant that is less than 0.15% (w/w), and less than 20%, by weight, of at least one of the pharmaceutical grade amino acid entities transforms from a crystalline state to an amorphous state during blending and wherein at least 50% of the pharmaceutical grade amino acid entities are in a crystalline state during blending.

2. The method of claim 1, further comprising portioning the PGDBP into a plurality of portions of the PGDBP.

3. The method of claim 1, wherein the blending is sufficient to achieve blend and content uniformity without generating impurities or inducing blend heterogeneity.

4. The method of claim 1, further comprising, after blending, selecting or taking a downstream processing step chosen from: dividing the PGDBP into portions, fill-finish, packaging, labeling, shipping, distribution, storage, or release into commerce.

5. The method of claim 1, wherein the PGDBP is suitable for oral administration.

6. The method of claim 5, wherein the combination or PGDBP further comprises one or more excipients and/or oral administration components.

7. The method of claim 1, wherein the PGDBP comprises less than 10% (w/w) of a tastant, a bitterness covering agent, flavorants, a sweetener, odor masking agent, a wetting agent, a stabilizing/thickening agent, or a coloring agent.

8. The method of claim 1, wherein blending occurs with one, two, or three of the following properties:
   i) blending does not effect a transition from a crystalline state to an amorphous state; or
   ii) blending comprises blending or mixing in a blender or mixer at a speed of less than 15,000 rpm.

9. The method of claim 1, wherein the PGDBP comprises:
   a) a leucine amino acid entity,
   b) an arginine amino acid entity,
   c) glutamine amino acid entity; and
   d) a N-acetylcysteine (NAC)-entity.

10. The method of claim 1, wherein the combination being blended substantially lacks water.

11. The method of claim 1, wherein the amount of a pharmaceutical grade amino acid entity in the PGDBP measured at a sampling point comprises a weight percent, and wherein the amount of the pharmaceutical grade amino acid entity present in the PGDBP as a whole comprises a weight percent.

12. The PGDBP produced by claim 1.

13. The plurality of portions of a PGDBP produced by claim 2.

14. A method of manufacturing a plurality of portions of a pharmaceutical grade dry blended preparation (PGDBP) comprising at least four pharmaceutical grade amino acid entities, said method comprising:
   blending a combination of at least four pharmaceutical grade amino acid entities at a temperature lower than 40° C. for a time sufficient to achieve a content uniformity standard thereby making a PGDBP, wherein less than 20%, by weight, of at least one of the pharmaceutical grade amino acid entities transforms from a crystalline state to an amorphous state during blending and wherein at least 50% of the pharmaceutical grade amino acid entities are in a crystalline state during blending, and
   dividing the PGDBP into a plurality of portions, wherein at least 1% of the plurality of portions are test portions, and wherein the amount of a component present in at least 90% of test portions differs from a reference value by no more than 10%.

15. The method of claim 14, wherein the amount of the component present in at least 90% of test portions is the percent of the component present in at least 90% of test portions, and wherein the reference value is the percent of the component present in the PGDBP as a whole.

* * * * *